(12) United States Patent
Li et al.

(10) Patent No.: US 9,745,278 B2
(45) Date of Patent: *Aug. 29, 2017

(54) GROUP OF STAT3 PATHWAY INHIBITORS AND CANCER STEM CELL PATHWAY INHIBITORS

(75) Inventors: Chiang Jia Li, Cambridge, MA (US); Harry Rogoff, Wrentham, MA (US); Youzhi Li, Westwood, MA (US); Jifeng Liu, Winchester, MA (US); Wei Li, Wayland, MA (US)

(73) Assignee: Boston Biomedical, Inc., Cambridge, MA (US)

( * ) Notice: Subject to any disclaimer, the term of this patent is extended or adjusted under 35 U.S.C. 154(b) by 841 days.

This patent is subject to a terminal disclaimer.

(21) Appl. No.: 12/677,513

(22) PCT Filed: Sep. 10, 2008

(86) PCT No.: PCT/US2008/075903
§ 371 (c)(1),
(2), (4) Date: Mar. 20, 2012

(87) PCT Pub. No.: WO2009/036099
PCT Pub. Date: Mar. 19, 2009

(65) Prior Publication Data
US 2012/0252763 A1    Oct. 4, 2012

Related U.S. Application Data

(60) Provisional application No. 60/971,144, filed on Sep. 10, 2007, provisional application No. 61/013,372, filed on Dec. 13, 2007.

(51) Int. Cl.
| | | |
|---|---|---|
| *A61K 31/655* | (2006.01) | |
| *C07D 307/92* | (2006.01) | |
| *A61K 31/38* | (2006.01) | |
| *C07D 333/74* | (2006.01) | |

(52) U.S. Cl.
CPC ............ *C07D 307/92* (2013.01); *A61K 31/38* (2013.01); *C07D 333/74* (2013.01)

(58) Field of Classification Search
None
See application file for complete search history.

(56) References Cited

U.S. PATENT DOCUMENTS

| | | |
|---|---|---|
| 6,337,346 B1 | 1/2002 | Lee et al. |
| 6,395,773 B1 | 5/2002 | Hirai et al. |
| 6,828,337 B2 | 12/2004 | Belloni et al. |
| 7,019,147 B1 | 3/2006 | Barth et al. |
| 2004/0006009 A1 | 1/2004 | Larsen |
| 2004/0092428 A1* | 5/2004 | Chen .................. A61K 9/1075 424/452 |
| 2004/0138189 A1 | 7/2004 | Sebti et al. |
| 2005/0010060 A1 | 1/2005 | Blokhin et al. |
| 2005/0049207 A1* | 3/2005 | Kaufmann ............... A23L 1/293 514/28 |
| 2006/0019256 A1 | 1/2006 | Clarke et al. |
| 2006/0099251 A1 | 5/2006 | Johannsson |
| 2006/0222696 A1 | 10/2006 | Okada et al. |
| 2006/0247318 A1 | 11/2006 | Song et al. |
| 2006/0252674 A1 | 11/2006 | Peritt et al. |
| 2006/0279011 A1 | 12/2006 | Palakodaty et al. |
| 2007/0060521 A1 | 3/2007 | Jove et al. |
| 2007/0123502 A1 | 5/2007 | Turkson et al. |
| 2007/0238770 A1 | 10/2007 | Gougoutas et al. |
| 2009/0042977 A1 | 2/2009 | Tokuda et al. |

FOREIGN PATENT DOCUMENTS

| | | |
|---|---|---|
| CA | 2017806 A1 | 4/1994 |
| EP | 1134216 A1 | 9/2001 |
| EP | 1860103 B1 | 3/2006 |
| JP | 04139177 A | 5/1992 |
| JP | H11021284 A1 | 1/1999 |
| JP | 2004224802 A | 8/2004 |
| WO | 9962909 A3 | 12/1999 |
| WO | WO0044774 | 8/2000 |
| WO | WO 2004026253 A2 * | 4/2004 |
| WO | WO-2004026253 A2 | 4/2004 |
| WO | 2004046120 A2 | 6/2004 |

(Continued)

OTHER PUBLICATIONS

Kang et al., "A new route to naphtho[2,3-b]furan-4,9-diones from thiosubstituted 1,4-naphthoquinones," Journal of the Chemical Society. Perkin transactions 1, 1990(3):441-445.*
Anderson (Chem and Biol 10:787-797, 2003).*
Peraza-Sanchez et al., "Cytotoxic Constituents of the Roots of Ekmanianthe longiflora," J. Nat. Prod. 2000, 63, 492-495.*
Lee et al., "Efficient Synthesis of Cytotoxic Furonaphthoquinone Natural Products," Synthetic Communications, 31(3), 381-386 (2001).*
Taylor, "Herbal Secrets of the Rainforest", 2nd Edition (2003).*
Mailer et al., "Potential Antipsoriatic Agents: Lapacho Compounds as Potent Inhibitors of HaCaT Cell Growth," J. Nat. Prod. 1999, 62, 1134-1136.*
Solozano et al., "Decrease glycolytic metabolism accelerates apoptosis in response to 2-acetyl furanonaphthoquinone in K1735 melanoma irrespective of bcl-2 overexpression," Cancer Biology and Therapy, published online Dec. 27, 2004.*

(Continued)

*Primary Examiner* — Craig Ricci
(74) *Attorney, Agent, or Firm* — Finnegan, Henderson, Farabow, Garrett & Dunner LLP

(57) ABSTRACT

The present invention relates to the use of a novel class of cancer stem cell pathway (CSCP) inhibitors; to methods of using such compounds to treat refractory, recurrent, or metastatic cancers; to methods of selective killing cancer cells by using such compounds with specific administration regimen; to methods of targeting cancer stem cells by inhibiting Stat3 pathway; to methods of using novel compounds in the treatment of conditions or disorders in a mammal related to aberrant Stat3 pathway activity; and to processes for preparing such compounds and intermediates thereof, and to the pharmaceutical composition of relevant compounds, and to the specific methods of administration of these compounds.

53 Claims, 17 Drawing Sheets

(56) References Cited

FOREIGN PATENT DOCUMENTS

| | | |
|---|---|---|
| WO | WO-2005033048 A2 | 4/2005 |
| WO | WO2005058829 A3 | 6/2005 |
| WO | WO2005110477 | 11/2005 |
| WO | WO-2006056399 A2 | 6/2006 |
| WO | WO2006098355 A1 | 9/2006 |
| WO | WO-2006113790 A2 | 10/2006 |
| WO | WO-2007100640 A2 | 9/2007 |
| WO | WO-2007115269 A2 | 10/2007 |
| WO | WO2008094321 A3 | 8/2008 |
| WO | WO-2006091837 A3 | 4/2009 |

OTHER PUBLICATIONS

Pereira et al., "Invasion-associated MMP-2 and MMP-9 are up-regulated intracellularly in concert with apoptosis linked to melanoma cell detachment," Clinical and Experimental Metastasis (2005) 22:285-295.*
Stout (Blog entitled "No Cancer", available online at http://nocancer.blogspot.com/2005/05/14-pau-darco.html, published May 24, 2005).*
Steinert et al (J Chromato A 693:281-287, 1995).*
Lin et al (Cancer Res 71:7226-7237, 2011).*
Clarke, et al. "Cancer Stem Cells—Perspectives on Current Status and Future Directions: AACR Workshop on Cancer Stem Cells." *Cancer Research*. 66.19(2006):9339-9344.
Colman, et al. "Effect of a small molecule inhibitor of the JAK2/STAT3 pathway on self-renewal of glioblastoma stem cells." *Journal of Clinical Oncology*. 26.1565(2008):abstract 2003.
Desmond, et al. "The synthetic furanonaphthoquinone induces growth arrest, apoptosis and differentiation in a variety of leukaemias and multiple myeloma cells." *British Journal of Haematology*. 131.4(2005):520-529.
Frank. "STAT3 as a central mediator of neoplastic cellular transformation." *Cancer Letters*. 251.2(2007):199-210.
Hirai, et al. "Furanonaphthoquinone Analogs Possessing Preferential Antitumor Activity Compared to Normal Cells." *Cancer Detection and Prevention*. 23.6(1999):539-550.
Katoh and Katoh. "STAT3-induced WNT5A signaling loop in embryonic stem cells, adult normal tissues, chronic persistent inflammation, rheumatoid arthritis and cancer (Review)." *International Journal of Molecular Medicine*. 19.2(2007):273-278.
Yao, et al. "Experimental study on the growth inhibition of bladder cancer cells by signal conduction blocker AG490." *Journal of Clinical Urology*. 21.5(2006):379-382.
Zhou, et al. "Activation of the PTEN/mTOR/STAT3 pathway in breast cancer stem-like cells is required for viability and maintenance." *PNAS*. 104.41(2007):16158-16163.
Zhou, et al. "Corrections: Activation of the PTEN/mTOR/STAT3 pathway in breast cancer stem-like cells is required for viability and maintenance." *PNAS*. 104.49(2007):19655-19656.
Koyoma et al. "Micellar Electrokinetic Chromatography (MEKC) Separation of Furanonaphthoquinones from Tabebuia impetiginosa" Chem. Pharm. Bull. (Tokyo), Jun. 2000, 48(6) 873-875.
Solorzano et al. "Decreased glycolytic metabolism accelerates apoptosis in response to 2-acetyl furanonaphthoquinone in K1735 melanoma irrespective of bcl-2 overexpression" Cancer Biol. Ther. (Mar. 2005) vol. 4, No. 3, pp. 329-335. [Abstract provided].
Ogawa et al. "Cytotoxic Activity Toward KB Cells of 2-Substituted Naphtho[2,3-*b*]furan-4,9-diones and Their Related Compounds." *Biosci. Biotechnol. Biochem*. 70.4(2006):1009-1012.
Paridaens et al. "Paclitaxel Versus Doxorubicin as First-Line Single-Agent Chemotherapy for Metastatic Breast Cancer: A European Organization for Research and Treatment of Cancer Randomized Study With Cross-Over." *J. Clin. Oncol*. 18.4(2000):724-733. (Abstract Only).
Qiuwen et al., "Evaluation of the potential cancer chemotherapeutic efficacy of natural product isolates employing in vivo hollow fiber tests," Journal of Natural Products, 65:842-850 (2002).
Rao and Kingston, "Plant anticancer agents. XII. isolation and structure elucidation of new cytotoxic quinones from Tabebuia cassinoides," Journal of Natural Products, 45(5):600-604 (1982).
Takano et al., "Tumor-specific cytotoxicity and type of cell death induced by naphtho[2,3-b]furan-4,9-diones and related compounds in human tumor cell lines: relationship to electronic structure," Anticancer Research, 29:455-464 (2009).
Eyong et al., "Semisynthesis and antitumoral activity of 2-acetylfuranonaphthoquinone and other naphthoquinone derivatives from lapachol," Bioorganic & Medicinal Chemistry Letters, 18:5387-5390 (2008).
Bonnet, "Normal and leukaemic stem cells," Br J Haematol, 130(4):469-79 (2005).
Bonnet and Dick, "Human acute myeloid leukemia is organized as a hierarchy that originates from a primitive hematopoietic cell," Nat Med, 3(7):730-7 (1997).
Hambardzumyan et al., "Radiation resistance and stem-like cells in brain tumors," Cancer Cell, 10(6):454-6 (2006).
Ailles and Weissman, "Cancer stem cells in solid tumors," Curr Opin Biotechnol, 18(5):460-6 (2007).
Jones et al., "Cancer stem cells: are we missing the target?," J Natl Cancer Inst, 96(8):583-5 (2004).
Ho et al., "Side population in human lung cancer cell lines and tumors is enriched with stem-like cancer cells," Cancer Res., 67(10):4827-33 (2007).
Wang et al., "Identification of cancer stem cell-like side population cells in human nasopharyngeal carcinoma cell line," Cancer Res, 67(8):3716-24 (2007).
Doyle and Ross, "Multidrug resistance mediated by the breast cancer resistance protein BCRP (ABCG2)," Oncogene, 22(47):7340-58 (2003).
Alvi et al., "Functional and molecular characterization of mammary side population cells," Breast Cancer Res, 5(1): R1-8 (2003).
Frank et al., "ABCB5-mediated doxorubicin transport and chemoresistance in human malignant melanoma," Cancer Res, 65(10):4320-33 (2005).
Kondo et al., "Persistence of a small subpopulation of cancer stem-like cells in the C6 glioma cell line," Proc Natl Acad Sci USA, 101(3):781-6 (2004).
Goodell et al., "Isolation and functional properties of murine hematopoietic stem cells that are replicating in vivo," J Exp Med, 183(4):1797-806 (1996).
Collins et al., "Prospective identification of tumorigenic prostate cancer stem cells," Cancer Res, 65(23):10946-51 (2005).
Li et al., "Identification of pancreatic cancer stem cells," Cancer Res, 67(3):1030-7(2007).
Prince et al., "Identification of a subpopulation of cells with cancer stem cell properties in head and neck squamous cell carcinoma," Proc Natl Acad Sci USA, 132(7):2542-56(2007).
Singh et al., "Identification of a cancer stem cell in human brain tumors," Cancer Res, 63(18):5821-8(2003).
Dalerba et al., "Phenotypic characterization of human colorectal cancer stem cells," Proc Nati Acad Sci USA, 104 (24):10158-63(2007).
Pedranzini, Leitch, and Bromberg, "Stat3 is required for the development of skin cancer," J Clin Invest, 114 (5):619-22(2004).
Catlett-Falcone et al., "Constitutive activation of Stat3 signaling confers resistance to apoptosis in human U266 myeloma cells," Immunity, 10(1):105-15(1999).
Bromberg et al., "Stat3 as an oncogene," Cell, 98(3):295-303(1999).
Kanda et al., "STAT3 is constitutively activated and supports cell survival in association with survivin expression in gastric cancer cells," Oncogene, 23(28):6921-9,(2004).
Schlette et al., "Survivin expression predicts poorer prognosis in anaplastic large-cell lymphoma," J Clin Oncol, 22 (9):1682-8(2004).
Niu et al., "Constitutive Stat3 activity up-regulates VEGF expression and tumor angiogenesis," Oncogene, 21 (13):2000-8(2002).
Xie et al., "Stat3 activation regulates the expression of matrix metalloproteinase-2 and tumor invasion and metastasis," Oncogene, 23(20):3550-60(2004).

(56) References Cited

OTHER PUBLICATIONS

Burdelya et al., "Stat3 activity in melanoma cells affects migration of immune effector cells and nitric oxide-mediated antitumor effects," J Immunol, 174(7):3925-31(2005).
Zhang et al., "Intratumoral delivery and suppression of prostate tumor growth by attenuated *Salmonella enterica* serovar typhimurium carrying plasmid-based small interfering RNAs," Cancer Res, 67(12):5859-64(2007).
Campbell, "Cytokine-mediated inflammation, tumorigenesis, and disease associated JAK/STAT/SOCS signaling circuits in the CNS," Brain Res Brain Res Rev, 48(2):166-77(2005).
Harris et al., "Cutting edge: An in vivo requirements for STAT3 signaling in TH17 development and TH17-dependent autoimmunity," J Immunol, 179(7):4313-7(2007).
Libby, Ridker, and Maseri, "Inflammation and atherosclerosis," Circulation, 105(9):1135-43(2002).
Stephens et al., "A common functional variant in the interleukin-6 gene is associated with increased body mass index in subjects with type 2 diabetes mellitus," Mol Genet Metab, 82(2):180-6(2004).
Cesari et al., "Inflammatory markers and onset of cardiovascular events: results from the Health ABC study," Circulation, 108(19):2317-22(2003).
Orshal and Khalil, "Interleukin-6 impairs endothelium-dependent No-cGMP-mediated relaxation and enhances contraction in systemic vessels of pregnant rats," Am J Physiol Regul Integr Comp Physiol, 286(6):1013-23(2004).
Manolagas, "Role of cytokines in bone resorption," Bone, 17(2 Suppl):63S-67S(1995).
Watson and Miller, "Elevated levels of members of the STAT family of transcription factors in breast carcinoma nuclear extracts," Br J Cancer, 71(4):840-4(1995).
Song and Grandis, "STAT signaling in head and neck cancer," Oncogene, 19(21):2489-95(2000).
Song et al., "Activation of Stat3 by receptor tyrosine kinases and cytokines regulates survival in human non-small cell carcinoma cells," Oncogene, 22(27):4150-65(2003).
Savarese et al., "Coexpression of oncostatin M and its receptors and evidence for STAT3 activation in human ovarian carcinomas," Cytokine, 17(6):324-34(2002).
Toyonaga et al., "Blockade of constitutively activated Janus kinase/signal transducer and activator of transcription-3 pathway inhibits growth of human pancreatic cancer," Cancer Lett, 201(1):107-16(2003).
Corvinus et al., "Persistent STAT3 activation in colon cancer is associated with enhanced cell proliferation and tumor growth," Neoplasia, 7(6):545-55(2005).
Gao et al., "Constitutive activation of JAK-STAT3 signaling by BRCA1 in human prostate cancer cells," FEBS Lett, 488(3):179-84(2001).
Buettner, Mora, and Jove, "Activated STAT signaling in human tumors provides novel molecular targets for the therapeutic intervention," Clin Cancer Res, 8(4):945-54(2002).
Carson, "Interferon-alpha-induced activation of signal transducer and activator of transcription proteins in malignant melanoma," Clin Cancer Res, 4(9):2219-28(1998).
Chen et al., "Stat3 activation in human endometrial and cervical cancers," Br J Cancer, 96(4):591-9(2007).
Lai et al., "STAT3 is activated in a subset of the Ewing sarcoma family of tumours," J Pathol, 208(5):624-32(2006).
Punjabi et al., "Persistent activation of STAT3 by latent Kaposi's sarcoma-associated herpesvirus infection of endothelial cells," J Virol, 81(5):2449-58(2007).
Schaefer et al., "Constitutive activation of Stat3alpha in brain tumors: localization to tumor endothelial cells and activation by the endothelial tyrosine kinase receptor (VEGFR-2)," Oncogene, 21(13):2058-65(2002).
Puthier, Bataille, and Amiot, "IL-6 up-regulates mcl-1in human myeloma cells through JAK/STAT rather than ras/MAP kinase pathway," Eur J Immunol, 29(12):3945-50(1999).

Spiekermann et al., "Constitutive activation of STAT transcription factors in acute myelogenous leukemia," Eur J Haematol, 67(2):63-71(2001).
Epling-Burnette et al., "Inhibition of STAT3 signaling leads to apoptosis of leukemic large granular lymphocytes and decreased Mgm expression," J Clin Invest, 107(3):351-62(2001).
Weber-Nordt et al., "Constitutive activation of STAT proteins in primary lymphoid and myeloid leukemia cells and in Epstein-Barr virus (EBV)-related lymphoma cell lines," Blood, 88(3):809-16(1996).
Sommer et al., "In vivo activation of STAT3 in cutaneous T-cell lymphoma. Evidence for an antiapoptotic functions of STAT3," Leukemia, 18(7):1288-95(2004).
Lai et al., "Signal transducer and activator of transcription-3 activation contributes to high tissue inhibitor of metalloproteinase-1 expression in anaplastic lymphoma kinase-positive anaplastic large cell lymphoma," Am J Pathol, 164(6):2251-8(2004).
Fu, "STAT3 in immune responses and inflammatory bowel disease," Cell Res, 16(2):214-9(2006).
Krause et al., "Rheumatoid arthritis synoviocyte survival is dependent on Stat3," J Immunol, 169(11):6610-6(2002).
Lovato et al., "Constitutive STAT3 activation in intestinal T cells from patients with Crohn's disease," J Biol Chem, 278(19):16777-81(2003).
Ishihara and Hirano, "IL-6 in autoimmune disease and chronic inflammatory proliferative disease," Cytokine Growth Factor Rev, 13(4-5):357-68(2002).
Ivashkiv and Tassiulas, "Can SOCS make arthritis better?", J Clin Invest, 111(6):795-7(2003).
Sengupta et al., "Activation of monocyte effector genes and STAT family transcription factors by inflammatory synovial fluid is independent of interferon gamma," J Exp Med, 181(3):1015-25(1995).
Shouda et al., "Induction of the cytokine signal regulator SOCS3/CIS3 as a therapeutic strategy for treating inflammatory arthritis," J Clin Invest, 108(12):1781-8(2001).
Simeone-Penney et al., "Airway epithelial STAT3 is required for allergic inflammation in a murine model of asthma," J Immunol, 178(10):6191-9(2007).
Benkhart et al., "Role of Stat3 in lipopolysaccharide-induced IL-10 gene expression," J Immunol, 165(3):1612-7 (2000).
Lim et al., "Stat3 contributes to keloid pathogenesis via promoting collagen production, cell proliferation and migration," Oncogene, 25(39):5416-25(2006).
Arany et al., "Correlation between pretreatment levels of interferon response genes and clinical responses to an immune response modifier (Imiquimod) in genital warts," Antimicrob Agents Chemother, 44(7):1869-73(2000).
Tefferi, "Classification, diagnosis and management of myeloproliferative disorders in the JAK2V617F era," Hematology Am Soc Hematol Educ Program, 240-5(2006).
Roder et al., "STAT3 is constitutively active in some patients with Polycythemia rubra vera," Exp Hematol, 29 (6):694-702(2001).
Kim et al., "JAK-STAT signaling mediates gangliosides-induced inflammatory responses in brain microglial cells," J Mi Chem, 277(43):40594-601(2002).
Stelmasiak et al., "Interleukin-6 concentration in serum and cerebrospinal fluid in multiple sclerosis patients," Med Sci Monit, 6(6):1104-8(2000).
Ponti et al., "Isolation and in vitro propagation of tumorigenic breast cancer cells with stem/progenitor cell properties," Cancer Res, 65(13):5506-11(2005).
Szotek et al., "Ovarian cancer side population defines cells with stem cell-like characteristics and Mullerian Inhibiting Substance responsiveness," Proc Natl Acad Sci USA, 103(30):11154-9(2006).
Al-Hajj et al., "Therapeutic implications of cancer stem cells," Curr Opin Genet Dev, 14(1):43-7(2004).
Bleau et al., "New Strategy for the analysis of phenotypic marker antigens in brain tumor-derived neurospheres in mice and humans," NEurosurg Focus, 24(3-4):E28(2008).
Kusaba,"Expression of p-STAT3 in human colorectal adenocarcinoma and adenoma; correlation with clinicopathological factors" journal of Clinical Pathology (2005) 58(8) 833-838.

(56) References Cited

OTHER PUBLICATIONS

Lande "The Relationship Between Membrane Fluidity and Perrheabilities to Water, Solutes, Ammonia, and Protons." J. Gen. Physiol, 106(1995):67-84.
Lassmann, "STAT3 mRNA and protein expression in colorectal cancer: effects on STAT3-inducible targets linked to cell survival and proliferation" J Clin Pathol. (2007);60(2):173-179.
Lau, "Inhibition of Stat3 activity by YC-1 enhances chemo-sensitivity in hepatocellular carcinoma" Cancer Blot Ther. (2007) 6(12):1900-1907.
Leong, "Targeted inhibition of Stat3 with a decoy oligonucleotide abrogates head and neck cancer cell growth" Proc Nati Aced Sci USA (2003) 1;100(7): 4138-43.
Li, "Autocrine-mediated activation of STAT3 correlates with cell proliferation in breast carcinoma lines" . J. Biol. Chem.(2002) 277, 17397-17405.
Li, "Inhibition of growth and metastasis of human hepatocellular carcinoma by antisense oligonucleotide targeting signal transducer and activator of transcription 3" Clin Cancer Res. (2006) 1,12(23):7140-8.
Lin, "Constitutive activation of JAK3/STAT3 in colon carcinoma tumors and cell lines: inhibition of JAK3/STAT3 signaling induces apoptosis and cell cycle arrest of colon carcinoma cells" Am J Pathol (2005) 167:969-980.
Lin, "Significance of the expression of phosphorylated signal transducer and activator of transcription-3—Akt, and cyclin D1 in angiosarcoma" J. Derr. Soi. (2007) 48(1) 64-66 Lin, J. Derr. Sci. (2007) 48(1) 71-73.
Lipinski "Experimental and Computational Approaches to Estimate Solubility and Permeability in Drug Discovery and Development Settings." Adv. Drug Deliv, Rev, 46,1-3(2001):3-26.
Liu, "Expression and clinical significance of COX-2, p-Stat3, and p-Stat5 in esophageal carcinoma." Ai Zheng (2007) 26(6):468 62.
Lopes "Efficient Synthesis of Cytotoxic Quinones: Z-Acteyk4H, 9H-naphtho[2,3-b]furan-4,9-dione (6) and (±)-2-(1 Hydroxyethyl)-41-1,9H-naphtho[2,3-b]furan-4,9-dione (7)," Journal ofhleterocyclic Chemistry, (1934), vol. 21, pp. 621-622.
Lwamaru "A novel inhibitor of the STAT3 pathway induces apoptosis in malignant glioma cells both in vitro and in vivo" Oncogene (2007) 26, 2435-2444.
Ma "Identification and Characteristic of Tumorigenic Liver Cancer Stem/Progenitor Cells." Gastroenterology. 2007;132 (7):2542-56.
Ma, "Constitutive activation of Stat3 signaling pathway in human colorectal carcinoma" World J Gastroent. (2004) 10 (11): 1569-1573.
Masuda, Constitutive activation of signal transducers and activators of transcription 3 correlates with cyclin D1 overexpression and may provide a novel prognostic marker in head and neck squamous cell carcinoma Cancer Res. (2002) 62: 3351-3355.
Mizoguchi, "Activation of STAT3, MAPK, and AKT in malignant astrocytic gliomas: correlation with EGFR status, tumor grade, and survival" Journal of Neuropathology and Experimental Neurology (2006) 65(12)1181-1188.
Mora, "Constitutive activation of Stat3 in human prostate tumors and cell lines: direct inhibition of Stat3 signaling induces apoptosis of prostate cancer cells" Cancer Res (2002) 62(22): 6659-6666.
Morrissett "High-throughput crystallization: polymorphs, salts, co-crystals and solvates of pharmaceutical solids" Adv. Drug Delivery Rev. 2004, 56, 275-300.
Muller "Potential antipsoriatic agents: lapacho compounds as potent inhibitors of HaCaT cell growth" J Nat Prod 62:1134-1136, 1999.
Nielsen, "Inhibition of constitutively activated Stat3 correlates with altered Bcl-2/Bax expression and induction of apoptosis in mycosis fungoides tumor cells" Leukemia. (1999) 13(5)135-8.
Ning, "Signal transducer and activator of transcription 3 activation is required for Asp(816) mutant c-Kit-mediated cytokine-independent survival and proliferation in human leukemia cells" Blood (2001) 97:3559-3567.
Niu, "Gene therapy with dominant-negative Stat3 suppresses growth of the murine melanoma B16 tumor in vivo" Cancer Res. (1999) 15;59(20):5059-63.
Niu, "Roles of activated Src and Stat3 signaling in melanoma tumor cell growth" Oncogene (2002) 21(46):7001-10.
Ogawa, "Cytotoxic Activity toward KB Cells of 2-Substituted Naphtho[2,3-b]furan-4,9-diones and Their Related Compounds," Biosci. Biotechnol. Biochem., 70(4), 1009-1012, (2006).
Peraza-Sanchez "Cytotoxic Constituents of the Roots of Ekmanianthe longiflora," Journal of Natural Products, (2000), vol. 63, pp. 492-495.
Qiu, "RNA interference-mediated signal transducers and activators of transcription 3 gene silencing inhibits invasion and metastasis of human pancreatic cancer cells" Cancer Sci. (2007) 98(7):1099-106.
Rahaman, "Inhibition of constitutively active Stat3 suppresses proliferation and induces apoptosis in glioblastoma muitiforme cells" Oncogene (2002) 21 55:8404-8413.
Rawat, "Constitutive activation of STAT3 is associated with the acquisition of an interleukin 6-independent phenotype by murine plasmacytomas and hybridomnas" Blood. (2000) 15; 96(10):3514-21.
Ricci-Vitiani "Identification and Expansion of Human Colon-Cancer-Initiating Cells." Nature. 445.7123 (2006):111-115.
Rosen, "The role of constitutively active signal transducer and activator of transcription 3 in ovarian tumorigenesis and prognosis" Cancer (2006) 107(11) 2730-40.
Scheper, "Sulindac induces apoptosis and inhibits tumor growth in vivo in head and neck squamous cell carcinoma" Neoplasia (2007) 9(3): 192-199.
Scholz, "Activated signal transducer and activator of transcription 3 (STAT3) supports the malignant phenotype of human pancreatic cancer" Gastroenterology (2003) 125:891-905.
Silver, "Activated signal transducer and activator of transcription (STAT) 3: localization in focal adhesions and function in ovarian cancer cell motility" Cancer Res. (2004) 15;64(10)3550-8.
Song "A low-molecular-weight compound discovered through virtual database screening inhibits Stat3 function in breast cancer cells." Proc. Natl. Acad Sci.102.13(2005): 4700-4705.
Song, "Activation of Stat3 by receptor tyrosine kinases and cytokines regulates survival in human non-small cell carcinoma cells" Oncogene (2003) 22(27) 4150-65.
Spiekerman, "Constitutive activation of STAT transcription factors in acute myelogenous leukemia" Eur J Haematol (2001) 67: 63-71.
Sun "Comparison of Effects of the Tyrosine Kinase Inhibitors AG957, AG490, and STI571 on BCR-ABL-Expressing Cells, Demonstrating Synergy Between AG490 and STI571." Blood. 97.7(2001):2008-2015.
Tsareva, "Signal transducer and activator of transcription 3 activation promotes invasive growth of colon carcinomasthrough matrix metalloproteinase induction" Neoplasia (2007) 9, 4: 279-291.
Wang Zhianghiga Bins Li Xi.* Za Zhi (V07) 36(6):3Z9-83 (2007) (Abstract).
Wang, "Effect of STAT3 siRNA-induced inhibition of STAT3 gene expression on the growth and apoptosis of lewis lung cancer cells" J. ain. Oncol. (2006) 3: 392-399.
Wermuth "Molecular Variations Based on Isoteric Replacements," the Practice of Medicinal Chemistry, Academic Press, 1996. pp. 203-237.
Williams "Two New Cytotoxic Naphthoquinones from Mendoncia cowanii from the Rainforest of Madagascar." Planta Medica. 72.6(2006):564-566.
Yau "inhibition of Integrin-Linked Kinase by QLT0254 Inhibits Akt-Dependent Pathways and is Growth inhibitory in Orthotopic Primary Pancreatic Cancer Xenografts." Cancer Res. 65.4(2005):1497-1504.
Zani "Furanonaphthoquinones from Tabebuia Ochracea," Phytochernistry, (1991), vol. 30, No. 7, pp. 2379-2331.
Chen, et al., "Constituents of Markharnia hilderbrandtil (Baker" Sprague and their antitumor activity, (SciFinder), 1986.
STN Accession No. 1986 568912.
STN Accession No. 1992:245248.
STN Accession No. 1999:157137.
STN Accession No. 2002:33229.

(56) References Cited

OTHER PUBLICATIONS

Achcar Expression of activated and latent signal transducer and activator of transcription 3 in 303 non-small cell lung carcinomas and 44 malignant mesotheliomas: possible role for chemotherapeutic intervention. Arch Petal Lab Med. (2007) 131(9):1350-60.
Ahmad, Dose translation from animal to human studies revisited, The FASEB Journal, 2007, p. 659.
Alvarez "Identification of a genetic signature of activated signal transducer and activator of transcription 3 in human tumors." Cancer Res. (2005) 15; 65(12):5054-62.
Amin "Selective inhibition of STAT3 induces apoptosis and G(1) cell cycle arrest in ALK-positive anaplastic large cell lymphoma." Oncogene (2004) 23,5426-5434.
Aoki "Inhibition of STAT3 signaling induces apoptosis and decreases survivin expression in primary effusion lymphoma" Blood (2003) 101:1535-1542.
Barton "Signal transducer and activator of transcription 3 (STAT3) activation in prostate cancer: Direct STAT3 Inhibition induces apoptosis in prostate cancer lines." Mot Cancer Ther. (2004) 3(1):11-20.
Benekli "Constitutive activity of signal transducer and activator of transcription 3 protein in acute myeloid leukemia blasts is associated with short disease-free survival." Blood (2002) 99:252-257.
Berishaj "Stat3 is tyrosine-phosphorylated through the interleukin-6/glycoprotein 130/Janus kinase pathway in breast cancer" Breast Cancer Res. (2007) 9(3): R32.
Blaskovich "Discovery of JSI-124 (cucurbitacin I), a selective Janus kinase/signal transducer and activator of transcription 3 signaling pathway inhibitor with potent antitumor activity against human and murine cancer cells in mice" Cancer Res (2003) 63: 1270-1279.
Braatz "Crystallization: Particle Size Control." Encyclopedia of Pharmaceutical Technology. Swarbrick, ed. New York: Informa Healthcare. Third Edition (2007):858-871.
Brittain Polymorphism in Pharmaceutical Solids 1st ed. (1999).
Brittain Polymorphism in Pharmaceutical Solids 2nd ed. (1999).
Byrn Solid-State Chemistry of Drugs, 2d, Chapter 11 hydrates and solvates/hydrates, 233-247 (1999).
Caira, Crystalline Polymorphism of Organic Compounds, Topics in Chemistry, vol. 198 (1998).
Chan "Disruption of Stat3 reveals a critical role in both the initiation and the promotion stages of epithelial carcinogenesis" J. Clin. Invest. (2004) 114: 720-728.
Chang "Activation of STAT3 in thymic epithelial tumours correlates with tumour type and clinical behavior" J Pathol (2006) 210:224-33.
Chen "Signal transducer and activator of transcription 3 is involved in cell growth and survival of human rhabdomyosarcoma and osteosarcoma cells" BMC Cancer (2007) 7:111.
Cho-Vela, "Suppressor of cytokine signaling 3 expression in anaplastic large cell lymphoma" Leukemia (2004) 18,1872-1878.
De Araujo "STAT3 expression in salivary gland tumours" Oral Oncology. (2007); 44(5):439-45.
Diaz "Activation of stat3 in primary tumors from high-risk breast cancer patients is associated with elevated levels of activated SRC and survivin expression" Clin Cancer Research (2006) 1;12(1):20-8.
Fagerholm "Experimental Estimation of the Effective Unstirred Water Layer Thickness in the Human Jejunum, and its Importance in Oral Drug Absorption." Eur. J. Pharm. 3(1995):247-253.
Fotsing "Identification of an Anti-Inflammatory Principle from the Stem Bark of Millettia versicolor", Planta Med, (2003), 69(8) 767-770.
Gafner "Antifungal and Antibacterial Naphthoquinones from Newbouldia laevis Roots." Phytochemistry. 42.5 (1996):1315-1320.
Gao "Inhibition of STAT3 expression by siRNA suppresses growth and induces apoptosis in laryngeal cancer cells." Acta Pharmacol Sin. (2005) 26(3)377-383.
Gao "Knockdown of Stat3 expression using RNAi inhibits growth of laryngeal tumors in vivo" Acta Pharmacol Sin. (2006) 27(3):347-52.
Garcia "Constitutive activation of Stat3 by the Src and JAK tyrosine kinases participates in growth regulation of human breast carcinoma cells" Oncogene (2001) 20(20): 2499-2513.
Garcia "Constitutive activation of Stat3 in fibroblasts transformed by diverse oncoproteins and in breast carcinoma cells." Cell Growth Differ (1997) 8(12):1267-1276.
Goodell "Isolation and Functional Properties of Murine Hematopoietic Stem Cells That are Replicating in Vivo." J. Exp. Med. 183.4(1996)1797-1806.
Gormann "Furanonaphthoquinones, atraric acid and a benzofuran from the stem barks of Newbouldia laevis." Phytochemistry. 64.2(2003):583-587.
Grandis "STAT signaling in head and neck cancer" Oncogene (2000) 15;19(21): 2489-2495.
Gritsko "Persistent activation of stat3 signaling induces survivin gene expression and confers resistance to apoptosis in human breast cancer cells" Clinical Cancer Research (2006) 12(1): 11-19.
Haleblian "Pharmaceutical applications of polymorphism" J. Pharm. Sci. Aug. 1969, p. 911.
Han Li., "Unusual naphthoquinone derivatives from the twigs of Avicennia marina" J. Nat. Prod. (2007) 70, 923-927.
Haraguchi "Characterization of a Side Population of Cancer Cells From Human Gastrointestinal System." Stem Cells, 24.3(2005):506-513.
Haura "Activated epidermal growth factor receptor-Stat-3 signaling promotes tumor survival in vivo in non-small cell lung cancer" Clin Cancer Res (2005) 11(23) 8288-94.
Holtick "STAT3 is essential for Hodgkin lymphoma cell proliferation and is a target of tyrphostin AG17 which confers sensitization for apoptosis" Leukemia. (2005) 19 (6):936-44.
Horiguchi "Activation of signal transducer and activator of transcription 3 in renal cell carcinoma: a study of incidence and its association with pathological features and clinical outcome" The Journal of Urology (2002) 168 (2):762-765.
Hsiao "Constitutive activation of STAT3 and STAT5 is present in the majority of nasopharyngeal carcinoma and correlates with better prognosis." Br J Cancer. (2003) 21;89 (4344-9).
Huang "Constitutive activation of stat 3 oncogene product in human ovarian carcinoma cells" Gynecol Oncol. (2000) 79(1):67-73.
Itoh "Requirement of STAT3 activation for maximal collagenase-1 (MMP-1) induction by epidermal growth factor and malignant characteristics in T24 bladder cancer cells." Oncogene (2006) 25, 1195-1204.
Itoigawa "Cancer chemopreventive activity of naphthoquinones and their analogs from Avicennia plants." Cancer Letters. 174. 2(2001):135-139.
Johnson "Abrogation of Signal Transducer and Activator of Transcription 3 Reactivation After Src Kinase Inhibition Results in Synergistic Antitumor Effects." Clin. Cancer Res. 13.14(2007):4233-4244.
Kijima "STAT3 activation abrogates growth factor dependence and contributes to head and neck squamous cell carcinoma tumor growth in vivo" Cell Growth Diff. (2002) 13: 355-362.
Kim "Inhibition of signal transducer and activator of transcription 3 activity results in down-regulation of Survivin following irradiation" Mol. Cancer Thera. 5.11(2006):2659-2665.
Konnikova, "Knockdown of STAT3 expression by RNAi induces apoptosis in astrocytoma cells" BMC Cancer (2003) 3:23.
Koyanagi "A Facile Synthesis of 2-Acteylnaphtho[2,3-b]furan-4,9-dione," Journal of Heterocyclic Chemistry, (1995), vol. 32, pp. 1289-1291.

\* cited by examiner

A.

EMSA

B.

Western Blotting (-) Verapamil (+) Verapamil

DU145 Cells - 5 Hour treatment

GROUP OF STAT3 PATHWAY INHIBITORS AND CANCER STEM CELL PATHWAY INHIBITORS

REFERENCE TO RELATED APPLICATIONS

This application claims priority to and the benefit of U.S. provisional patent application Nos. 60/971,144 and 61/013,372, respectively filed on Sep. 10, 2007 and Dec. 13, 2007, the entire contents of which applications are incorporated herein by reference.

FIELD OF THE INVENTION

The present invention relates generally to the use of Stat3 pathway inhibitors to treat conditions. More specifically, the invention relates to the use of Stat3 pathway inhibitors to target cancer stem cells and to treat other disorders. Even more specifically, the invention relates to the use of naphtho[2,3-b]furan-4,9-dione and related compounds to inhibit Stat3, to target cancer stem cells, and to treat malignant diseases. The invention also relates to treatment for refractory, recurrent, or metastatic cancers, and to processes for preparing relevant compounds and intermediates thereof, and to pharmaceutical composition of relevant compounds.

BACKGROUND OF THE INVENTION

Cancer Stem Cells (CSCs).

In recent years, a new model of tumorigenesis has gained wide acceptance, where it is hypothesized that only a small fraction of the entire tumor mass are responsible for the tumorigenic activities within the tumor, whereas the old or clonal genetic model posits that all the mutated tumor cells contribute equally to such tumorigenic activities. This small fraction of tumorigenic cells, according to the new model, are transformed cells with stem-cell-like qualities and are called "cancer stem cells" (CSCs). Bonnet and Dick first demonstrated, in vivo, the presence of CSCs in acute myeloid leukemia (AML) during the 1990s. Their data showed that only a small subpopulation of human AML cells had the ability to transfer AML when transplanted into immunodeficient mice while other AML cells were incapable of inducing leukemia. Later, these CSCs were shown to have the same cellular markers, $CD34^+/CD38^-$, as primitive hematopoietic stem cells [1]. Since then, researchers have found CSCs conclusively in various types of tumors including those of the brain, breast, skin, prostate, and so on.

The CSC model of tumorigenesis would explain why tens or hundreds of thousands of tumor cells need to be injected into an experimental animal in order to establish a tumor transplant. In human AML, the frequency of these cells is less than 1 in 10,000 [2]. Even though rare within a given tumor cell population, there is mounting evidence that such cells exist in almost all tumor types. However, as cancer cell lines are selected from a subpopulation of cancer cells that are specifically adapted to grow in tissue culture, the biological and functional properties of cancer cell lines can undergo dramatic changes. Therefore, not all cancer cell lines contain CSCs.

Cancer stem cells share many similar traits with normal stem cells. For example, CSCs have self-renewal capacity, namely, the ability to give rise to additional tumorigenic cancer stem cells, typically at a slower rate than other dividing tumor cells, as opposed to a limited number of divisions. CSCs also have the ability to differentiate into multiple cell types, which would explain histological evidence that not only many tumors contain multiple cell types native to the host organ, but also that heterogeneity is commonly retained in tumor metastases. CSCs have been demonstrated to be fundamentally responsible for tumorigenesis, cancer metastasis, and cancer reoccurrence. CSCs are also called tumor initiating cells, cancer stem-like cells, stem-like cancer cells, highly tumorigenic cells, tumor stem cells, solid tumor stem cells, or super malignant cells.

The existence of cancer stem cells has fundamental implications for future cancer treatments and therapies. These implications are manifested in disease identification, selective drug targeting, prevention of cancer metastasis and recurrence, and development of new strategies in fighting cancer.

The efficacy of current cancer treatments are, in the initial stages of testing, often measured by the size of the tumor shrinkage, i.e., the amount of tumor mass that is killed off. As CSCs would form a very small proportion of the tumor and have markedly different biologic characteristics than their more differentiated progenies, the measurement of tumor mass may not necessarily select for drugs that act specifically on the stem cells. In fact, cancer stem cells appear to be resistant to radiotherapy (XRT) and also refractory to chemotherapeutic and targeted drugs [3-5]. Normal somatic stem cells are naturally resistant to chemotherapeutic agents—they have various pumps (such as MDR) that pump out drugs, and DNA repair proteins. Further, they also have a slow rate of cell turnover while chemotherapeutic agents target rapidly replicating cells. Cancer stem cells, being the mutated counterparts of normal stem cells, may also have similar mechanisms that allow them to survive drug therapies and radiation treatment. In other words, conventional chemotherapies and radiotherapies kill differentiated or differentiating cells, which form the bulk of the tumor that are unable to generate new highly tumorigenic cancer stem cells. The population of cancer stem cells that gave rise to the differentiated and differentiating cells, on the other hand, could remain untouched and cause a relapse of the disease. A further danger for conventional anti-cancer therapy is the possibility that chemotherapeutic treatment leaves only chemotherapy-resistant cancer stem cells, and the ensuing recurrent tumor will likely also be resistant to chemotherapy.

Since the surviving cancer stem cells can repopulate the tumor and cause relapse, it is imperative that anti-cancer therapies include strategies against CSCs (see FIG. 1). This is akin to eliminating the roots in order to prevent dandelions from regrowth even if the weed's ground level mass has been cut [6]. By selectively targeting cancer stem cells, it becomes possible to treat patients with aggressive, non-resectable tumors and refractory or recurrent cancers, as well as preventing the tumor metastasis and recurrence. Development of specific therapies targeting cancer stem cells may improve survival and the quality of life of cancer patients, especially for sufferers of metastatic cancers. The key to unlocking this untapped potential is the identification and validation of pathways that are selectively important for cancer stem cell self-renewal and survival. Unfortunately, though multiple pathways underlying tumorigenesis in cancer or self-renewal in embryonic and adult stem cells have been elucidated in the past, no pathways have been identified and validated for cancer stem cell self-renewal and survival.

There has also been a lot of research into the identification and isolation of cancer stem cells. Methods used mainly exploit the ability of CSCs to efflux drugs, or are based on the expression of surface markers associated with cancer stem cells.

For example, since CSCs are resistant to many chemotherapeutic agents, it is not surprising that CSCs almost ubiquitously overexpress drug efflux pumps such as ABCG2 (BCRP-1) [7-11], and other ATP binding cassette (ABC) superfamily members [12, 13]. Accordingly, the side population (SP) technique, originally used to enrich hematopoetic and leukemic stem cells, was also employed to identify and isolate CSCs [14]. This technique, first described by Goodell et al., takes advantage of differential ABC transporter-dependent efflux of fluorescent dyes such as Hoechst 33342 to define and isolate a cell population enriched in CSCs [10, 15]. Specifically, the SP is revealed by blocking drug efflux with verapamil, at which point the dyes can no longer be pumped out of the SP.

Researchers have also focused on finding specific markers that distinguish cancer stem cells from the bulk of the tumor. Most commonly expressed surface markers by the cancer stem cells include CD44, CD133, and CD166 [16-22]. Sorting tumor cells based primarily upon the differential expression of these surface marker(s) have accounted for the majority of the highly tumorigenic CSCs described to date. Therefore, these surface markers are well validated for identification and isolation of cancer stem cells from the cancer cell lines and from the bulk of tumor tissues.

Stat3 Pathway.

There are many different genetic defects in mammalian or human cancer cells, and many have been studied in the quest to cure cancer. For example, the p53 tumor suppressor has been found to be defective or altogether absent in more than half of the human cancers. The STAT (Signal Transducers and Activator of Transcription) protein family are latent transcription factors activated in response to cytokines/growth factors to promote proliferation, survival, and other biological processes. Among them, Stat3 is activated by phosphorylation of a critical tyrosine residue mediated by growth factor receptor tyrosine kinases, Janus kinases, or the Src family kinases, etc. These kinases include, but are not limited to EGFR, JAKs, Abl, KDR, c-Met, Src, and Her2 [23]. Upon tyrosine phosphorylation, Stat3 forms homodimers, translocates to the nucleus, binds to specific DNA-response elements in the promoter regions of the target genes, and induces gene expression [24].

In normal cells, Stat3 activation is transient and tightly regulated, lasting from 30 minutes to several hours. However, Stat3 is found to be aberrantly active in a wide variety of human cancers, including all the major carcinomas as well as some hematologic tumors. Stat3 plays multiple roles in cancer progression. As a potent transcription regulator, it targets genes involved in many important cellular functions, such as Bcl-xl, c-Myc, cyclin D1, Vegf, MMP-2, and survivin [25-30]. It is also a key negative regulator of tumor immune surveillance and immune cell recruitment [31-33].

Ablating Stat3 signaling by antisense, siRNA, a dominant-negative form of Stat3, and/or blockade of tyrosine kinases inhibits certain cancer cell lines or tumors in vitro and/or in vivo [24, 26, 34, 35]. But no clear link between Stat3 and cancer stem cell functionality has ever been empirically made. Nor have researchers found an effective Stat3 pathway inhibitor to explore potential therapeutic uses with regard to cancers that have been found to contain cancer stem cells. As described earlier, cancer stem cells (CSCs) have been recently demonstrated to be fundamentally responsible for tumorigenesis, metastasis, and reoccurrence, and should be taken into consideration in designing any curative therapy that targets a tumor known to have these cells no matter how small a fraction of the tumor mass they may constitute.

In diseases other than cancer, over-activation of Stat3 by Interleukin 6 (IL6) has been demonstrated in a number of autoimmune and inflammatory diseases [36]. Recently, it has been revealed that the Stat3 pathway also promotes pathologic immune responses through its essential role in generating TH17 T cell responses [37]. In addition, IL6-Stat3 pathway mediated inflammation has been found to be the common causative origin for atherosclerosis, peripheral vascular disease, coronary artery disease, hypertension, osteroprorosis, type 2 diabetes, and dementia.

SUMMARY

The present invention is predicated, in part, on empirical evidence provided herein that Stat3 plays a key role in both the survival and self-renewal capacity of cancer stem cells (CSCs) across a broad spectrum of cancers. Accordingly, a first aspect of the invention is directed to a method of inhibiting a cancer stem cell where the method comprises inhibiting at least some, most, or substantially all (e.g., 30%, 40%, 50%, 60%, 70%, 80%, 90%, or 95%), of the Stat3 pathway activity in the cancer stem cell through a Stat3 pathway inhibitor. The method inhibits the CSC from self-renewal or kills the CSC. The method can be carried out in vitro, or in vivo to treat a cancer, especially cancers that have CSCs and have aberrant, e.g., overactive Stat3 pathway activities. These two criteria can be met by virtue of institutional knowledge, i.e., the patient's cancer is of a type known to have CSCs and aberrant Stat3 pathway activities, or can be confirmed from the individual patient, e.g., through tests conducted on a biopsy. In a preferred embodiment, the CSCs are known or otherwise confirmed to have aberrant Stat3 pathway activities.

Cancers that are currently known to have both CSCs and aberrant Stat3 pathway activities include and are not limited to: breast cancer, head and neck cancer, lung cancer, ovarian cancer, pancreatic cancer, colorectal carcinoma, prostate cancer, melanoma, sarcoma, liver cancer, brain tumors, multiple myeloma, and leukemia. Many of the metastatic forms of these cancers have also been found to have both CSCs and aberrant Stat3 pathway activities, such as metastatic breast cancer. In one feature, methods of the present invention can be practiced to treat a cancer selected from this group. In one embodiment, methods of the invention can be practiced to treat a cancer selected from the following: lung cancer, breast cancer, cervical cancer, colorectal carcinoma, liver cancer, head and neck cancer, pancreatic cancer, gastric cancer, and prostate cancer.

Further, as CSCs have been demonstrated to be fundamentally responsible for tumorigenesis, cancer metastasis and cancer reoccurrence, methods of the invention can be practiced to treat cancer that is metastatic, refractory to a chemotherapy or radiotherapy, inherently resistant to chemotherapy or has relapsed in the subject after an initial treatment. In one embodiment, the Stat3 pathway inhibitor is isolated, purified or synthetic, and can be selected from the group consisting of a small molecule Stat3 inhibitor, an RNAi agent against Stat3, an antisense agent against Stat3, a peptidomimetic Stat3 inhibitor, and a G-quartet oligodeoxynucleotide Stat3 inhibitor. The mechanism of inhibition can be selected from the group consisting of substantially inhibiting phosphorylation of the Stat3 protein, substantially inhibiting dimerization of the Stat3 protein, substantially inhibiting nuclear translocation of the Stat3 protein, substantially inhibiting DNA-binding activity of the Stat3 protein, and substantially inhibiting transcription activities of the Stat3 protein.

In one embodiment, the inhibitor is a compound selected from the group consisting of 2-(1-hydroxyethyl)-naphtho[2,3-b]furan-4,9-dione, 2-acetyl-7-chloro-naphtho[2,3-b]furan-4,9-dione, 2-acetyl-7-fluoro-naphtho[2,3-b]furan-4,9-dione, 2-acetylnaphtho[2,3-b]furan-4,9-dione, 2-ethyl-naphtho[2,3-b]furan-4,9-dione, phosphoric acid mono-[1-(4,9-dioxo-3a,4,9,9a-tetrahydro-naphtho[2,3-b]furan-2-yl)-vinyl]ester, phosphoric acid 1-(4,9-dioxo-3a,4,9,9a-tetrahydro-naphtho[2,3-b]furan-2-yl)-vinyl ester dimethyl ester, an enantiomer, diastereomer, tautomer, and a salt or solvate thereof (hereafter referred to as the "Compound of the Invention").

In a second aspect, the present invention provides a method of inhibiting cellular Stat3 pathway activity in a cell. The method includes administering to the cell an effective amount of the Compound of the Invention such that at least unwanted Stat3 pathway activity in the cell is reduced, for example, by at least 20%, 30%, 40%, 50%, 60%, 70%, 80%, 90% or 95%. In one embodiment, the cell is a CSC, or otherwise cancerous. The method may induce cell death or inhibit self-renewal in the cell. The method can be carried out in vitro or in vivo.

In a third aspect, the present invention provides a method of treating or preventing a disorder associated with aberrant Stat3 pathway activity in a subject, the method comprising administering to the subject a therapeutically effective amount of a pharmaceutical composition comprising the Compound of the Invention such that at least aberrant Stat3 pathway activity is reduced. In one feature, aberrant Stat3 pathway activity can be identified by expression of phosphorylated Stat3 or a surrogate upstream or downstream regulator of Stat3 phosphorylation. The disorder can be a cancer. In one embodiment, the cancer is known to have aberrant Stat3 pathway activities, and include but are not limited to: breast cancer, head and neck cancer, lung cancer, ovarian cancer, pancreatic cancer, colorectal carcinoma, prostate cancer, renal cell carcinoma, melanoma, hepatocellular carcinomas, cervical cancer, sarcomas, brain tumors, gastric cancers, multiple myeloma, leukemia, and lymphomas. The disorder may also be a non-cancerous condition known to be associated with aberrant Stat3 pathway activity, and in one embodiment, is selected from the group consisting of an autoimmune disease, an inflammatory disease, inflammatory bowel diseases, arthritis, autoimmune demyelination disorder, Alzheimer's disease, stroke, ischemia reperfusion injury, and multiple sclerosis.

In a fourth aspect, the present invention provides a method of treating a patient and includes the steps of identifying a patient by aberrant Stat3 pathway activity and administering to the patient a therapeutically effective amount of the Compound of the Invention. In one embodiment, the step of identifying the patient by aberrant Stat3 pathway activity comprises testing expression of phosphorylated Stat3 or of a surrogate upstream or downstream regulator of Stat3 phosphorylation. The step of identifying the patient by aberrant Stat3 pathway activity may comprise testing diseased tissue or fluid taken from the patient, which may be part of a tumor.

In a fifth aspect, the present invention provides a method of treating a patient and includes the steps of identifying a patient diagnosed with a disorder associated with aberrant Stat3 pathway activity and administering to the patient a therapeutically effective amount of the Compound of the Invention. In one embodiment, the step of identifying the patient comprises testing for at least one biomarker that indicates the disorder in the patient.

In a sixth aspect, the present invention provides a kit that includes at least one agent for diagnosing a disorder associated with aberrant Stat3 pathway activity, which can be testing for a biomarker that indicates the presence of the disorder, and a therapeutically effective amount of the Compound of the Invention.

In a seventh aspect, the present invention provides a kit that includes at least one agent for diagnosing aberrant Stat3 pathway activity, and a therapeutically effective amount of the Compound of the Invention. In one embodiment, the agent tests the expression of phosphorylated Stat3 or of a surrogate upstream or downstream regulator of Stat3 phosphorylation.

In an eighth aspect, the present invention provides a method of inhibiting one or more cancer stem cells. The method includes administering to the cancer stem cell an effective amount of the Compound of the Invention. The method can be carried out in vitro or in vivo to treat a cancer in a subject. In one embodiment, the cancer is known to have CSCs, and include but are not limited to: breast cancer, head and neck cancer, lung cancer, ovarian cancer, pancreatic cancer, colorectal carcinoma, prostate cancer, liver cancer, melanoma, multiple myeloma, brain tumors, sarcomas, medulloblastoma, and leukemia. In one embodiment, the cancer is metastatic. In another embodiment, the cancer is refractory to a chemotherapy or radiotherapy. For example, the cancer can be inherently resistant to chemotherapy. In yet another embodiment, the cancer has relapsed in the subject after an initial treatment.

In a ninth aspect, the present invention provides a method of identifying a drug candidate capable of inhibiting a cancer stem cell, the method comprising screening for a drug candidate that inhibits Stat3 pathway activity. The drug candidate, in one embodiment, is capable of inducing cell death in the cancer stem cell, and in another embodiment, of inhibiting self-renewal of the CSC. In various embodiments, the drug candidate is a small molecule Stat3 inhibitor, an RNAi agent against Stat3, an antisense agent against Stat3, a peptidomimetic Stat3 inhibitor, or a G-quartet oligodeoxynucleotides Stat3 inhibitor. The drug candidate may have the capacity selected from the following: substantially inhibiting phosphorylation of the Stat3 protein, substantially inhibiting dimerization of the Stat3 protein, substantially inhibiting nuclear translocation of the Stat3 protein, substantially inhibiting DNA-binding activity of the Stat3 protein, and substantially inhibiting transcription activities of the Stat3 protein In a tenth aspect, the present invention provides a method of treating a subject for cancer refractory to a standard treatment, the method comprising administering to the subject a therapeutically effective amount of a pharmaceutical composition comprising the Compound of the Invention. The standard treatment can be, for example, a chemotherapy, a radiotherapy, and/or surgery. In one embodiment, the cancer is inherently resistant to chemotherapy.

In an eleventh aspect, the present invention provides a method of treating or preventing cancer relapse in a subject, the method comprising administering to the subject a therapeutically effective amount of a pharmaceutical composition comprising the Compound of the Invention. In one embodiment, the pharmaceutical composition is administered as an adjuvant therapy after surgery.

In a twelfth aspect, the present invention provides a method of treating or preventing cancer metastasis in a subject, the method comprising administering to the subject a therapeutically effective amount of a pharmaceutical composition comprising the Compound of the Invention. In one embodiment, the pharmaceutical composition is administered as an adjuvant therapy after surgery.

In a thirteenth aspect, the present invention provides a method of selectively targeting cancer cells in a subject, e.g., for treating a malignant disease, the method comprising administering to a subject a pharmaceutical composition comprising the Compound of the Invention, such that the compound concentration in the subject's plasma is not maintained above a critical concentration for more than 24 hour after each dose, thereby selectively killing cancer cells while substantially sparing normal cells. Alternatively, according to the inventive method, the compound plasma concentration is not above the critical concentration at a certain time point after each dose, e.g., 12, 16, 20 or 24 hours. In one embodiment, the pharmaceutical composition is administered such that the compound concentration in the subject's plasma is not maintained above a critical concentration, e.g., continuously, for more than a duration selected from the group consisting of 12, 16, and 20 hours after each dose. In various embodiments, the critical concentration is about 100 µM, about 50 µM, about 30 µM, or about 20 µM. In one embodiment, the cancer cells are part of a cancer selected from the group, or any of its subgroup, consisting of liver cancer, head and neck cancer, pancreatic cancer, gastric cancer, renal cancer, sarcoma, multiple myeloma, metastatic breast cancer, leukemia, lymphoma, esophageal cancer, brain tumor, glioma, bladder cancer, endometrial cancer, thyroid cancer, bile duct cancer, bone cancer, eye cancer (retinoblastoma), gallbladder cancer, pituitary cancer, rectal cancer, salivary gland cancer, nasal pharyngeal cancer, breast cancer, lung cancer, colon cancer, prostate cancer, ovarian cancer, neuroblastoma, cervix cancer, leukemia, melanoma, oral epithermoid, keratinocyte, and skin cancer. In another embodiment, the cancer cells are part of a cancer selected from the group consisting of lung cancer, breast cancer (including the metastatic kind), cervical cancer, colorectal carcinoma, liver cancer, head and neck cancer, pancreatic cancer, gastric cancer, and prostate cancer.

In a fourteenth aspect, the present invention provides a method of treating cancer in a subject, the method comprising administering to the subject a therapeutically effective amount of a pharmaceutical composition comprising the Compound of the Invention. Methods according to this aspect of the invention can be applied to treat cancer similar to those described with regard to previous aspects of the invention. In one feature, the subject of the treatment is a mammal, e.g., a human.

In a fifteenth aspect, the present invention provides a pharmaceutical composition that comprises the Compound of the Invention, i.e., a compound selected from the group consisting of 2-(1-hydroxyethyl)-naphtho[2,3-b]furan-4,9-dione, 2-acetyl-7-chloro-naphtho[2,3-b]furan-4,9-dione, 2-acetyl-7-fluoro-naphtho[2,3-b]furan-4,9-dione, 2-acetyl-naphtho[2,3-b]furan-4,9-dione, 2-ethyl-naphtho[2,3-b]furan-4,9-dione, phosphoric acid mono-[1-(4,9-dioxo-3a,4,9,9a-tetrahydro-naphtho[2,3-b]furan-2-yl)-vinyl]ester, phosphoric acid 1-(4,9-dioxo-3a,4,9,9a-tetrahydro-naphtho[2,3-b]furan-2-yl)-vinyl ester dimethyl ester, and a pharmaceutically acceptable salt or solvate thereof, and a pharmaceutically-acceptable excipient, carrier, or diluent. In one feature, the composition is suitable for oral, nasal, topical, rectal, vaginal or parenteral administration, or intravenous, subcutaneous or intramuscular injection.

In a sixteenth aspect, the present invention also provides a process of preparing some of the Compounds of the Invention. The method prepares a compound of formula 4-6,

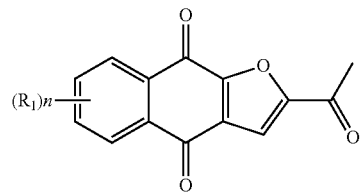

(4-6)

wherein $R_1$ is H, Cl, or F, by reacting a compound of formula 4-4,

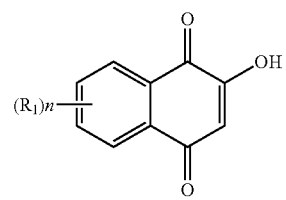

(4-4)

with a ketone in a solvent while in the presence of a base and an oxidizing agent. The oxidizing agent can be, for example, $O_2$, $Br_2$ or $CBrCl_3$. In one embodiment, the reaction is carried out in an open air container. In one feature, all the steps of the process take place in one pot, i.e., in the same container. In various exemplary embodiments, the solvent may be tetrahydrofuran (THF), dioxane, or toluene, and the base may be 1,8-diazabicyclo[5.4.0]undec-7-ene (DBU), triethyl amine, or diisopropylethyl amine.

In an embodiment of the above process, the ketone is a compound of formula 4-3.

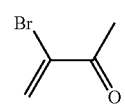

(4-3)

The above process can further include the following steps: reacting a compound of formula 4-1,

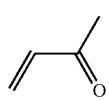

(4-1)

with bromide with or without solvent to produce a compound of formula 4-2,

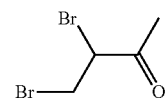

(4-2)

and subsequently reacting the compound of formula 4-2 in a solvent in the presence of a base to produce the compound of formula 4-3.

(4-3)

In a seventeenth aspect, the present invention provides a compound of the formula phosphoric acid mono-[1-(4,9-dioxo-3a,4,9,9a-tetrahydro-naphtho[2,3-b]furan-2-yl)-vinyl]ester.

In an eighteenth aspect, the present invention provides a compound of the formula phosphoric acid 1-(4,9-dioxo-3a,4,9,9a-tetrahydro-naphtho[2,3-b]furan-2-yl)-vinyl ester dimethyl ester.

In a nineteenth aspect, the present invention provides a process of preparing the compound phosphoric acid mono-[1-(4,9-dioxo-3a,4,9,9a-tetrahydro-naphtho[2,3-b]furan-2-yl)-vinyl]ester, the process comprising reacting compound 2-acetylnaphtho[2,3-b]furan-4,9-dione with a solution selected from the group consisting of lithium bis(trimethylsilyl)amide, sodium bis(trimethylsilyl)amide, and potassium bis(trimethylsilyl)amid, followed with adding a solution of dimethyl chlorophosphate. The process may further comprise purifying a crude product obtained from the reaction by dissolving the product in $CH_2Cl_2$, washing it with saturated $NH_4CL$ and water, drying it over $MgSO_2$, and subsequently running the product through column chromatography.

In a twentieth aspect, the present invention provides a process of preparing the compound phosphoric acid 1-(4,9-dioxo-3a,4,9,9a-tetrahydro-naphtho[2,3-b]furan-2-yl)-vinyl ester dimethyl ester, the process comprising reacting compound phosphoric acid mono-[1-(4,9-dioxo-3a,4,9,9a-tetrahydro-naphtho[2,3-b]furan-2-yl)-vinyl]ester with trimethylsilyl bromide. The process can further comprise purifying a crude product obtained from the reaction by a semi-prep-HPLC.

Other aspects and embodiments of the present invention are set forth or will be readily apparent from the following detailed description of the invention.

DETAILED DESCRIPTION

Figure 1:
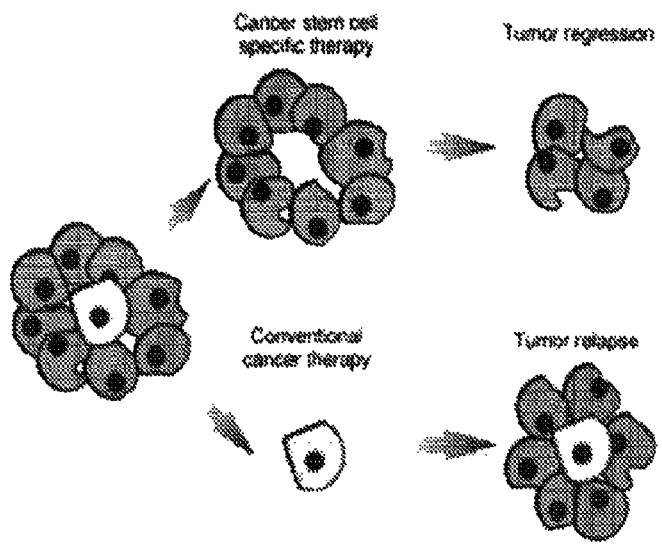
FIG. 1 illustrates the differences between cancer-stem-cell-specific and conventional cancer therapies.

As used herein, the singular form "a", "an", and "the" include plural references unless the context clearly dictate otherwise. For example, the term "a cell" includes a plurality of cells including mixtures thereof.

The terms "isolated" or "purified" as used herein refer to a material that is substantially or essentially free from components that normally accompany it in its native state. Purity and homogeneity are typically determined using analytical chemistry techniques such as polyacrylamide gel electrophoresis or high performance liquid chromatography.

As used herein, the terms "cancer stem cell(s)" and "CSC(s)" are interchangeable. CSCs are mammalian, and in preferred embodiments, these CSCs are of human origin, but they are not intended to be limited thereto. Cancer stem cells are defined and functionally characterized as a population of cells originating from a solid tumor that: (1) have extensive proliferative capacity; 2) are capable of asymmetric cell division to generate one or more kinds of differentiated progeny with reduced proliferative or developmental potential; and (3) are capable of symmetric cell divisions for self-renewal or self-maintenance. Other common approaches to characterize CSCs involve morphology and examination of cell surface markers, transcriptional profile, and drug response. CSCs are also called in the research literature tumor/cancer initiating cells, cancer stem-like cells, stem-like cancer cells, highly tumorigenic cells, tumor stem cells, solid tumor stem cells, drug survival cells (DSC), drug resistant cells (DRCs) or super malignant cells.

As used herein, the term "self-renewal" refers to cancer stem cells' ability to give rise to new tumorigenic cancer stem cells to replenish or increase their number.

As used herein, the terms "cancer" and "cancerous" refer to or describe the physiological condition in mammals in which a population of cells are characterized by unregulated cell growth. "Cancer cells" and "tumor cells" as used herein refer to the total population of cells derived from a tumor including both non-tumorigenic cells, which comprise the bulk of the tumor cell population, and tumorigenic stem cells (cancer stem cells). Examples of cancer include, but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancer.

"Tumor" as used herein refers to any mass of tissue that result from excessive cell growth or proliferation, either benign (noncancerous) or malignant (cancerous) including pre-cancerous lesions.

"Metastasis" as used herein refers to the process by which a cancer spreads or transfers from the site of origin to other regions of the body with the development of a similar cancerous lesion at the new location. A "metastatic" or "metastasizing" cell is one that loses adhesive contacts with neighboring cells and migrates via the bloodstream or lymph from the primary site of disease to invade neighboring body structures.

As used herein, the term "subject" refers to any animal (e.g., a mammal), including, but not limited to humans, non-human primates, rodents, and the like, which is to be the recipient of a particular treatment. Typically, the terms "subject" and "patient" are used interchangeably herein in reference to a human subject.

Terms such as "treating" or "treatment" or "to treat" or "alleviating" or "to alleviate" as used herein refer to both 1) therapeutic measures that cure, slow down, lessen symptoms of, and/or halt progression of a diagnosed pathologic condition or disorder and 2) prophylactic or preventative measures that prevent or slow the development of a targeted pathologic condition or disorder. Thus those in need of treatment include those already with the disorder; those prone to have the disorder; and those in whom the disorder is to be prevented. A subject is successfully "treated" according to the methods of the present invention if the patient shows one or more of the following: a reduction in the number of or complete absence of cancer cells; a reduction in the tumor size; inhibition of or an absence of cancer cell infiltration into peripheral organs including the spread of cancer into soft tissue and bone; inhibition of or an absence of tumor metastasis; inhibition or an absence of tumor growth; relief of one or more symptoms associated with the specific cancer; reduced morbidity and mortality; and improvement in quality of life.

As used herein, the term "inhibiting", "to inhibit" and their grammatical equivalents, when used in the context of a bioactivity, refer to a down-regulation of the bioactivity, which may reduce or eliminate the targeted function, such as the production of a protein or the phosphorylation of a molecule. In particular embodiments, inhibition may refers to a reduction of about 20%, 30%, 40%, 50%, 60%, 70%, 80%, 90% or 95% of the targeted activity. When used in the context of a disorder or disease, the terms refer to success at preventing the onset of symptoms, alleviating symptoms, or eliminating the disease, condition or disorder.

The term "pharmaceutically-acceptable excipient, carrier, or diluent" as used herein means a pharmaceutically-acceptable material, composition or vehicle, such as a liquid or solid filler, diluent, excipient, solvent or encapsulating material, involved in carrying or transporting the subject pharmaceutical agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations. Wetting agents, emulsifiers and lubricants, such as sodium lauryl sulfate, magnesium stearate, and polyethylene oxide-polypropylene oxide copolymer as well as coloring agents, release agents, coating agents, sweetening, flavoring and perfuming agents, preservatives and antioxidants can also be present in the compositions.

The compounds of the present invention may form salts which are also within the scope of this invention. Reference to a compound of the present invention herein is understood to include reference to salts thereof, unless otherwise indicated. The term "salt(s)", as employed herein, denotes acidic and/or basic salts formed with inorganic and/or organic acids and bases. In addition, when a compound of the present invention contains both a basic moiety, such as but not limited to a pyridine or imidazole, and an acidic moiety such as but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds of the present invention may be formed, for example, by reacting a compound I, II or III with an amount of acid or base, such as an equivalent amount, in a medium such as one in which the salt precipitates or in an aqueous medium followed by lyophilization.

Solvates of the compounds of the invention are also contemplated herein. Solvates of the compounds of the present invention include, for example, hydrates.

Recent studies have uncovered the presence of cancer stem cells (CSCs) with an exclusive ability to regenerate tumors. These CSCs exist in almost all tumor types and are functionally linked with continued malignant growth, cancer metastasis, recurrence, and cancer drug resistance. CSCs and their more differentiated progenies appear to have markedly different biologic characteristics. Conventional cancer drug screenings depend on measurement of the amount of tumor mass, therefore, they may not necessarily select for drugs that act specifically on the CSCs. In fact, CSCs have been demonstrated to resistant to standard chemotherapies and radiotherapy, and to becoming enriched after standard anti-cancer treatments, which result in cancer refractory and recurrence. Methods of isolating these cells include but not limited to identification by their ability of efflux Hoechst 33342, identification by the surface markers these cells express, such as CD133, CD44, CD166, and others, and enrichment by their tumorigenic property. The mounting evidence linking cancer stem cells to tumorigenesis unravel enormous therapeutic opportunity of targeting cancer stem cells.

The key to unlocking this untapped potential is the identification and validation of pathways that are selectively important for CSC self-renewal and survival. Though multiple pathways underlying tumorigenesis in cancer and in embryonic stem cells or adult stem cells have been elucidated in the past, no pathway have been identified and validated for CSC self-renewal and survival.

The present invention provides evidence that Stat3 pathway activity is critical for both CSC's survival and self-renewal (Example 1). The present invention further provides compounds that are effective inhibitors of Stat3 pathway activities (Example 2). The present invention also provides both in vitro and in vivo data that these Stat3 inhibitors do inhibit CSCs' self-renewal and are apoptotic to CSCs (Example 3). The present invention also shows that these compounds can selectively kill a broad spectrum of cancer cells in vitro (Example 4) and inhibit a similarly broad range of cancers in vivo (Example 5). Moreover, the present invention empirically confirms Stat3 inhibitors' efficacy against metastatic cancer (Example 6). Furthermore, the present invention empirically confirms that these compounds can achieve a desired PK exposure for selective killing of cancer cells in vivo (Example 7).

The data provided herein, combined with recent breakthroughs in CSC research, allows the present invention to provide an array of methods directed at inhibiting CSCs, or treating cancers that have CSCs in specific or cancers in general. Also provided herein are methods directed at inhibiting Stat3 pathway activity in cells, or treating disorders, both cancerous and non-cancerous, that are associated with aberrant Stat3 pathway activities. The present invention also provides related methods (e.g., manufacturing and drug candidate screening), materials, compositions and kits.

With the finding that down-regulating or blocking the Stat3 pathway inhibits both self-renewal and survival of CSCs (Example 1), the present invention provides a method of inhibiting cancer stem cells where at least some Stat3 pathway activity in the CSCs are inhibited through a Stat3 pathway inhibitor. In one embodiment, most, i.e., more than 50%, of the Stat3 pathway activity is inhibited. In another embodiment, substantially all of the Stat3 pathway activity is inhibited. The method can prevent the CSCs from self-renewal, such that it is no longer able to replenish its numbers by dividing into tumorigenic CSC cells. Or, the method can induce cell death in CSCs.

This method can be used to treat a subject's cancer. Cancers that are known to have CSCs and aberrant (e.g., overactive or constituently active) Stat3 pathway activities are good candidates for such treatment, and include but are not limited to: breast cancer, head and neck cancer, lung cancer, ovarian cancer, pancreatic cancer, colorectal carcinoma, prostate cancer, renal cell carcinoma, melanoma, hepatocellular carcinomas, cervical cancer, sarcomas, brain tumors, gastric cancers, multiple myeloma, leukemia, and lymphomas. In an embodiment, the method is used to treat liver cancers, head and neck cancers, pancreatic cancers, and/or gastric cancers. In another embodiment, the method is used to treat multiple myeloma, brain tumors, and sarcomas.

Further, as CSCs have been demonstrated to be fundamentally responsible for tumorigenesis, cancer metastasis and cancer reoccurrence, any methods of the invention directed to inhibiting CSCs can be practiced to treat cancer that is metastatic, refractory to a chemotherapy or radiotherapy, or has relapsed in the subject after an initial treatment.

In one embodiment, the inhibitor is isolated, purified or synthetic, and can be selected from the group consisting of a small molecule Stat3 inhibitor, an RNAi agent against Stat3, an antisense agent against Stat3, a peptidomimetic Stat3 inhibitor, and a G-quartet oligodeoxynucleotides Stat3 inhibitor. The inhibitor may be isolated or purified from a natural product as well.

The mechanism of inhibition can be selected to target any step in the Stat3 pathway. For example, the inhibitor can substantially inhibit phosphorylation of the Stat3 protein, substantially inhibit dimerization of the Stat3 protein, substantially inhibit nuclear translocation of the Stat3 protein, substantially inhibit DNA-binding activity of the Stat3 protein, and/or substantially inhibit transcription activities of the Stat3 protein. Alternatively, the Stat3 pathway inhibitor may inhibit one or more upstream or downstream components in the Stat3 pathway.

Figure 2:
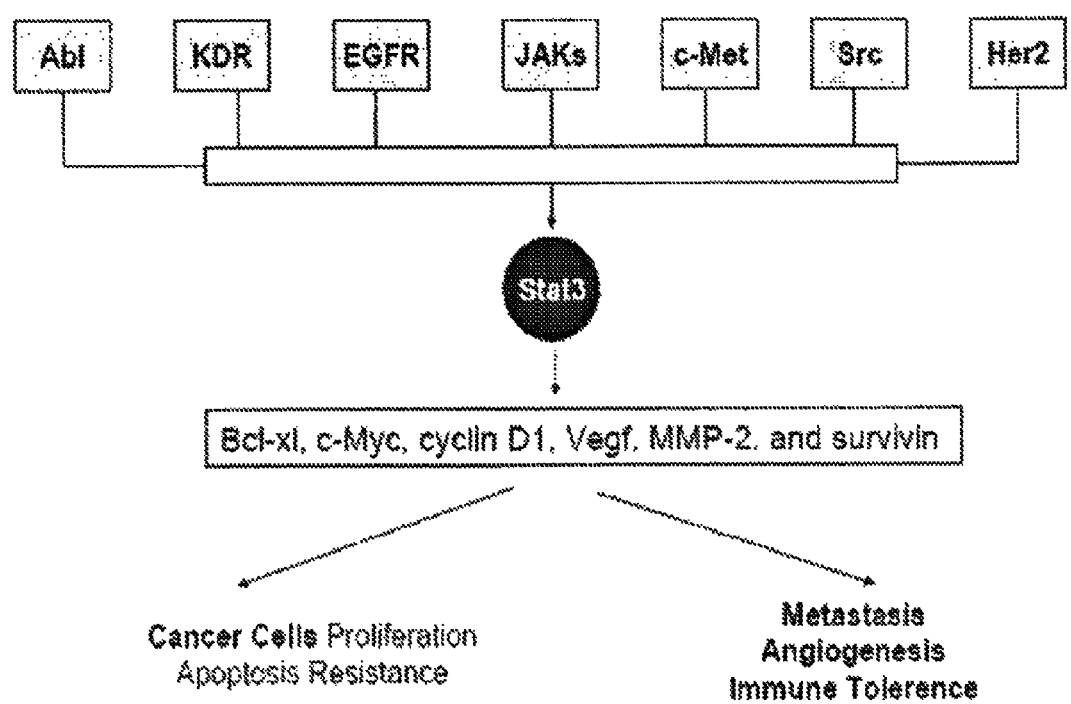
FIG. 2 shows the Stat3 pathway in cancer.

Stat3 pathway can be activated in response to cytokines, such as IL-6, or by a series of tyrosine kinases, such as EGFR, JAKs, Abl, KDR, c-Met, Src, and Her2. The downstream effectors of Stat3 include but are not limited to Bcl-xl, c-Myc, cyclinD1, Vegf, MMP-2, and survivin (FIG. 2). Stat3 pathway is found to be aberrantly active in a wide variety of human diseases, as shown in Table 1. Existing clinical samples examined showed that persistently active Stat3 pathway occurs in more than half of breast and lung cancers, hepatocellular carcinomas, multiple myelomas and more than 95% of head and neck cancers. Activated Stat3 has also been demonstrated in a number of autoimmune and inflammatory diseases. Furthermore, as cytokines, such as interleukin 6, mediated inflammation is the common causative origin for Atherosclerosis [38], Peripheral Vascular Disease [39, 40], Coronary Artery Disease [39, 40], hypertension [41], Osteoprorosis [42], Type 2 Diabetes [39], and Dementia [43] and 130-Jaks-Stats is the main pathway activated by IL-6, inhibition of Stat3 pathway may prevent these diseases as well.

TABLE 1

Activation of STAT3 PATHWAY in human diseases

| | | DISEASES | REF. |
|---|---|---|---|
| ONCOLOGY DISEASES | Solid Tumors | Breast Cancer | [44] |
| | | Head and Neck Cancer (SCCHN) | [45] |
| | | Lung Cancer | [46] |
| | | Ovarian Cancer | [47] |
| | | Pancreatic Cancer | [48] |

TABLE 1-continued

Activation of STAT3 PATHWAY in human diseases

| | | | DISEASES | REF. |
|---|---|---|---|---|
| | | | Colorectal carcinoma | [49] |
| | | | Prostate Cancer | [50] |
| | | | Renal Cell carcinoma | [51] |
| | | | Melanoma | [52] |
| | | | Hepatocellular carcinomas | [34] |
| | | | Cervical Cancer | [53] |
| | | | Endometrial Cancer | [53] |
| | | | Sarcomas | [54, 55] |
| | | | Brain Tumors | [56] |
| | | | Gastric Cancers | [27] |
| | Hematologic | | Multiple Myeloma | [57] |
| | Tumors | Leukemia | HTLV-1-dependent Leukemia | [58] |
| | | | Chronic Myelogenous Leukemia | [51] |
| | | | Acute Myelogenous Leukemia | [59] |
| | | | Large Granular Lymphocyte Leukemia | [60] |
| | | Lymphomas | EBV-related/Burkitt's | [61] |
| | | | Mycosis Fungoides | [51] |
| | | | HSV Saimiri-dependent (T-cell) | [51] |
| | | | Cutaneous T-cell Lymphoma | [62] |
| | | | Hodgkin's Diseases | [51] |
| | | | Anaplastic Large-cell Lymphoma | [63] |
| IMMUNE | Inflammatory | | Inflammatory Bowel Diseases | [64] |
| DISEASES | Diseases | | Inflammatory Arthritis | [65-67] |
| | | | Crohn's Diseases | [68] |
| | | | Chronic inflammatory conditions | [69] |
| | Autoimmune | | Reumatoid Arthritis | [65, 66, 70-72] |
| | | | Systemic lupus erythematosus | [73] |
| | Asthma | | | [74] |
| | Allergy | | | [75] |
| | Infections | | | [76] |
| PROLIFERA- | Psoriasis | | | [77] |
| TIVE | Keloids | | | [78] |
| DISORDERS | Warts | | | [79] |
| | Myelodysplastic syndrome | | | [80] |
| | Polycythemia vera | | | [81] |
| CNS | Alzhemer's | | | [36, 82, 83] |
| DISEASES | Multiple sclerosis (MS) | | | [36, 82, 84] |

In one embodiment, the Stat3 inhibitor according to the present invention is: 2-(1-hydroxyethyl)-naphtho[2,3-b]furan-4,9-dione, 2-acetyl-7-chloro-naphtho [2,3-b]furan-4,9-dione, 2-acetyl-7-fluoro-naphtho[2,3-b]furan-4,9-dione, 2-acetylnaphtho[2,3-b]furan-4,9-dione, 2-ethyl-naphtho[2,3-b]furan-4,9-dione, phosphoric acid mono-[1-(4,9-dioxo-3a,4,9,9a-tetrahydro-naphtho[2,3-b]furan-2-yl)-vinyl]ester, phosphoric acid 1-(4,9-dioxo-3a,4,9,9a-tetrahydro-naphtho[2,3-b]furan-2-yl)-vinyl ester dimethyl ester, an enantiomer, diastereomer, tautomer, and a salt or solvate thereof (the "Compound of the Invention") (Example 2). The present invention also provides both in vitro and in vivo data that the Compound of the Invention inhibits CSCs' self-renewal and induces apoptosis in CSCs (Example 3).

Having provided evidence that downregulation of Stat3 pathway inhibits CSCs, the present invention provides a method of identifying a drug candidate capable of inhibiting a cancer stem cell. The method comprises screening for a drug candidate that inhibits Stat3 pathway activity. In various embodiments, the drug candidate is a small molecule Stat3 inhibitor, an RNAi agent against Stat3, an antisense agent against Stat3, a peptidomimetic Stat3 inhibitor, or a G-quartet oligodeoxynucleotide Stat3 inhibitor.

In one embodiment, the drug candidate is capable of inducing cell death in CSC or at least inhibiting its self-renewal. Various phases in the pathway can be targeted for screening the drug candidate. For example, various embodiments of the method can screen for drug candidates that substantially inhibits phosphorylation of the Stat3 protein, substantially inhibits dimerization of the Stat3 protein, substantially inhibits nuclear translocation of the Stat3 protein, substantially inhibits DNA-binding activities of the Stat3 protein, or substantially inhibits transcription activities of the Stat3 protein.

As Example 2 below shows, the Compound of the Invention inhibits Stat3 transcription activity, and Stat3 DNA-binding activity in vitro. Example 2 further shows that the Compound of the Invention inhibits in vivo both the expression of Stat3 downstream effectors (e.g., cyclin D1 and survivin) and Stat3 DNA binding activity.

Accordingly, in another aspect, the present invention provides a method of inhibiting cellular Stat3 pathway activity where an effective amount of the Compound of the Invention is administered. In another aspect, the Compound of the Invention can be used to formulate a pharmaceutical composition to treat or prevent disorders or conditions associated with aberrant Stat3 pathway activities. A disorder is considered herein "associated with" aberrant Stat3 pathway activities if a patient suffering from the disorder, which can be a subtype within a type of disorder, typically have in at least some of the patient's cells aberrant Stat3 pathway activity, which can, but not necessarily, contribute to the pathology of the disorder. Some of the disorders known to be associated with aberrant Stat3 pathway activities include but are not limited to: autoimmune diseases, inflammatory diseases, inflammatory bowel diseases, arthritis, autoimmune demyelination disorder, Alzheimer's disease, stroke, ischemia reperfusion injury and multiple sclerosis. Some of the disorders known to be associated with aberrant Stat3 pathway activities are cancers and include but are not limited to: various types of breast cancers, head and neck cancers, lung cancers, ovarian cancers, pancreatic cancers, colorectal carcinoma, prostate cancers, renal cell carcinoma, melanoma, hepatocellular carcinomas, cervical cancers, sarcomas, brain tumors, gastric cancers, multiple myeloma, leukemia, and lymphomas.

Related to this aspect of the invention, a kit is provided that includes one or more agents for diagnosing a disorder associated with aberrant Stat3 pathway activities, and a therapeutically effective amount of the Compound of the Invention or another effective Stat3 pathway inhibitor. The diagnostic agent can be any suitable reagent depending on the suspected disorder, and may include agents needed to draw a blood sample, take a biopsy, screen for a biomolecule (e.g., antigen or antibody) or extract genetic information from a sample. The agent may include a solvent, a detergent, an anticoagulant, an antigen, an antibody, an enzyme, a PCR primer, and so on.

Whether or not a patient is diagnosed with a disorder known to implicate aberrant Stat3 activity, a physician can always order a test to see if there is aberrant Stat3 activity in a biopsy sample taken from the patient. Therefore, a kit is provided that includes: one or more agents for diagnosing aberrant Stat3 pathway activities, and a therapeutically effective amount of the Compound of the Invention or another effective Stat3 pathway inhibitor. In one feature, aberrant Stat3 pathway activity can be identified through any suitable analytical means to examine any indicia of such activity, e.g., expression (level, duration, etc.) of phosphorylated Stat3 or of a surrogate upstream or downstream regulator of Stat3 phosphorylation. Similar to the kit described previously, the diagnostic agent can be any suitable reagent depending on the indicia of aberrant Stat3 pathway activity that the test looks at.

As Example 3 below shows, the Compound of the Invention, which is at least a Stat3 pathway inhibitor, kills cancer stem cells. Example 3 also demonstrates that the Compound of the Invention also inhibits CSC spherogenesis, an indication of successful inhibition of CSC self-renewal, both in vitro and in vivo.

Accordingly, in an aspect, the present invention provides a method of inhibiting cancer stem cells where an effective amount of the Compound of the Invention is administered to the cells. Cancers known to have CSCs are good candidates for such treatments, and include but are not limited to: various types of breast cancers, head and neck cancers, lung cancers, ovarian cancers, pancreatic cancers, colorectal carcinoma, prostate cancers, liver cancers, melanoma, multiple myeloma, brain tumors, sarcomas, medulloblastoma, and leukemia.

Further, as CSCs have been demonstrated to be fundamentally responsible for tumorigenesis, cancer metastasis and cancer reoccurrence, any methods of the invention directed to inhibiting CSCs can be practiced to treat cancer that is metastatic, refractory to a chemotherapy or radiotherapy, or has relapsed in the subject after an initial treatment. Example 6 below specifically tests in vivo the anti-metastasis efficacy of the Compound of the Invention, and the data show significant reduction in the number of primary tumor foci and the spontaneous liver metastasis.

In Example 4 below, the Compound of the Invention is not only shown to cause apoptosis in a broad spectrum of cancer cells, but also to exhibit selectivity in its cytotoxicity which is critical for developing low-toxicity therapeutics. Selective cytotoxicity as used herein refers to a compound's ability to kill cancer cells while substantially sparing normal cells, sometimes under certain conditions. Normal cells usually refer to healthy, non-tumorigenic cells. Conditions that result in selective cytotoxicity for a drug candidate are hard to predict because they require knowledge of the underlying mechanism of cytotoxicity. For example, to lower the toxicity of an anti-cancer drug that targets microtubule formation during mitosis presents quite different factors to work with than a drug that blocks cellular metabolic processes. A suitable condition for engendering selective cytotoxicity needs to balance the need for the drug to be toxic enough to effectively kill cancer cells while tolerable enough to normal cells. For instance, if lower concentration is used, that often means prolonged infusion is needed to kill cancer cells.

From data generated in the examples of this invention including those shown in Example 4, it appears that selective cytotoxicity can be achieved for the Compound of the Invention if affected cells are not exposed to a critical concentration of the compound continuously beyond a certain duration. In a method aimed at selectively killing cancer cells in a subject, a pharmaceutical composition that has the Compound of the Invention is administered to the subject such that the compound concentration in the subject's plasma is not maintained above a critical concentration for more than 24 hours after each dose. This method can be used to treat all cancers, including any of the groups of cancers described here, and to treat Stat3-associated disorder, an exemplary list of which is already provided above and is not repeated here. Alternatively, the duration can be further restricted to 12, 16, and 20 hours after each dose. The critical concentration for each compound may vary. In various embodiments of the present invention, the critical concentration is about 100 µM, about 50 µM, about 30 µM, or about 20 µM.

In one embodiment of the method, the cancer being treated is selected from the following group: liver cancer, head and neck cancer, pancreatic cancer, gastric cancer, renal cancer, sarcoma, multiple myeloma, metastatic breast cancer, metastatic prostate cancer, leukemia, lymphoma, esophageal cancer, brain tumor, glioma, bladder cancer, endometrial cancer, thyroid cancer, bile duct cancer, bone cancer, eye cancer (retinoblastoma), gallbladder cancer, pituitary cancer, rectal cancer, salivary gland cancer, and nasal pharyngeal cancer.

In an aspect, the present invention provides a method of treating cancer in a subject, where a therapeutically effective amount of a pharmaceutical composition comprising the Compound of the Invention is administered to the subject. The cancer may be metastatic. The subject may be a mammal, e.g., a human being.

For any of the methods of treating a subject described herein, the present invention provides effective dosing ranges, dosing frequencies, and plasma concentrations of the compounds. In various embodiments, the pharmaceutical composition is administered at a dosage: (a) from about 1 mg/m$^2$ to about 5,000 mg/m$^2$ (I.V.) or from about 1 mg/m$^2$ to about 50,000 mg/m$^2$ (PO); (b) from about 2 mg/m$^2$ to about 3,000 mg/m$^2$ (I.V.) or from about 10 mg/m$^2$ to about 50,000 mg/m$^2$ (PO). In various embodiments, the compound of the present invention can be administered every other day (Q2D), daily (QD), or twice a day (BID). In one embodiment, the pharmaceutical composition is administered orally and no more than four times a day (QID).

In one feature, the pharmaceutical composition is administered to the subject such that the compound concentration in the subject's plasma is not maintained above a critical concentration for more than 24 hours (or 12, 16, and 20 hours) after each dose. According to alternative embodiments of the invention, the plasma concentration of the compound does not exceed the critical concentration at a certain time point after each does, e.g., 12, 16, 20, or 24 hours, as a regimen that avoids non-selective toxicity. In various embodiments of the present invention, the critical concentration is about 100 µM, about 50 µM, about 30 µM, or about 20 µM. The compositions, in certain cases, are isolated, purified or synthesized.

In another aspect, the present invention provides a pharmaceutical composition that comprises the Compound of the Invention, and a pharmaceutically-acceptable excipient, carrier, or diluent. In one feature, the composition is suitable for oral, nasal, topical, rectal, vaginal or parenteral administration, or intravenous, subcutaneous or intramuscular injection.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the mammal being treated and the particular mode of administration. The amount of active ingredient, which can be combined with a carrier material to produce a single dosage form, will generally be that amount of the compound which produces a therapeutic effect. Generally, out of 100%, this amount will range, for example, from about 1% to about 99% of active ingredient, from about 5% to about 70%, from about 10% to about 30%.

Therapeutic compositions or formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of the Compound of the Invention as an active ingredient. The Compound of the Invention may also be administered as a bolus, electuary or paste.

In solid dosage forms of the invention for oral administration (capsules, tablets, pills, dragees, powders, granules and the like), the Compound of the Invention is mixed with one or more pharmaceutically-acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, sodium carbonate, and sodium starch glycolate; solution retarding agents, such as paraffin; absorption accelerators, such as quaternary ammonium compounds; wetting agents, such as, for example, cetyl alcohol, glycerol monostearate, and polyethylene oxide-polypropylene oxide copolymer; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Liquid dosage forms for oral administration of the Compound of the Invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof. Additionally, cyclodextrins, e.g., hydroxypropyl-.beta.-cyclodextrin, may be used to solubilize compounds.

Besides inert diluents, the oral compositions can also include adjuvants such as wetting agents, emulsifying and suspending agents, sweetening, flavoring, coloring, perfuming and preservative agents. Suspensions, in addition to one or more Compounds of the Invention, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more Compounds of the Invention, with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active pharmaceutical agents of the invention. Formulations of the present invention which are suitable for vaginal administration also include pessaries, tampons, creams, gels, pastes, foams or spray formulations containing such carriers as are known in the art to be appropriate.

Dosage forms for the topical or transdermal administration of a composition according to the invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to the Compound of the Invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Ophthalmic formulations, eye ointments, powders, solutions and the like, are also contemplated as being within the scope of this invention.

Pharmaceutical compositions of this invention suitable for parenteral administration comprise one or more compounds according to the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

In some cases, in order to prolong the effect of the composition according to the invention, it is desirable to slow its absorption by the body from subcutaneous or intramuscular injection. This may be accomplished by the use of a liquid suspension of crystalline or amorphous material having poor water solubility. The rate of absorption of the drug then depends upon its rate of dissolution, which, in turn, may depend upon crystal size and crystalline form. Alternatively, delayed absorption of a parenterally-administered composition is accomplished by dissolving or suspending the compound in an oil vehicle. One strategy for depot injections includes the use of polyethylene oxide-polypropylene oxide copolymers wherein the vehicle is fluid at room temperature and solidifies at body temperature.

The pharmaceutical compounds of this invention may be administered alone or in combination with other pharmaceutical agents, or with other anti-cancer therapies as described herein, as well as in combination with a pharmaceutically-acceptable excipient, carrier, or diluent.

In an embodiment, the pharmaceutically acceptable excipient, carrier, or diluent comprises a lipid for intravenous delivery. The lipid can be: phospholipids, synthetic phophatidylcholines, natural phophatidylcholines, sphingomyelin, ceramides, phophatidylethanolamines, phosphatidylglycerols, phosphatidic acids, cholesterol, cholesterol sulfate, and hapten and PEG conjugated lipids. The lipid may be in the form of nanoemulsion, micelles, emulsions, suspension, nanosuspension, niosomes, or liposomes. In an embodiment, the pharmaceutically acceptable excipient, carrier, or diluent is in a form of micellar emulsion, suspension, or nanoparticle suspension, and it further comprises an intravenously acceptable protein, e.g., human albumin or a derivative thereof, for intravenous delivery.

In an embodiment, the pharmaceutically acceptable excipient, carrier, or diluent comprises a waxy material for oral delivery. The waxy material may be mono-, di-, or tri-glycerides, mono-, di-fatty acid esters of PEG, PEG conjugated vitamin E (vitamin E TPGs), and/or Gelucire. The Gelucire can be selected from Gelucire 44/14, Gelucire 43/01, Gelucire 50/02, Gelucire 50/13, Gelucire 37/02, Gelucire 33/01, Gelucire 46/07, and Gelucire 35/10. In an embodiment, the pharmaceutically acceptable excipient, carrier, or diluent is selected from capryol, transcutol hp, labrafil M, labrasol, triacetin, pharmasolv, ethanol, poly vinyl pyrrolidine, carboxymethyl cellulose, tween 20, and tween 80. In an embodiment, the pharmaceutically acceptable excipient, e.g., Gelucire 44/14, is mixed with a surfactant, which can be Tween 80 or Tween 20. These embodiments of pharmaceutical compositions can be further formulated for oral administration.

The Compound of the Invention can be synthesized using commercially available starting materials and processes well known to one skilled in the art of organic chemistry. In Examples 8-10, the present invention provides a manufacturing process for some of the claimed compounds.

According to one or more embodiments of the present invention, a small molecule Stat3 inhibitor refers to any low molecular-weight drug that shows inhibitory activity against Stat3. Compared to larger molecular weight pharmaceuticals such as proteins, peptides, and carbohydrates, small molecules can more easily penetrate cell membranes and the blood brain barrier. These molecules tend to incur lower process development and manufacturing costs.

According to one or more embodiments of the present invention, an RNAi therapy is the direct use of RNA interference (RNAi) in the treatment of diseases by silencing genes that give rise to bad proteins and, therefore, disease. RNAi is a naturally occurring process that suppresses certain gene activity in living cells. It is a widely conserved eukaryotic function that double stranded RNA triggers in cells via short RNA duplex intermediates such as small interfering RNAs (siRNAs). Through a series of processing steps, one of the two strands of the siRNA complexes with proteins to form RISC(RNA-induced silencing complex). RISC recognizes the complementary RNA sequence by Watson-Crick base pairing and then cleaves it. RNAi also include shRNA, miRNA, and others.

According to one or more embodiments of the present invention, an antisense therapy is a form of treatment for genetic disorders or infections. When the genetic sequence of a particular gene is known to be causative of a particular disease, it is possible to synthesize a strand of nucleic acid (DNA, RNA or a chemical analogue) that will bind to the messenger RNA (mRNA) produced by that gene and inactivate it, effectively turning that gene "off." This is because mRNA has to be single stranded for it to be translated. This synthesized nucleic acid is termed an "anti-sense" oligonucleotide because its base sequence is complementary to the gene's messenger RNA (mRNA), which is called the "sense" sequence (so that a sense segment of mRNA "5'-AAGGUC-3'" would be blocked by the anti-sense mRNA segment "3'-UUCCAG-5'").

According to one or more embodiments of the present invention, a peptidomimetic is a small protein-like chain designed to mimic a peptide. They typically arise from modification of an existing peptide in order to alter the molecule's properties. For example, they may arise from modifications to change the molecule's stability or biological activity. This can have a role in the development of drug-like compounds from existing peptides. These modifications involve changes to the peptide that will not occur naturally (such as altered backbones and the incorporation of non-natural amino acids).

According to one or more embodiments of the present invention, G-quartet oligodeoxynucleotide inhibitors are catalytic DNA molecules (DNAzymes) designed to inhibit proteins independent of their RNA-cleavage activity in cells.

Materials and Methods

Biological Assays

Compounds of the present invention can be tested according to the protocol described above. Table 2 shows the list of compounds described in the protocol.

TABLE 2

| Compound Name | Compound Code |
| --- | --- |
| 2-(1-hydroxyethyl)-naphtho[2,3-b]furan-4,9-dione | 301 |
| 2-Acetyl-7-Chloro-naphtho[2,3-b]furan-4,9-dione | 416 |
| 2-Acetyl-7-Fluoro-naphtho[2,3-b]furan-4,9-dione | 418 |
| 2-acetylnaphtho[2,3-b]furan-4,9-dione | 401 |
| 2-ethyl-naphtho[2,3-b]furan-4,9-dione | 101 |
| phosphoric acid mono-[1-(4,9-dioxo-3a,4,9,9a-tetrahydro-naptho[2,3-b]furan-2-yl)-vinyl]ester | 4011 |
| phosphoric acid 1-(4,9-dioxo-3a,4,9,9a-tetrahydro-naptho[2,3-b]furan-2-yl)-vinyl ester dimethyl ester | 4012 |

Cell Culture:

HeLa, DU145, H1299, DLD1, SW480, A549, MCF7, LN18, HCT116, HepG2, Paca2, Panc1, LNcap, FaDu, HT29, and PC3 cells (ATCC, Manassas, Va.) were maintained in Dulbecco's Modified Eagle Medium (DMEM) (Invitrogen, Carlsbad, Calif.) supplemented with 10% fetal bovine serum (FBS) (Gemini Bio-Products, West Sacramento, Calif.) and 5% penicillin/streptomycin/amphotercin B (Invitrogen).

Hoechst Side Population:

To identify and isolate side population (SP) and non-SP fractions, SW480 cells were removed from the culture dish with trypsin and EDTA, pelleted by centrifugation, washed with phosphate-buffered saline (PBS), and resuspended at 37° C. in Dulbecco's modified Eagle's medium (DMEM) containing 2% FBS and 1 mM HEPES. The cells were then labeled with Hoechst 33342 (Invitrogen) at a concentration of 5 µg/mL. The labeled cells were incubated for 120 minutes at 37° C., either alone or with 50 µM verapamil (Sigma-Aldrich, St. Louis). After staining, the cells were suspended in Hanks' balanced saline solution (HBSS; Invitrogen) containing 2% FBS and 1 mM HEPES, passed a through 40 µm mesh filter, and maintained at 4° C. until flow cytometry analysis. The Hoechst dye was excited at 350 nm, and its fluorescence was measured at two wavelengths using a 450 DF10 (450/20 nm band-pass filter) and a 675LP (675 nm long-pass edge filter) optical filter. The gating on forward and side scatter was not stringent, and only debris was excluded [15].

CSC Isolation with Surface Markers:

Sorting tumor cells based primarily upon the differential expression of the surface marker(s), such as CD44 or CD133, have accounted for the majority of the highly tumorigenic CSCs described to date. CD133 isolation is based upon the method of Ricci-Vitiani et al. [20], with slight modification. CD133$^+$ cells were isolated by either fluorescence activated cell sorting (FACS) or magnetic nanoparticle-based separation. Briefly, $10^7$ cells/mL were labeled with CD133/1 (AC133)-PE for FACS-based cell sorting; or with CD133/1 (AC133)-biotin (Miltenyi Biotec, Auburn, Calif.) for magnetic field-based separation using the EasySep® biotin selection kit (Miltenyi Biotec) according to the manufacturer's recommendations. Non-specific labeling was blocked with the supplied FcR blocking reagent and antibody incubations (1:11) were carried out on ice for 15 minutes in PBS with 2% FBS and 1 mM EDTA. Five washes were done for EasySep® isolation, whereas cells were pelleted at 400×g for 5 minutes and resuspended at $2\times10^7$/mL, before sorting by FACS.

CD44$^{high}$ cells were isolated by FACS according to the methods described in Ponti et al, with slight modification [85]. Briefly, after trypsinization and recovery of cells for 30 minutes at 37° C. in growth media, cells were pelleted at 400×g and were resuspended in PBS with 2% FBS and 1 mM EDTA at $1\times10^6$ cells/mL. Cells were then incubated on ice with a 1:100 dilution of CD44-FITC (BD Biosicences, San Diego, Calif.) for 15 minutes. Alternatively, CD24-PE (BD Biosciences, San Diego, Calif.) (1:100) was utilized for negative selection. After washing three times, cells were resuspended at $2\times10^6$/mL and passed through a 40 µM mesh before sorting Sphere Assay:

A reliable method of measuring the self-renewal capacity of cell population if the ability to be cultured as spheres in the absence of serum or attachment. CD44$^{high}$ FaDu or Hoechst side population cancer stem cells were cultured in ultra low attachment plates in cancer stem cell media (DMEM/F12, B27 Neurobasal supplement, 20 ng/ml EGF, 10 ng/ml FGF, 4 µg/ml insulin, and 0.4% BSA) to allow spheres formation. Typically, sphere formation was evaluated by microscopy after 10-14 days in culture and spheres with >50 cells were scored.

Luciferase Reporter Assay:

HeLa Cells were co-transfected with Stat3-luciferase (Stat3-Luc) reporter vector (Panomics, Fremont, Calif.) and Renilla luciferase (Promega, Madison, Wis.) using Lipofectamine 2000 as described by the manufacturer (Invitrogen). Following transfection, cells were maintained in medium containing 0.5% FBS for 24 hours. Cells were then treated with the indicated compound for 30 minutes prior to the addition of 25 ng/ml oncostatin M (OSM) (R&D Systems, Minneapolis, Minn.) to the medium. 6 hours following OSM addition, cells were harvested and levels of firefly and renilla luciferase were measured using the Dual-Glo Luciferase Assay System as described by the manufacturer (Promega).

Analysis of Apoptosis:

Cells treated with or without compound were harvested at 5 hours post treatment for Annexin-V staining. Collected cells were washed with PBS and resuspended in Annexin-V-FITC containing buffer and stained according to manufactures directions (Roche). Annexin-V positive cells were determined by Flow cytometry.

STAT3 DNA Binding Assay:

Electrophoretic mobility shift assay (EMSA) was performed as described by the manufacturer (Li-Cor Biosciences, Lincoln, Nebr.). Briefly, nuclear extracts were made from HeLa cells using the NucBuster Protein Extraction Kit as described by the manufacturer (EMD Biosciences, San Diego, Calif.). 5 µg of nuclear extract was pre-incubated with the indicated dose of indicated compound for 30 minutes prior to a 15-minute incubation with the IR700-labeled consensus Stat3 oligonucleotide. Samples were then electrophoresed on a polyacrylamide gel and directly scanned using the Odyssey infrared imaging system (Li-Cor Biosciences). For the enzyme-linked immunosorbent assay (ELISA), 5 µg of nuclear extract was preincubated with indicated concentration of indicated compound for 30 minutes prior to the addition of biotinylated oligo (5'-Biotin-GATCCTTCTGGGAATTCCTAGATC-3', SEQ ID NO. 1). Stat3-DNA complexes were then captured on streptavidin coated 96 well plates (Pierce, Rockford, Ill.). Bound complexes were then incubated with Stat3 polyclonal antibody (Santa Cruz Biotechnology, Santa Cruz, Calif.) followed by anti-rabbit HRP conjugated secondary antibody (GE Healthcare, Pittsburgh, Pa.). Bound antibody was then visualized by addition of TMB substrate (Pierce) and absorbance measured at 450 nm.

Cell Viability Determination:

For 3-(4,5 dimethylthiazol-2-yl)-2,5-diphenyltetrazolium (MTT) (Sigma-Aldrich, St. Louis, Mo.) analysis, cells were plated in 96 well plates at 10,000 cells per well. 24 hours after plating, compound was added to cells at indicated doses. 22 hours following compound addition, MTT was added to each well (0.5 mg/ml, final concentration) and plates were incubated for an additional 2 hours at 37° C. Medium was then aspirated and the formazan product was solubilized in 100 µl of isopropyl alcohol. The absorbance of each well was measured at 570 nm using a microplate reader.

Immunofluorescence:

Cells treated with indicated compound for an indicated time were either fixed in 4% formaldehyde or cold methanol for the detection of Annexin V, cleaved caspase 3, or stat3, respectively. Coverslips were air dried and rehydrated in PBS at room temperature for 10 min. Samples were then incubated in blocking buffer (PBS, 5% FBS) for 10 min at room temperature in a humid chamber. Cells were incubated overnight at 4° C. with primary antibodies. After washing, the cells were incubated for 1 hour at room temperature with a 1:500 dilution of FITC conjugated anti-rabbit antibody. Images were captured with a Nikon TE200 microscope equipped with epifluorescence and a SPOT mosaic CCD camerapolyclonal Anti-cleaved caspase 3 antibody (1:100) was obtained from Cell Signaling Technology, Danvers, Mass. Annexin-V-FITC was obtained from Roche, Penzberg, Germany. Polyclonal anti-Stat3 antibody was obtained from Santa Cruz.

Gene Knockdown by TPIV® Technology:

The TPIV® (Therapeutic Pathway Identification and Validation) technology (Boston Biomedical Inc., Norwood, Mass., USA) provides plasmids that can be used to first transfect bacteria that are in turn taken up by a mammalian subject. After bacterial lysis, dsRNA encoded by the TPIV® plasmids and processed by the bacteria get released into the mammalian cell cytoplasm and effect targeted gene knockdown. The TPIV® technology is described in co-owned PCT patent application no. PCT/US08/68866 filed on Jun. 30, 2008, the entire content of which is incorporated herein by reference. Specifically, a TPIV® plasmid that encodes effective siRNA sequences against Stat3 was constructed by PCR-cloning of a Stat3 plasmid purchased from Origene Technologies (Rockville, Md., USA) using the following primers:

```
TPIV-Stat3 (300 bp insert)
Primers:
                                       (SEQ ID NO. 2)
Stat3 TPIV For 5'-GGATCTAGAATCAGCTACAGCAGC (SEQ ID NO. 3)
Stat3 TPIV Rev 5'-TCCTCTAGAGGGCAATCTCCATTG
```

The control plasmid is constructed using a pGL2 plasmid purchased from Promega (Madison, Wis., USA).

```
TPIV-GL2 (300 bp insert)
Primers:
                                       (SEQ ID NO. 4)
GL2 TPIV For 5'-CCCTCTAGATGGTTCCTGGAAC (SEQ ID NO. 5)
GL2 TPIV Rev 5'-GCTCTAGAAACCCCTTTTGG
```

Chemically competent *E. coli* BL21 (DE3) pLYSe bacteria (50~100 μl) were transformed with control or 100 ng of Stat3-targeting TPIV® plasmid according to the manufacturer instructions (Stratagene). A single colony was then inoculated into BHI medium containing 100 μg/ml ampicillin, and grown overnight at 37° C. The next day, 5 ml of each overnight culture was diluted 1:40 into fresh BHI medium containing 100 μg/ml ampicillin and grown for a further 2-4 hours (until the $OD_{600}$=0.5). Each culture was then treated with IPTG (1 mM final concentration) for 2-4 hours to induce transcription of the long double strand RNAs which would be processed into a cocktail siRNAs by the bacteria. After IPTG induction, the total number of bacteria in each culture was calculated by measuring the $OD_{600}$ value ($8 \times 10^8$ bacteria/ml culture has an $OD_{600}$=1). The number of bacteria for cell treatment was then calculated according to cell confluency and the needed multiplicity of infection (MOI; try ranges of 20:1 to 2000:1, bacteria to cells) in an appropriate reaction volume. As a rule of thumb, the reaction volume should be chosen to result in $3 \times 10^8$/ml for a 1000:1 MOI. The required volume of bacteria culture was then centrifuged at 2500 g for 10 mins at 4° C. and the pellet was washed once with serum-free culture medium that was used for the cells being bactofectioned plus 100 μg/ml ampicillin and 1 mM of IPTG, and resuspended in the same medium at the required density for bacterial infection (bactofection).

At the same time, cancer cells or cancer stem cells were isolated. 30 minutes before bactofection, the cell culture medium was replaced with 2 ml of fresh serum-free medium containing 100 μg/ml of ampicillin and 1 mM IPTG. Bacteria prepared above were then added to the cells at the desired MOI for 2 hours at 37° C.

After the infection period, the cells were washed 3 times using serum-free cell culture medium. The cells were then incubated with 2 ml of fresh complete cell culture medium containing 100 μg/ml of ampicillin and 150 μg/ml of gentamycin for 2 hours to kill any remaining extracellular bacteria. After treatment with ampicillin and gentamycin, the cells were incubated with 3 ml of fresh complete RPMI 1640 medium containing 10 μg/ml of ofloxacin to kill any intracellular bacteria. The cells were then harvested or analysis at various time points in order to assess the extent of target gene silencing and the resulting phenotypes.

In Life Evaluations:

Daily examinations into the health status of each animal were also conducted. Body weights were checked every three days. Food and water was supplied daily according to the animal husbandry procedures of the facility. Treatment producing >20% lethality and or >20% net body weight loss were considered toxic. Results are expressed as mean tumor volume ($mm^3$)±SE. P Values<0.05 are considered to be statistically relevant.

Animal Husbandry:

Male or female athymic nude mice 4-5 weeks (Charles River Laboratories, Wilmington, Mass.), were acclimated to the animal housing facility for at least 1 week before study initiation. All of the experimental procedures utilized were consistent with the guidelines outlined by the American Physiology Society and the Guide for the Care and Use of Laboratory Animals and were also approved by the Institutional Animal Care and Use Committee of Boston Biomedical Inc. The animals were housed in groups of four in wood chip bedded cages in a room having controlled temperature (68° F.-72° F.), light (12-h light-dark cycle), and humidity (45-55%). The animals were allowed free access to water and food during the experiment.

Intrasplenic-Nude Mouse Model System (ISMS Model):

The female nude mice were anesthetized and under aseptic conditions, an incision was made in the left flank to expose the spleen. One million human colon cancer HT29 cells in 0.1 ml PBS were injected under the spleen capsule using a 27-gauge needle. The spleen was replaced in the peritoneal cavity and the incision was closed. Treatment started the next day after the implantation till the examination day. The regimen of the treatments is 5 qd/wk via i.p. The mice were sacrificed when moribund or 30 days after the injection. The spleen and liver were removed and examined, and the number of tumor lesions was recorded.

Example 1

Identification of Stat3 as an Anti-Cancer Stem Cell Target

Figure 3A:
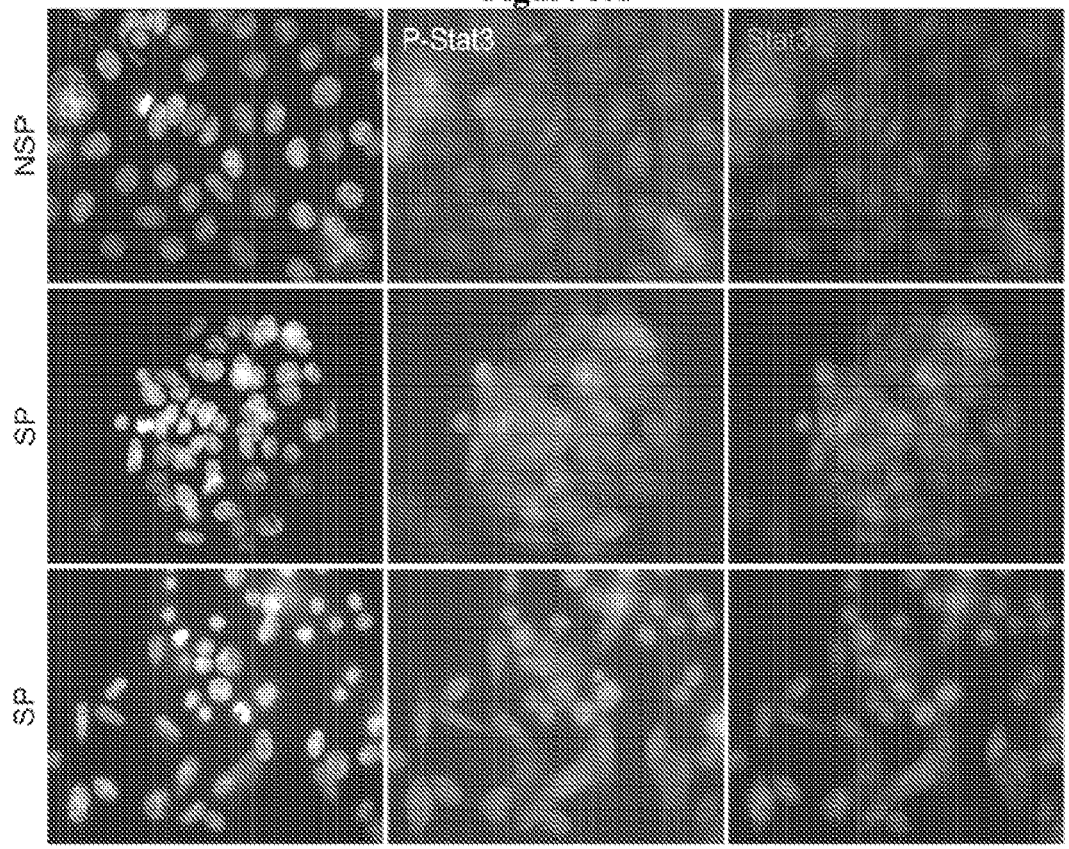
FIG. 3A shows that Stat3 is constitutively active in Hoechst Side Population cells.

Stat3 knockdown in CSCs induces apoptosis. To determine whether cancer stem cells expressed Stat3 and whether Stat3 was constitutively active, we performed immunofluorence microscopy, which allows not only the analysis of rare cell populations, but also provides additional information on protein localization and the ability to correlate staining with phenotype (i.e. apoptosis). Following immunofluorescent detection of p-Stat3 and Stat3 in NSP and SP cells isolated by FACS from SW480 colon cancer cells, we determined that Stat3 was indeed present in SP cells and that it was modestly enriched in the nucleus (FIG. 3A). In addition, we also observed increased p-Stat3 staining in SP cells over NSP cells, suggesting that SP cells may rely more heavily on Stat3 for survival.

Figure 3B:
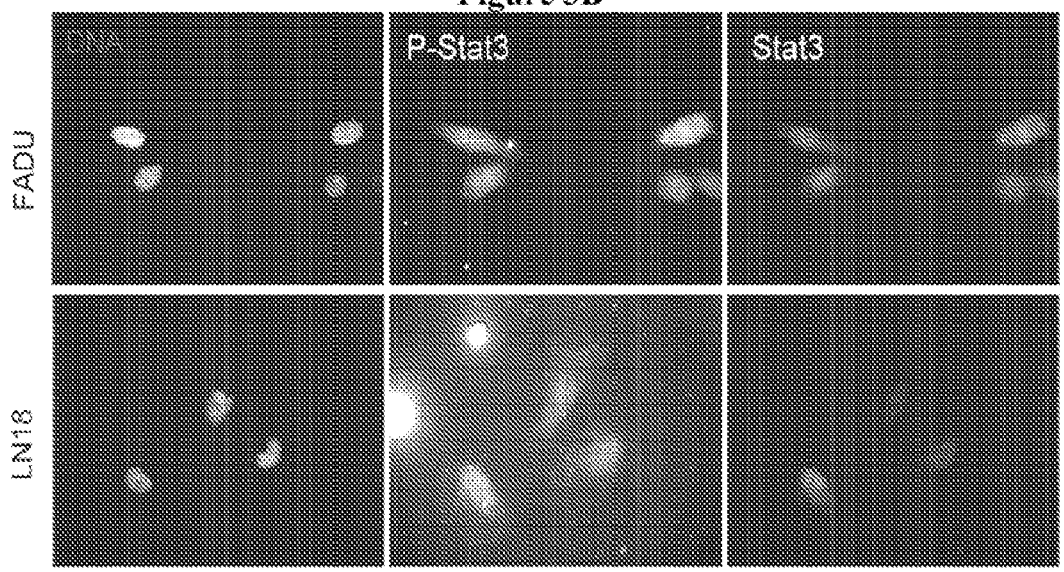
FIG. 3B shows that Stat3 is constitutively active in CD133$^+$ cells.

The status of Stat3 was also evaluated in $CD133^+$ cells isolated from FaDu human head and neck cancer cells and LN18 human glioblastoma cells. As shown in FIG. 3B, Stat3 are also constitutively active in these cells. Taken together, these data suggest Stat3 as a target that is particularly important for cancer stem cells.

Figure 4A:
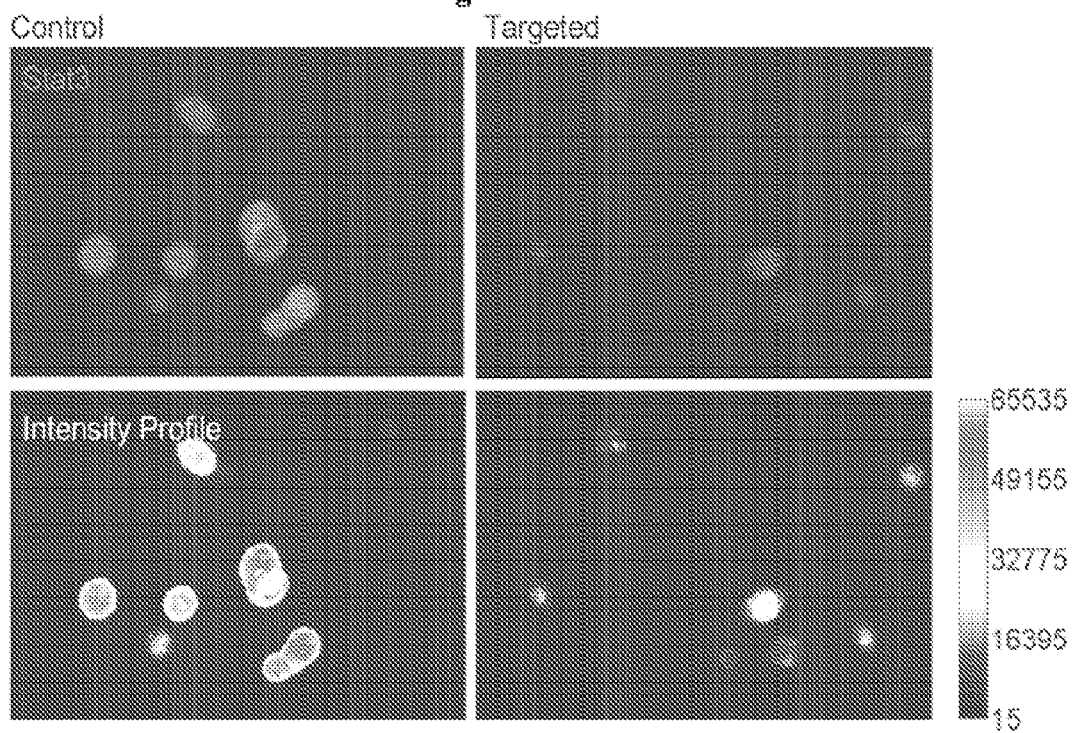
FIGS. 4A and 4B show that Stat3 knockdown in cancer stem cells induces apoptosis.
Figure 4B:
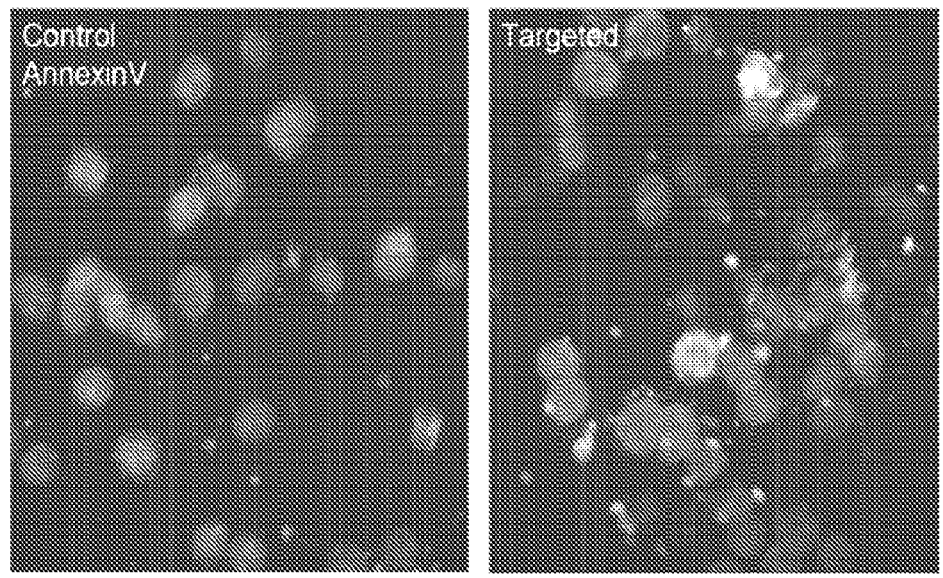

We next tested the effect of Stat3 knockdown in CSCs using TPIV®. Immunofluorescence analysis revealed that significant depletion of Stat3 could be achieved within 24 hours of infection (FIG. 4A) on freshly isolated CSCs (SP) and found that the majority of cells treated with Stat3-targeting TPIV® plasmids underwent apoptosis within 24 hours of infection, whereas control TPIV® plasmids did not induce apoptosis to levels above control, uninfected cells (FIG. 4B). These data demonstrate that cancer stem cells depend upon Stat3 for survival.

Knock Down of Stat3 in CSCs Inhibits CSC Spherogenesis.

Figure 5:
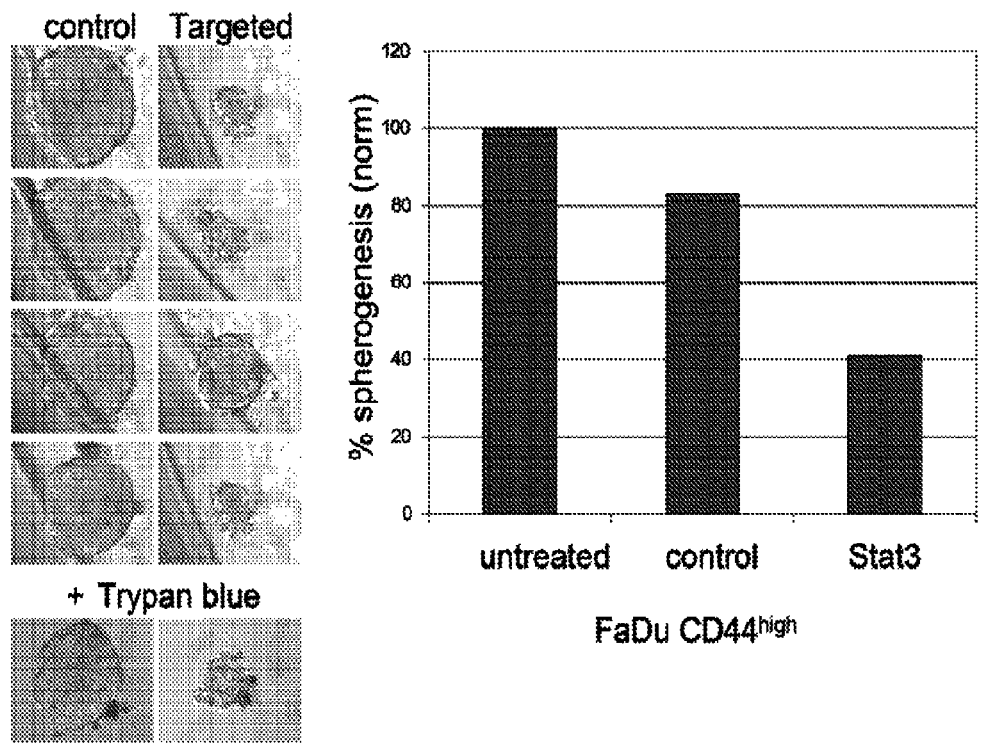
FIG. 5 shows that Stat3 knockdown in cancer stem cells inhibits cancer stem cell spherogenesis.

$CD44^{high}/CD24^{low}$ FaDu or Hoeschst side population cancer stem cells were isolated by FACS, and cultured in ultra low attachment plates in cancer stem cell media (DMEM/F12, B27 Neurobasal supplement, 20 ng/mL EGF, 10 ng/mL FGF, 4 µg/mL insulin, and 0.4% BSA) to allow sphere formation. Primary spheres were collected, disaggregated with trypsin, and distributed to 96-well ultra low attachment plated prior to TPIV® treatment. Bacteria were administered at an MOI of 1000 for two hours before addition of anti-biotic cocktail (penstrep, gentamycin, oflaxacin). Sphere formation was assessed after 10-14 days in culture. Representative sphere images were captured before (FIG. 5, left upper panels) or after the addition of trypan blue to identify dead cells (FIG. 5, left bottom panel). Relative spherogenesis was shown in the right panel of FIG. 5. The data clearly showed that Stat3 knockdown in cancer stem cells inhibits sphereogenesis, demonstrating that Stat3 is a key self-renewal factor of cancer stem cells.

Example 2

Identification of Compounds that Inhibit Stat3 Pathway Activity

Inhibition of Stat3 Transcription Activity.

Figure 6:
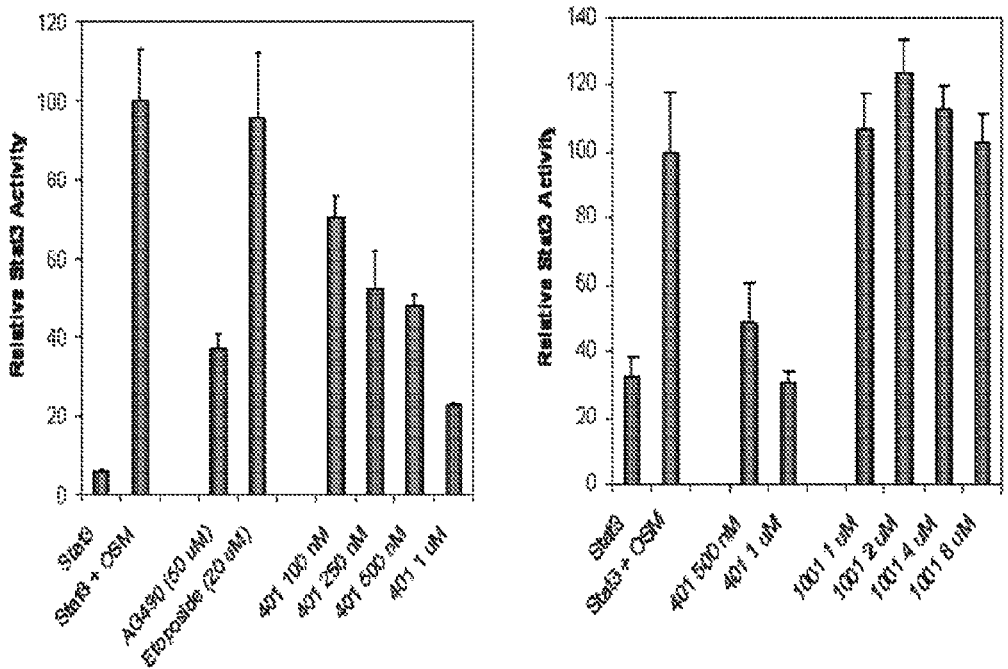
FIG. 6 shows that compound 401 inhibits Stat3 transcription activation activity.

Compounds were tested for their ability to inhibit Stat3 transcription activation activity in cells using a Stat3-luciferase (Stat3-luc) reporter construct. Cells transfected with Stat3-luc were cultured in reduced serum medium prior to addition of indicated compound for 30 minutes. Cells were then stimulated with 25 ng/ml oncostatin M (OSM) for 6 hours followed by detection of Stat3-luc reporter activity. Incubation of cells with compound 401 inhibited OSM-stimulated Stat3 reporter activity (FIG. 6, left panel). AG490, a known inhibitor of the Jak-Stat pathway, was included as a positive control for Stat3 inhibition. Etoposide, included as a control for genotoxic activity, showed little or no Stat3 inhibition. Compound 1001, which is naphthalene instead of naphthoquinone as the compounds in this invention, did not inhibit OSM-stimulated Stat3 reporter activity even at a much higher concentration (FIG. 6, right panel).

Additional compounds were tested in the Stat3 luciferase reporter assays and the results are summarized in Table 3.

TABLE 3

| Compound # | $IC_{50}$ in Stat3-Luc assays |
| --- | --- |
| 401 | ~0.25 µM |
| 416 | ~0.75 µM |
| 418 | ~0.75 µM |
| 301 | ~2 µM |

Inhibition of Stat3 DNA-Binding Activity.

Figure 7A:
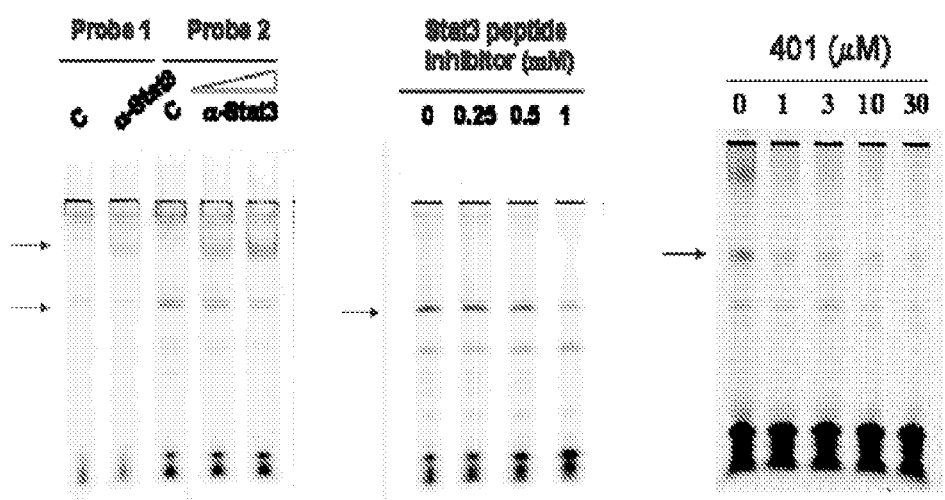
FIG. 7A shows that compound 401 inhibits Stat3 DNA-binding activity in nuclear extract.

Nuclear extracts from HeLa cells, which contain constitutively activated Stat3 as detected by phoshporylation at the tyrosine 705 residue, were used to perform Stat3 EMSAs to monitor Stat3 DNA binding activity. Nuclear extracts were incubated with indicated compound prior to incubation with IR700-labeled Stat3 consensus oligonucleotide. Binding of Stat3 to the oligonucleotide was monitored by gel electrophoresis and detection using a LiCor Odyssey infrared scanner. The Stat3 retarded band was identified and confirmed by supershift with the anti-Stat3 antibody (FIG. 7A, left panel) and dose-dependent inhibition with the Stat3 peptide (FIG. 7A, middle panel). Dose dependent inhibition of Stat3 DNA binding was observed following incubation of the labeled probe with compound 401 (FIG. 7A, right panel).

Figure 7B:
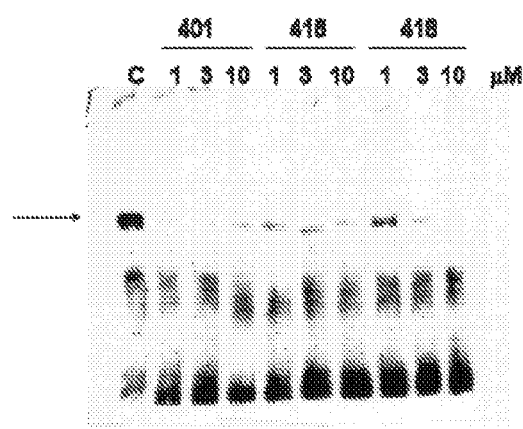
FIG. 7B shows that compounds 401, 416 and 418 inhibit Stat3 DNA-binding activity in nuclear extract.

Additional compounds were tested in the EMSA assays. As shown in FIG. 7B, compounds 401, 416 and 418 can inhibit Stat3's DNA binding activity.

Inhibition of Stat3 Downstream Effectors in Xenograft Tumor Tissues.

Figure 8:
FIG. 8A shows that compound 401 inhibits Stat3 DNA-binding activity in xenograft tumor tissues.
FIG. 8B shows that compound 401 inhibits the expression level of the Stat3 downstream effectors in xenograft tumor tissues.
Figure 8:
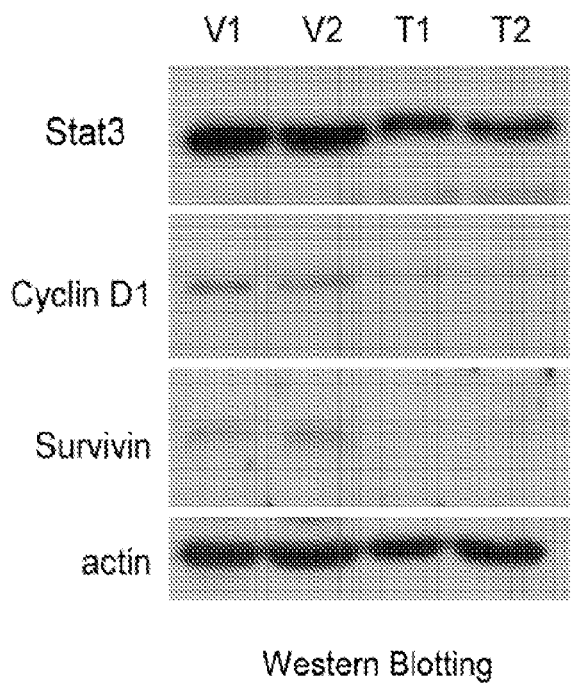

Extracts were prepared from xenografted Paca2 tumors that were treated with compound 401 or vehicle control 4 hours prior to harvest. The samples were analyzed by western blots and EMSA to evaluate the Stat3 downstream effector expression level and Stat3 DNA binding activity. Compound 401 treated sample (T) showed a decrease in Stat3 DNA binding activity over the control (V) (FIG. 8A). In addition, compound 401 treatment resulted in a decrease in the expression level of Stat3's downstream effectors cyclin D1 and survivin (FIG. 8B).

Example 3

Identification of Compounds that Target Cancer Stem Cells

Identification of Compounds that are Apoptotic to Cancer Stem Cells.

Figure 9A:
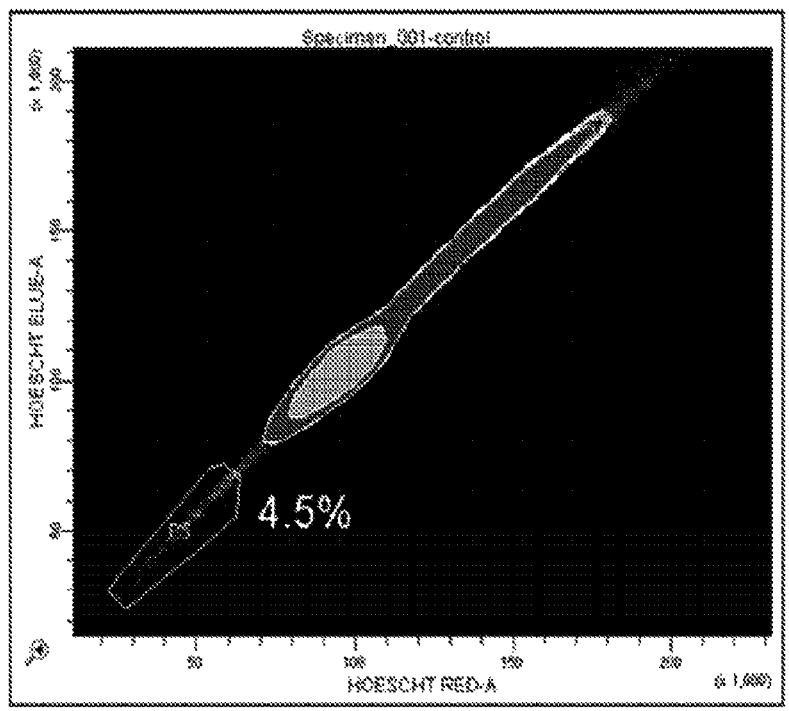
FIG. 9A shows the sorting and analysis of the Hoechst Side Population.
Figure 9A:
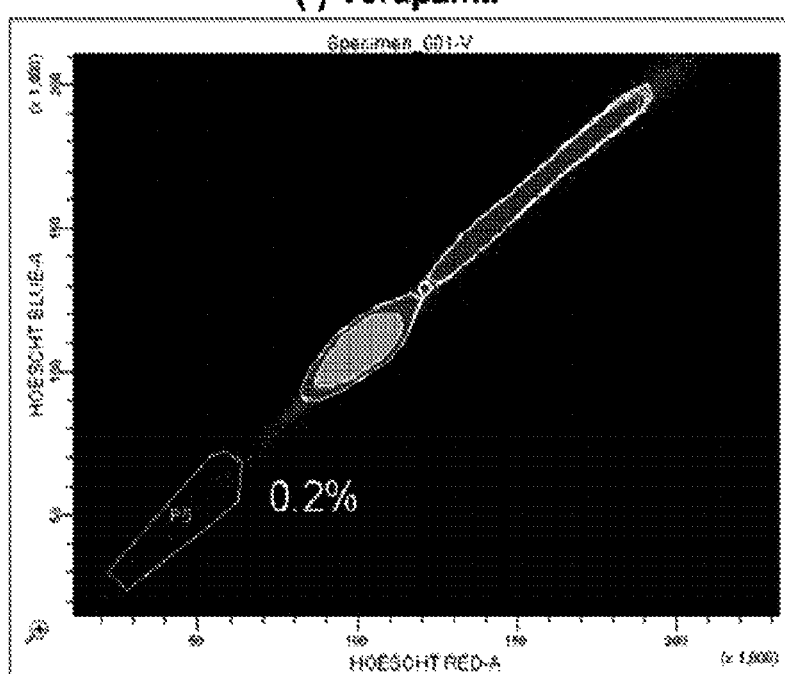

Since cancer stem cells have been demonstrated to actively expel Hoechst, SW480 cells were stained with Hoechst and the side population (shown in FIG. 9A, left panel gated area) was sorted out to enrich the cancer stem cells. To confirm that this side population is enriched with cancer stem cells, a control set of SW480 cells were first treated with Verapamil, an inhibitor of ABC transporters, before stained with Hoechst. As shown in the right panel of FIG. 9A, Verapamil treatment results in the loss of the side population.

Figure 9B:
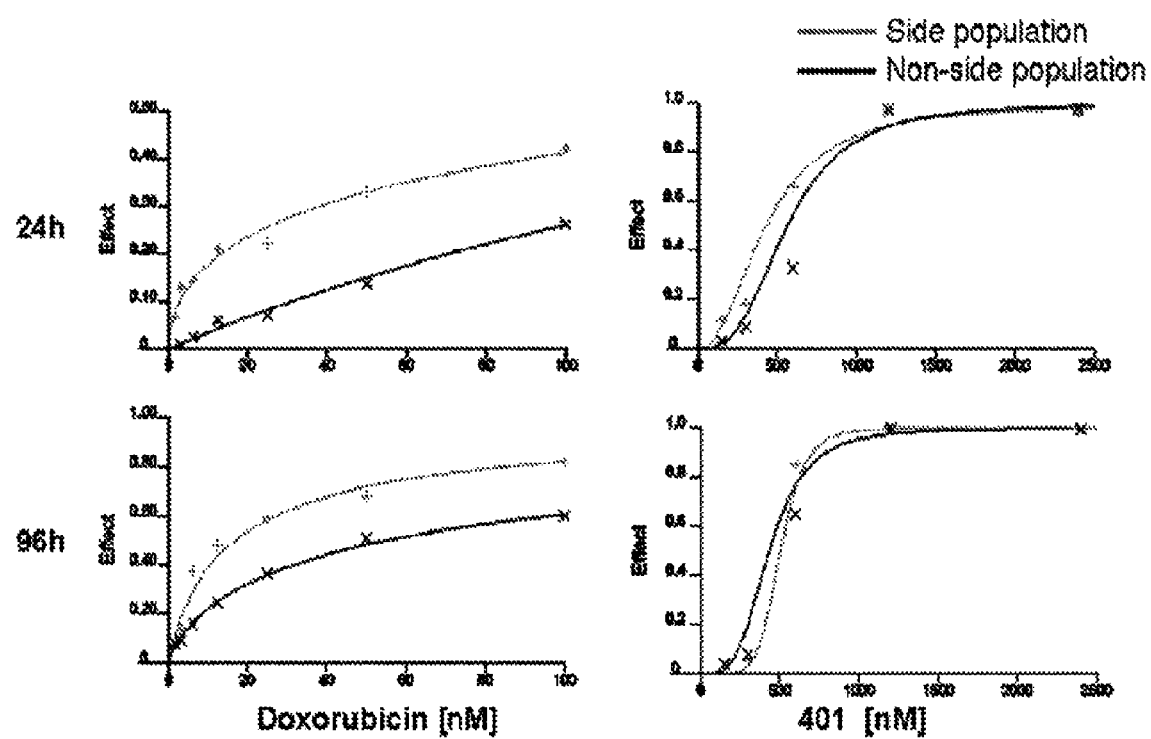
FIG. 9B shows that Hoechst Side Population is as sensitive as non-side population to compound 401.

The $IC_{50}$ of compound 401 against the Hoechst side population was accessed in MTT assays and was compared to the $IC_{50}$ against the non-side population. The results show that the side population is as sensitive as the non-side population to compound 401 (FIG. 9B, right panels). However, the side population is much more resistant than the non-side population to Doxorubicin (FIG. 9B, left panels), which is consistent with previous publications [7, 86]. These data suggest that compound 401 kills cancer stem cells.

Figure 10A:
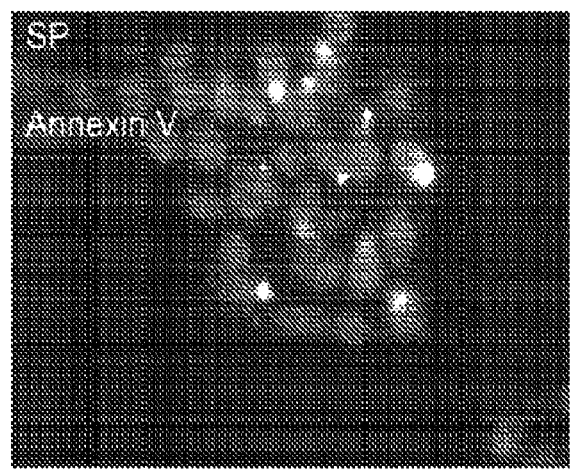
FIG. 10A shows that compound 401 is apoptotic to Hoechst Side Population cells.

The Hoechst side population cells were treated with compound 401 and the mode of cell death was accessed by Annexin V (an early marker for apoptosis) staining. The results show that the dying cells are Annexin V positive (FIG. 10A), demonstrating that compound 401 is apoptotic to cancer stem cells.

Figure 10B:
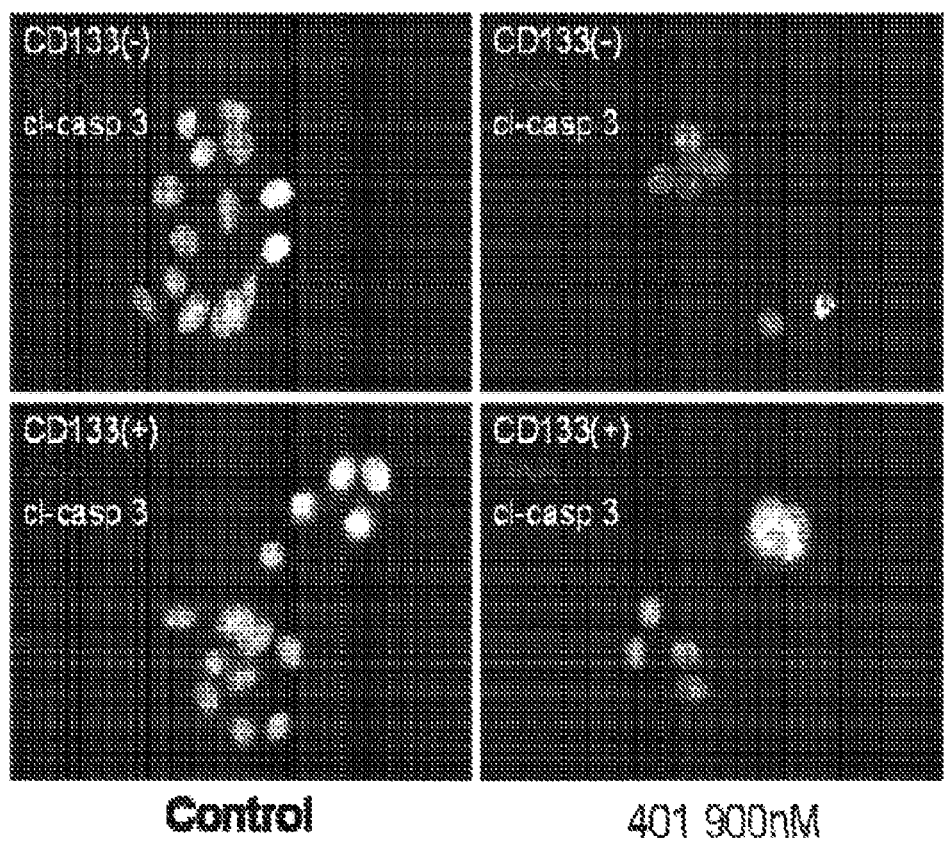
FIG. 10B shows that compound 401 is apoptotic to CD133$^+$ cells.

Alternatively, we performed CD133 (one of the common cancer stem cell surface markers) antibody magnetic bead pull downs to enrich cancer stem cells. The CD133$^+$ cells were then treated with compound 401 followed by staining with antibody against cleaved-Caspase 3 (a hallmark of apoptosis). As shown in FIG. 10B, many of the CD133$^+$ cells become cleaved-Caspase 3 positive after compound 401 treatment, corroborating that compound 401 is apoptotic to cancer stem cells.

In addition, we tested the activities of several other compounds against cancer stem cells. Briefly, freshly isolated CSCs (SW480 Hoechst SP cells or CD44$^{high}$ FaDu cells) were exposed to a dose range (30-0.117 µM) of compound for 48 h before examining cell viability by MTT assay. IC$_{50}$s were estimated by plotting the percentage of surviving cells. As shown in Table 4 and Table 5, compounds of present invention can target cancer stem cells.

TABLE 4

| Compound | IC$_{50}$ (µM) | |
|---|---|---|
| | NSP | SP |
| 401 | 0.33 | 0.34 |
| 418 | 0.33 | 0.34 |
| 4011 | 0.34 | 0.38 |
| 4012 | 0.81 | 0.57 |

TABLE 5

| Compound | IC$_{50}$ (µM) | |
|---|---|---|
| | CD44$^{low}$ | CD44$^{high}$ |
| 4011 | 0.42 | 0.27 |
| 4012 | 0.76 | 1.05 |

Identification of Compounds that Inhibit CSC Spherogenesis In Vitro.

Figure 11:
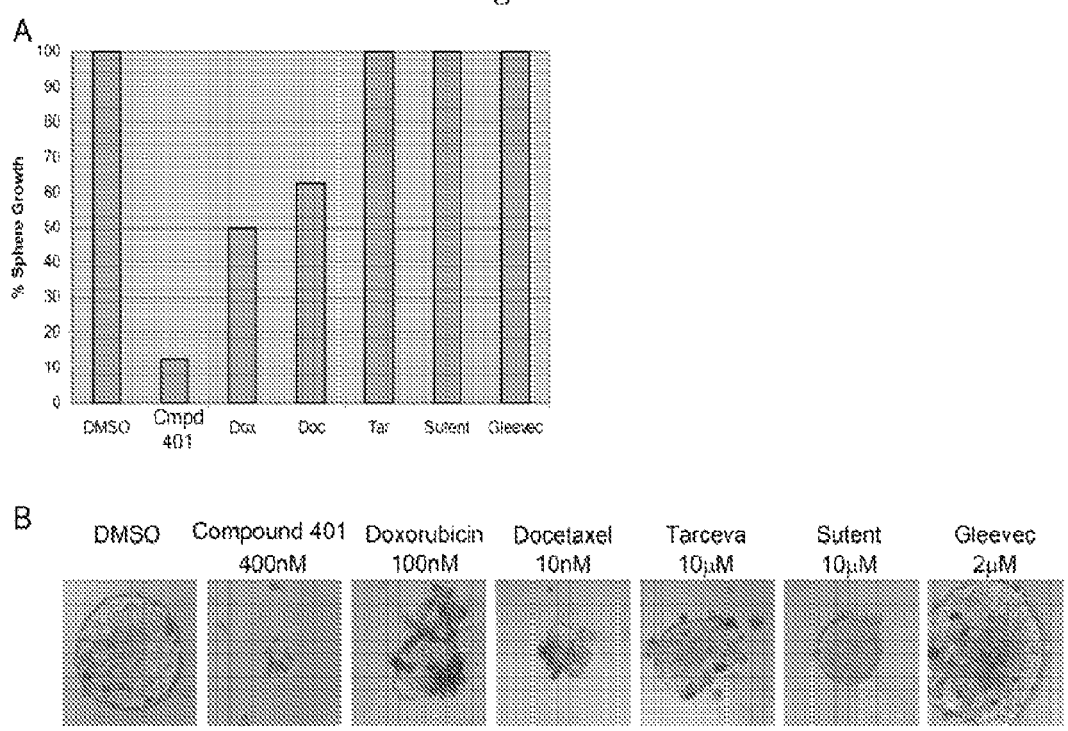
FIG. 11 shows that compound 401 blocks CD44$^{high}$ sphere formation.

One of the hallmarks cancer stem cells is their ability to self-renew [87]. A reliable method of measuring the self-renewal capacity of cell populations is the ability to be cultured as spheres in the absence of serum or attachment [88]. To compare the ability of compound 401 to other targeted and chemotherapeutic agents, FACS-isolated CD44$^{high}$ CSCs were grown as spheres for 72 hours before being challenged with a panel of therapeutic agents. Of the agents tested, only compound 401 was effective at preventing sphere proliferation (FIG. 11). Note that spheres were resistant to doxorubicin and docetaxel despite being applied at approximately ten times their IC$_{50}$ concentrations for cell death in similar assays. Tarceva, Sutent, and Gleevec were added at approximately three times their reported therapeutic concentrations. This demonstrates that while cancer stem cells are resistant to conventional chemotherapeutic and targeted agents, compound 401 is highly effective at inhibiting their growth.

Identification of Compounds that Inhibit CSC Spherogenesis In Vivo.

Figure 12:
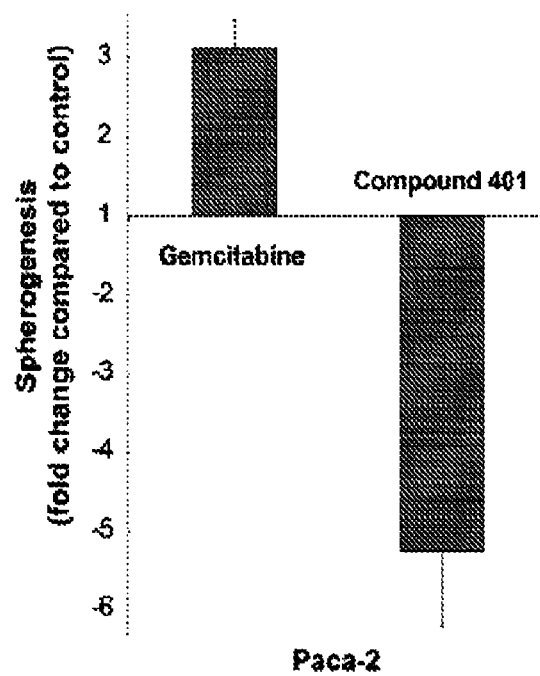
FIG. 12 shows that in vivo compound 401 treatment decreases the spherogenesis of the xenografted tumor cells.
Figure 12:
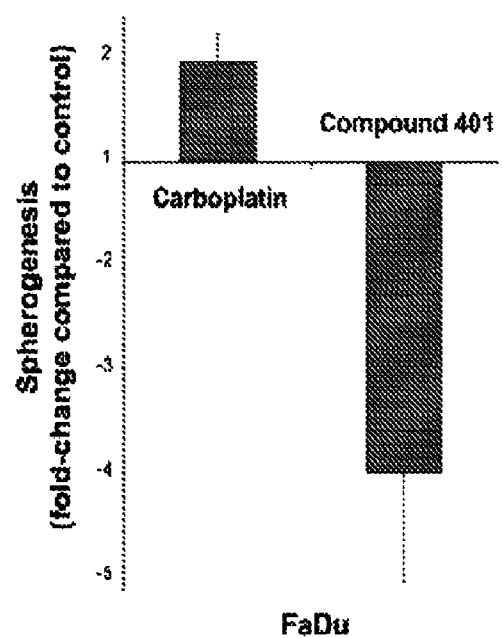

Six-week-old female athymic nu/nu mice were obtained from Charles River Labs (Wilmington, Mass.). Mice were injected subcutaneously on the flank with 6×10$^6$ FaDu or Paca2 cancer cells in 0.2 mL of serum-free DMEM. After xenografts reached ~200 mm$^3$ in size, animals bearing Paca2 xenograft tumors were administered with either vehicle, gemcitabine (120 mg/kg, twice a week), or compound 401 (20 mg/kg) by ip for one week and animals bearing FaDu xenograft tumors were administered daily with either vehicle, carboplatin (30 mg/kg), or compound 401 (20 mg/kg) via ip for two weeks before sacrifice. Tumors were then collected for Paca2 and FaDu cells, respectively. Single cell suspensions were obtained following animal sacrifice, and sterile removal of tumors. Briefly, tumors were minced with sterile scalpels into 0.1 mm$^3$ pieces before being digested in 1 mg/mL collagenase/HBSS for 15-30 minutes with constant agitation. Following passage through a 40 µm mesh filter, RBCs, dead cells, and cell debris were removed by layering the cell suspension onto 1 mL of Histopaque and collecting interface layer after centrifugation at 1440×g for 30 minutes. Live cells were then counted and used to measure their ability to form spheres. Cells were distributed to ultra low attachment 96 well plates at a density of 100 cells per well in cancer stem cell media (DMEM/F12, B27 Neurobasal supplement, 20 ng/mL EGF, 10 ng/mL FGF, 4 µg/mL insulin, and 0.4% BSA). Fresh media was added every three days, and sphere formation was determined after 10-14 days in culture. Spheres with >50 cells were scored. At conclusion of experiment, trypan blue was added to identify dead cells. As shown in FIG. 12, standard chemotherapies gemcitabine (upper panel) and carboplatin (bottom panel) enriched cancer stem cells evidenced by the increased spherogenesis. In contrast, compound 401 treatments decreased cancer stem cells evidenced by the decreased spherogenesis.

Example 4

Identification of Compounds that Selectively Kill a Broad Spectrum of Cancer Cells Identification of Compounds that are Apoptotic to a Broad Spectrum of Cancer Cells In Vitro.

Cells plated in 96 well plates and treated with indicated compounds were subjected to MTT analysis at 24 hours following compound treatment to determine cell viability. IC$_{50}$ values calculated across multiple cell lines are summarized in Table 6 below. The data demonstrate that these compounds have potent activity against broad spectrum of cancer cells.

TABLE 6

| Cell Line | Tissue | IC$_{50}$ (µM) | | | | | | |
|---|---|---|---|---|---|---|---|---|
| | | 4011 | 4012 | 101 | 301 | 401 | 416 | 418 |
| A549 | Lung | | | | | 0.95 | 1.90 | 1.06 |
| H1299 | Lung | | | 3-10 | 0.794 | 0.23 | 0.25 | 0.34 |
| MCF7 | Breast | | | | | 0.46 | 0.75 | 0.46 |
| HeLa | Cervix | | | 11.7 | 3.358 | 0.43 | 0.62 | 0.80 |
| DLD1 | Colon | | | | | 0.33 | 0.54 | 0.64 |
| SW480 | Colon | | | | | 0.32 | 0.44 | 0.76 |
| HCT116 | Colon | | | | | 0.58 | 0.69 | 0.61 |
| HT29 | Colon | | | | | 1.27 | 1.91 | 1.83 |
| HepG2 | Liver | | | | | 0.25 | | |
| Paca2 | Pancreas | 0.446 | | | | 0.11 | 0.21 | 0.21 |

TABLE 6-continued

| Cell Line | Tissue | 4011 | 4012 | 101 | 301 | 401 | 416 | 418 |
|---|---|---|---|---|---|---|---|---|
| | | | | IC$_{50}$ (µM) | | | | |
| Panc1 | Pancreas | | | | | 1.70 | 2.59 | 1.54 |
| DU145 | Prostate | | | 3.7 | 0.835 | 0.12 | 0.22 | 0.18 |
| PC3 | Prostate | | | | | 2.37 | 3.10 | 3.04 |
| LNCap | Prostate | | | | | 0.63 | | |
| FaDu | Head and Neck | 0.353 | 1.041 | | | 0.39 | | |

Figure 13:
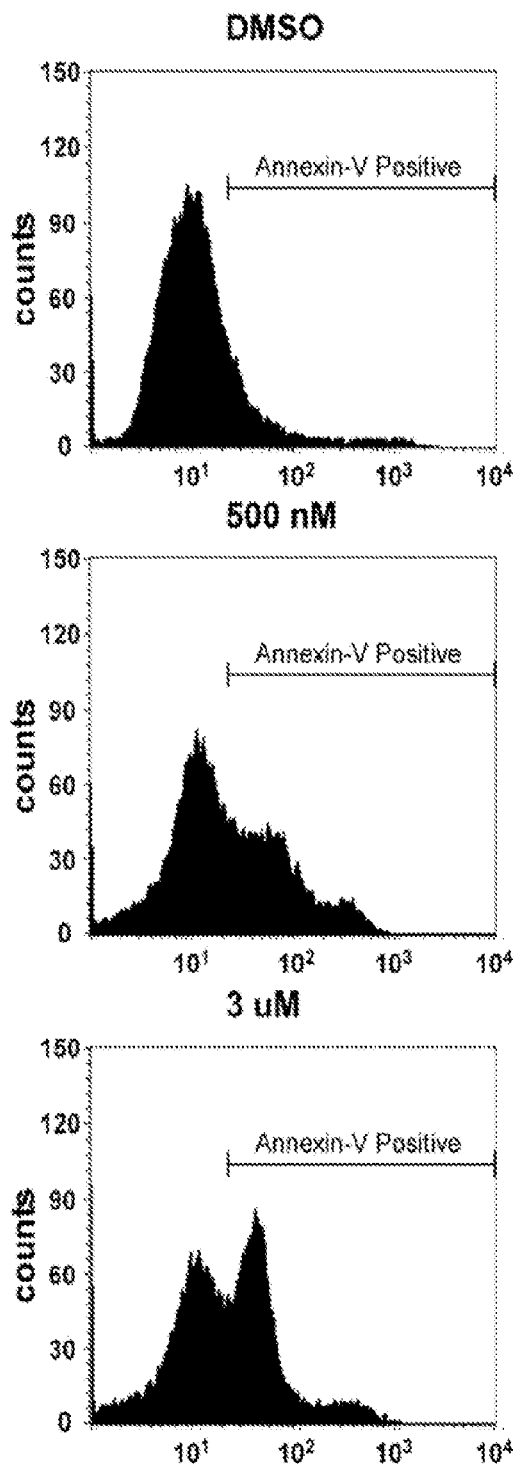
FIG. 13 shows that compound 401 induces apoptosis in cancer cells.

Additionally, DU145 cells were first treated with DMSO or the indicated concentrations of compound 401, then stained with Annexin V, and followed by Flow cytometry analysis 5 hours post-treatment. The results show that 401 treatment results in a dose-dependent increase in the Annexin V staining (FIG. 13), demonstrating that compound 401 is apoptotic to these cancer cells.

Examples of the Selectivity of the Compounds.

Under assay conditions that result in the death of virtually all cancer cells, normal cells remain substantially viable. Peripheral blood mononuclear cells (PBMCs) were relatively resistant to compound 401, having an MTT IC$_{50}$ of 14 µM following a 24 hour incubation with the compound 401. This IC$_{50}$ is between 6 to 116-fold greater than those seen in a variety of cancer cell lines, indicating a reasonable therapeutic window compared to cancer cells.

In a similar fashion to PMBCs, CD34$^+$ bone marrow hematopoietic stem cells were spared when treated with compound 401. As shown in Table 7, incubation of CD34$^+$ bone marrow mononuclear cells for 6 hours with compound 401 resulted in an IC$_{50}$ of greater than 30 µM for both the bone marrow erythroid and myeloid lineages, while DU145 prostate and HT29 colon cancer cells have IC$_{50}$'s less than 0.5 µM under similar conditions. These data suggest a wide (greater than 50 fold) therapeutic window for compound 401 according to the in vitro data.

TABLE 7

Compound 401 is Relatively Non-Toxic
to CD34$^+$ Bone Marrow Stem Cells
Compound 401 IC$_{50}$ (µM)

| Normal Cells | | Cancer Cells | |
|---|---|---|---|
| CD34$^+$ BM Erythroid | CD34$^+$ BM Myeloid | DU145 | HT29 |
| >30 | >30 | <0.2 | <0.5 |

BM = Bone Marrow
Comparison of the IC$_{50}$ of compound 401 on CD34$^+$ Bone Marrow mononuclear cells, DU145 cells and FaDu cells in colony formation assays.

Example 5

In Vivo Anti-Tumor Efficacy

Pancreatic Cancer Xenograft Model.

Figure 14:
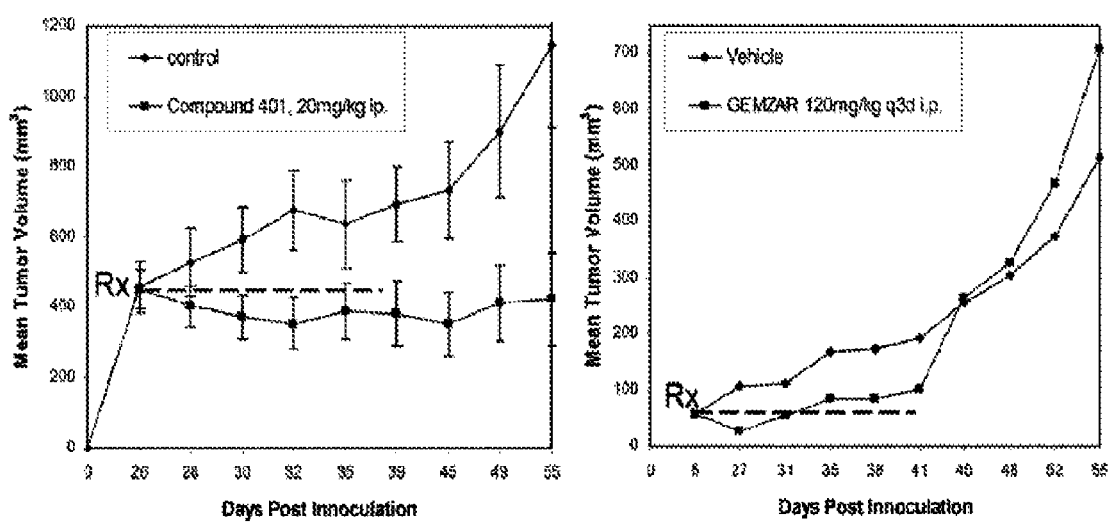
FIG. 14 shows that compound 401 exhibits antitumor activity in human pancreatic cancer xenograft model and behaves differently from standard chemotherapy in that it abolishes tumor rebound.

Paca-2 cells were inoculated subcutaneously into female athymic nude mice (4×10$^6$ cells/mouse). When the tumors reached approximately 450 mm$^3$, the animals were randomly divided into 2 groups with five mice per group. The mice were treated intraperitoneally with either compound 401 at 20 mg/kg or vehicle control daily. Compound 401 was formulated at 5 mg/ml in 1.5% lipids and H$_2$O. The animals received a total of 14 doses and left for post-treatment observation. Tumors were measured throughout treatment and were monitored for another 22 days post-treatment. As shown in FIG. 14 left panel, compound 401 potently inhibited the tumor growth. The tumor growth inhibition was calculated to be 64% on day 60 and was statistically significant (p<0.001). More importantly, tumor volumes remained static during the 22-day post-treatment period.

In a similar experiment, pane-1 human pancreatic cancer cells were inoculated subcutaneously into female athymic nude mice (2×10$^6$ cells/mouse) and allowed to form palpable tumors. When the tumors reached approximately 60 mm$^3$, the animals were randomly divided into 2 groups with 5 mice per group. The mice were treated intraperitoneally (ip) with gemcitabine with a standard regiment (120 mg/kg once every three days) or vehicle control, for a total of 6 doses of gemcitabine or vehicle control. Tumors were measured throughout treatment and were monitored for another 19 days post-treatment. As shown in FIG. 14 right panel, treatment with gemcitabine as a monotherapy inhibited tumor growth with a tumor growth inhibition of 47.5% on day 41. After the treatment was stopped, the tumors in the gemcitabine treated group soon outgrew the ones in the control group.

No tumor rebound was observed during compound 401 treatment or post-treatment period in the xenografted Paca-2 human pancreatic cancer model, which is consistent with its cancer stem cell targeting mechanism of action. In contrast, human pancreatic xenograft tumors treated with current standard chemotherapy gemcitabine responded initially, but rebounded during continual treatment or out-grew the control tumors after dosing stopped. The abolition of the tumor rebound differentiates compound 401 from the standard chemotherapies, offering a possibility to dramatically and fundamentally improve cancer therapy.

Head and Neck Cancer Xenograft Model.

Figure 15:
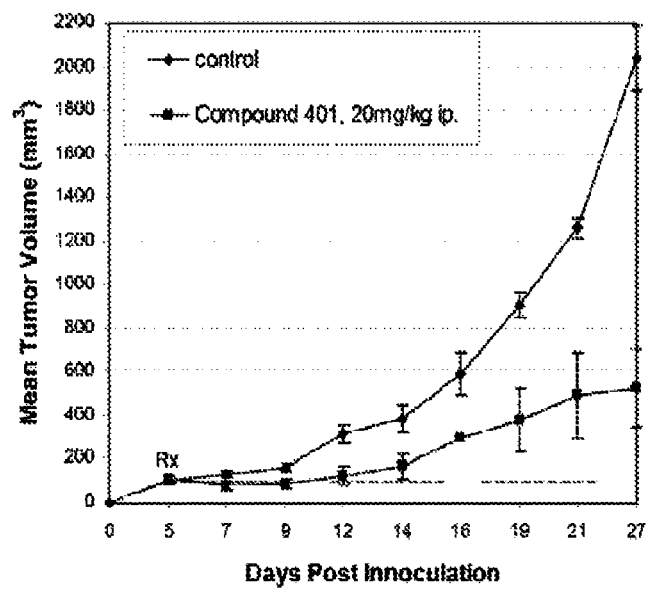
FIG. 15 shows that compound 401 exhibits antitumor activity in human head and neck cancer xenograft model.

FaDu human head and neck cancer cells were inoculated subcutaneously into female athymic nude mice (6×10$^6$ cells/mouse) and allowed to form palpable tumors. When the tumors reached approximately 100 mm$^3$, the animals were treated intraperitoneally (ip) with compound 401 at 20 mg/kg or vehicle control daily (5 consecutive days, followed by a 2 day dosing holiday). Compound 401 was formulated at 5 mg/ml in 2% lipids, 0.1% cholesterol, and H$_2$O. The animals received a total of 15 doses of compound 401 or vehicle control. Tumors were measured throughout treatment. As shown in FIG. 15 in this highly aggressive head and neck xenograft model, animals dosed with compound 401 intraperitoneally as a monotherapy potently inhibited tumor growth. Tumor growth inhibition of compound 401 was calculated to be 75% with a p value of 0.007. There was no significant change in body weight due to intraperitoneal administration of the vehicle or compound 401 at 20 mg/kg.

Breast Cancer Xenograft Model.

Figure 16:
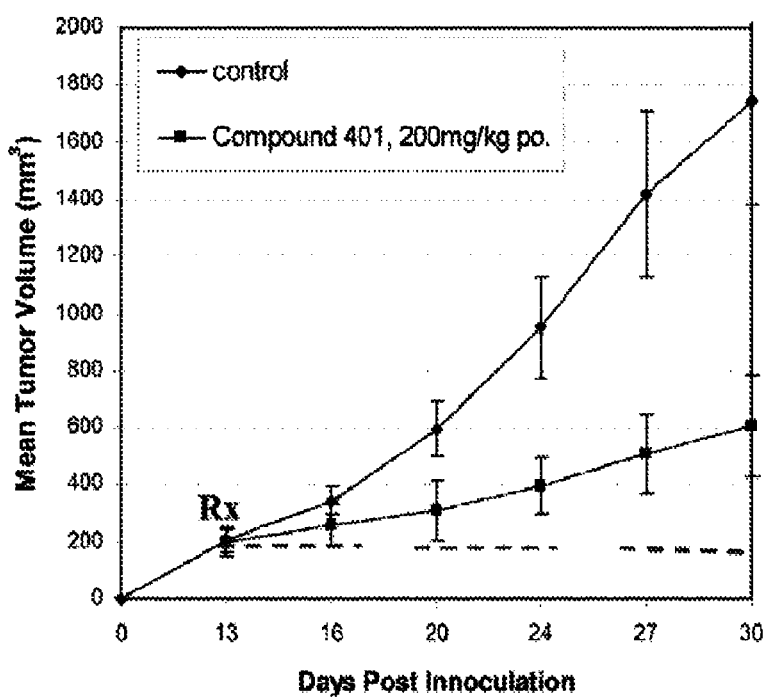
FIG. 16 shows that compound 401 exhibits antitumor activity in human breast cancer xenograft model.

MDA-MB-231 human breast cancer cells were inoculated subcutaneously into female athymic nude mice (8×10$^6$ cells/mouse) and allowed to form palpable tumors. When the tumors reached approximately 200 mm$^3$, the animals were treated orally (po) with compound 401 at 200 mg/kg or vehicle control daily (5 consecutive days, followed by a 2 day dosing holiday). Compound 401 was formulated at 20 mg/ml in 8% gelucire and 20% vitamine E. The animals received a total of 15 doses of compound 401 or vehicle control. Tumors were measured throughout treatment. As shown in FIG. 16, oral dosing of compound 401 as a monotherapy at 200 mg/kg potently inhibited tumor growth. The optimal tumor growth inhibition of compound 401 was calculated to be 66% with a p value of 0.0068. There was no significant change in body weight due to po administration of the vehicle or compound 401 at 200 mg/kg. These data suggest that compound 401 can be safely dosed in a regimen that is effective in this model of human breast cancer.

Prostate Cancer Xenograft Model.

Figure 17:
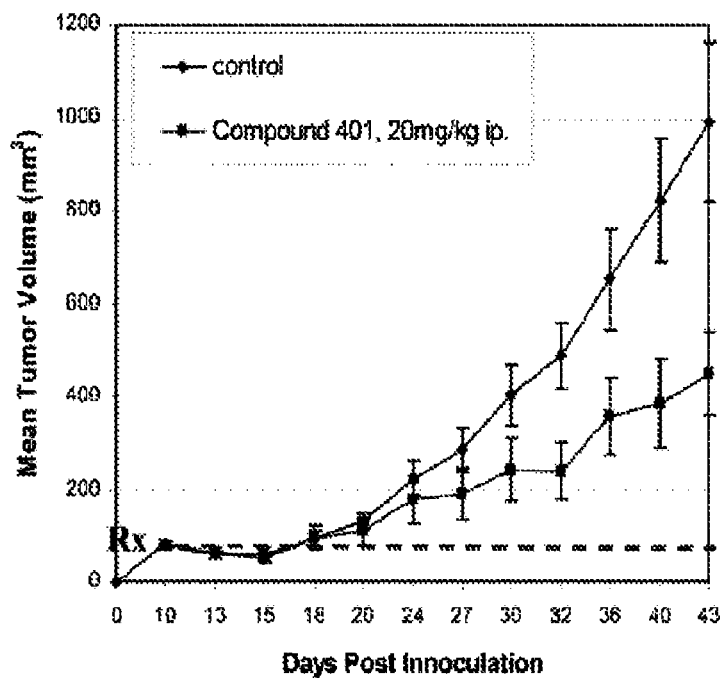
FIG. 17 shows that compound 401 exhibits antitumor activity in human prostate cancer xenograft model.

PC3 human prostate cancer cells were inoculated subcutaneously into female athymic nude mice ($8 \times 10^6$ cells/mouse) and allowed to form palpable tumors. When the tumors reached approximately 100 mm$^3$, the animals were treated intraperitoneally (ip) with compound 401 at 20 mg/kg or vehicle control daily. Compound 401 was formulated at 5 mg/ml in 2% lipids, 0.1% cholesterol, and H$_2$O. The animals received a total of 30 doses of compound 401 or vehicle control. Tumors were measured throughout treatment. As shown in FIG. 17, ip dosing of compound 401 as a monotherapy at 20 mg/kg inhibited tumor growth. The optimal tumor growth inhibition of compound 401 was calculated to be 55% with a p value of 0.015. There was no significant change in body weight due to ip administration of the vehicle or compound 401 at 20 mg/kg. These data suggest that compound 401 can be safely dosed in a regimen that is effective in this model of human prostate cancer.

Gastric Cancer Xenograft Model.

Figure 18:
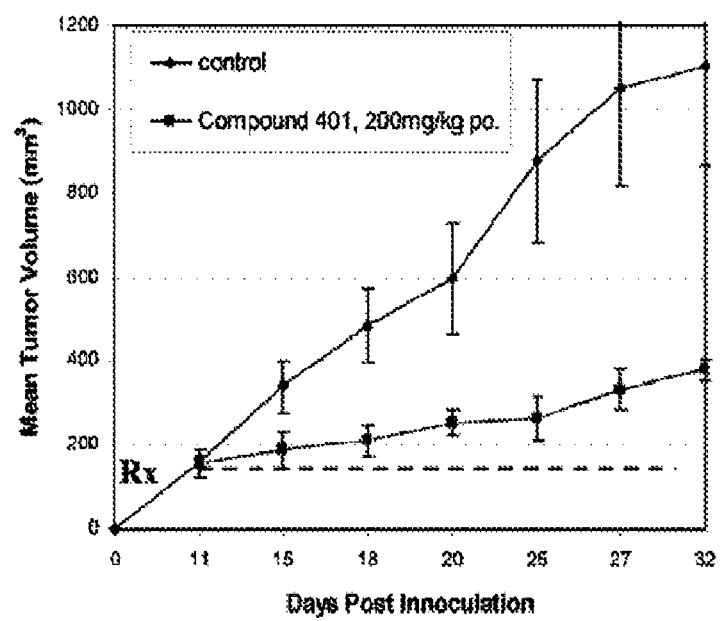
FIG. 18 shows that compound 401 exhibits antitumor activity in human gastric cancer xenograft model.

MKN-45 human gastric cancer cells were inoculated subcutaneously into female athymic nude mice ($8 \times 10^6$ cells/mouse) and allowed to form palpable tumors. When the tumors reached approximately 180 mm$^3$, the animals were administered orally (po) with compound 401 at 200 mg/kg or vehicle control daily. Compound 401 was formulated at 20 mg/ml in 8% gelucire and 20% vitamin E. The animals received a total of 20 doses of compound 401 or vehicle control. Tumors were measured throughout treatment. As shown in FIG. 18, oral dosing of compound 401 as a monotherapy at 200 mg/kg inhibited tumor growth. The optimal tumor growth inhibition of compound 401 was calculated to be 70% with a p value of 0.01. There was no significant change in body weight due to oral administration of the vehicle or compound 401 at 200 mg/kg. These data suggest that compound 401 can be safely dosed in a regimen that is effective in this model of human gastric cancer.

Liver Cancer Xenograft Model.

Figure 19:
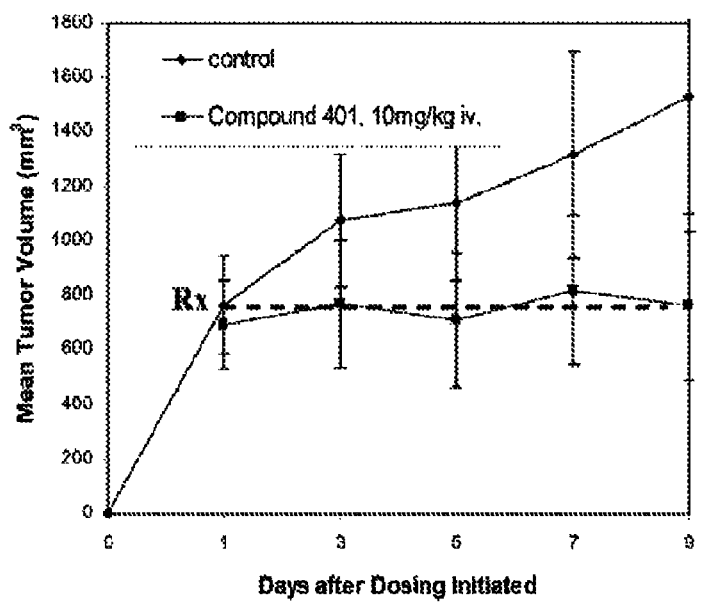
FIG. 19 shows that compound 401 exhibits antitumor activity in human liver cancer xenograft model.

HepG2 human liver cancer cells were inoculated subcutaneously into female athymic nude mice ($8 \times 10^6$ cells/mouse) and allowed to form palpable tumors. In this study, dosing began when the tumors reached approximately 700 mm$^3$. Animals were treated intravenously (iv) with compound 401 at 10 mg/kg or vehicle control daily. Compound 401 was formulated at 2 mg/ml in 1.5% albumin. The animals received a total of 10 doses of compound 401 or vehicle control. Tumors were measured throughout treatment. As shown in FIG. 19, even though treatment started at a much later stage of tumor growth, iv treatment with compound 401 as a monotherapy at 10 mg/kg still potently inhibited tumor growth. The optimal tumor growth inhibition of compound 401 was calculated to be 52.3% with a p value of 0.05. There was no significant change in body weight due to iv administration of the vehicle or compound 401 at 10 mg/kg. These data suggest that compound 401 can be safely dosed in a regimen that is effective in this model of human liver cancer.

Example 6

Anti-Metastasis Efficacy

Figure 20:
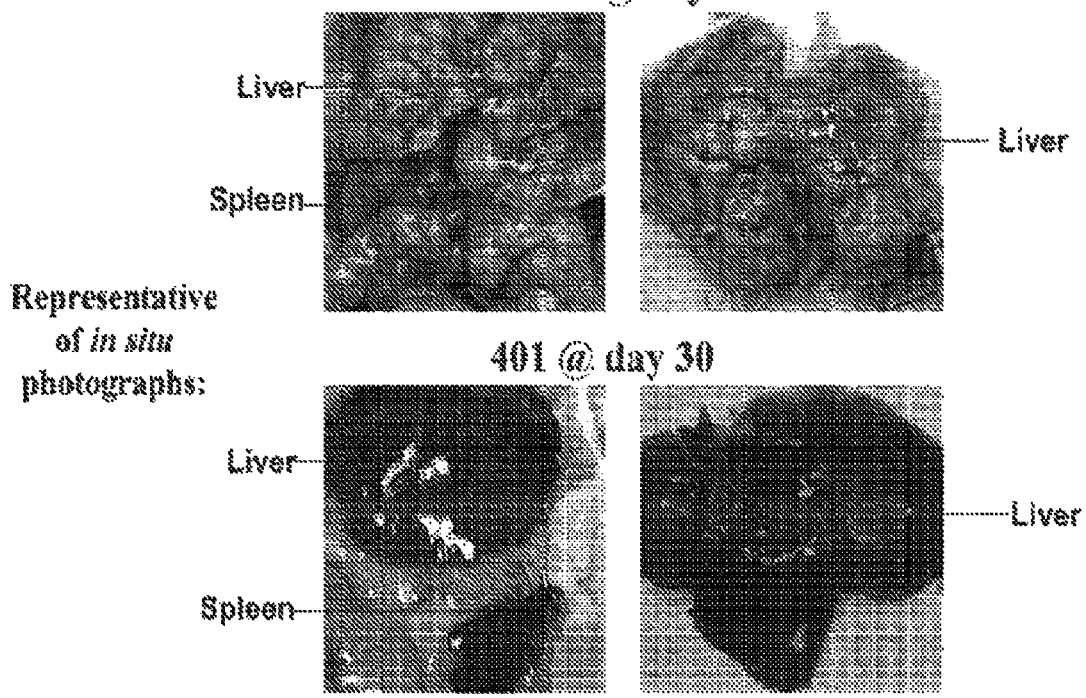
FIG. 20 shows that compound 401 inhibits metastasis in ISMS model.

Compound 401 was also tested for its capability to inhibit metastasis in ISMS model. The intrasplenic-nude mouse model system (ISMS model) is appropriate for studies of the malignant behavior of colorectal carcinomas, as this technique can produce experimental metastases in the liver. In this model, one million HT29 cells in 0.1 ml PBS were injected under the spleen capsule of the nude mice. The spleen was replaced in the peritoneal cavity and the incision was closed. Mice were sacrificed when moribund or 30 days after the injection. The spleen and liver were removed and examined, and the number of tumor lesions was recorded. Mice were divided into 2 groups, a control group given vehicle (n=4) and the other group receiving 20 mg/kg compound 401 (n=4). Drug was administered via ip. 5 days/week starting from day 2 to day 30 after i.s. injection. The numbers of primary tumors and metastatic liver tumors were estimated microscopically. Representative pictures are shown in FIG. 20. In the vehicle control group, there was heavy burden of primary tumors at spleen (FIG. 20, upper left panel). Massive spontaneous liver metastases were also observed (FIG. 20, upper right panel). Compound 401 treatments significantly reduce the number of primary tumor foci and the spontaneous liver metastasis (FIG. 20, lower panels).

Example 7

Pharmacokinetics and Toxicity Profile

Figure 21:
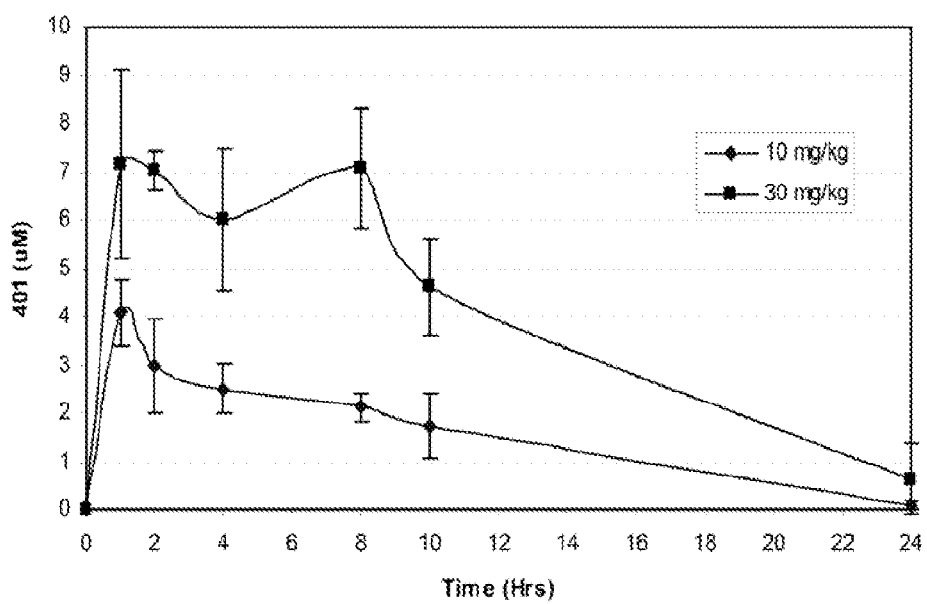
FIG. 21 shows the pharmacokinectics of compound 401 in rats.

A pharmacokinetic analysis of the compound 401 in rats was performed. Female Sprague Dawley rats for pharmacokinetic evaluation (9 rats/group) were dosed via oral gavage. The dose volume was 10 ml/kg with each group given preparations containing the control article (9% Gelucire 44/14 and 18% Vitamin E TPGS in sterile water) or 10 or 30 mg/kg/day of compound 401 in the control article. Blood samples were collected from 3 animals/gender/timepoint predose and approximately 2, 4, 6, 8, 10 and 24 hours after the initial dose. Plasma was harvested by centrifugation and stored in a freezer set to maintain −75° C.±15° C. until analysis. The bioanalytical portion of this study was conducted using a validated LC/MS/MS method. The lower limit of quantitation (LLOQ) was 10.0 ng/mL. As shown in FIG. 21, the pharmacokinetics data showed that compound 401 achieved and maintained a critical concentration of up to 7 µM for up to 8 hr.

At these doses, no toxic effects were observed in rats with continuously dosing for 28 days. This included clinical observation, laboratory tests, gross and histological findings. Together, these data demonstrated that compound 401 can achieve the desired PK exposure for the selective anti-cancer activity.

Example 8

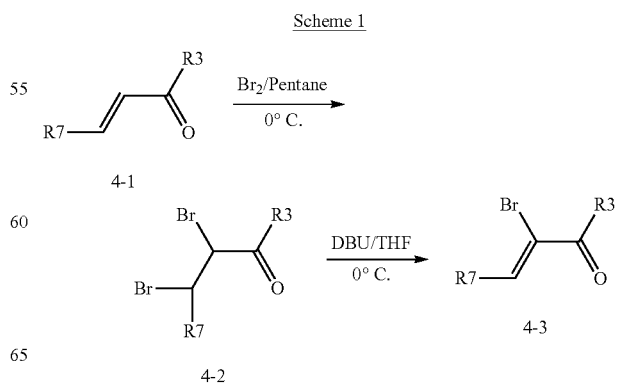

Scheme 1

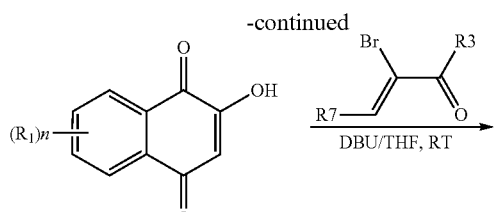

4-4 (or 1-1)

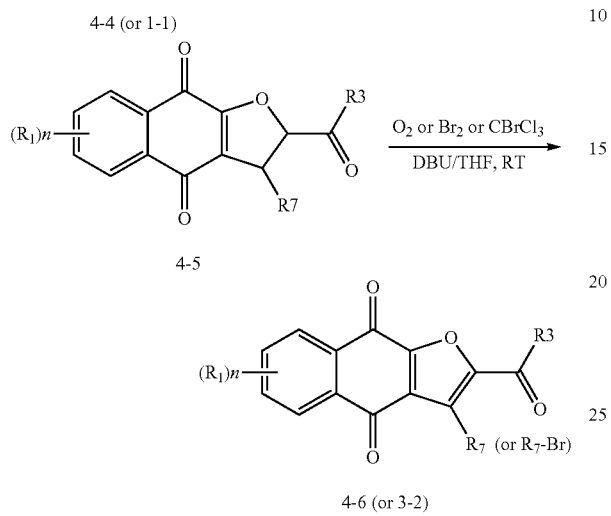

4-6 (or 3-2)

DBU: 1,8-Diazabicyclo[5.4.0]undec-7-ene;
THF: Tetrahydrofuran;
RT: room temperature.

Preparation of 2-Acetyl-4H,9H-naphtho[2,3-b]furan-4,9-dione (compound of formula 4-6 wherein R1=R7=H and R3=—CH$_3$)

To a solution of 18.8 gram (22 ml, 0.268 moles) of 3-buten-2-one (Formula 4-1 in scheme 1) in 200 ml of pentane in ice bath with vigorously stirring, was slowly added 39.0 grams (12.54 ml, 0.244 moles) of bromine in 50 ml of pentane within 30 minutes. After being stirred for additional 5 minutes in ice bath, the mixture was evaporated to remove most of pentane. The small volume of 3,4-dibromo-2-butanone residue (4-2) from step 1 was dissolved in 400 ml of THF, and then chilled in an ice bath. To the solution in ice bath with vigorously stirring, was slowly added 37.2 grams (36.5 ml, 0.244 moles) of DBU in 50 ml of THF within 30 minutes. Large quantity of precipitate salt was generated. The mixture was directly used for next step reaction. To the reaction mixture of 3-bromo-3-buten-2-one (4-3), 38.5 grams (0.220 moles) of 2-hydroxy-1,4-naphthoquinone (4-4) was added. The resulting mixture was stirred vigorously in a room temperature water bath. Then 44.6 grams (43.8 ml, 0.293 moles) of DBU was slowly added to the mixture within 30 minutes. The temperature of the reaction mixture rose by the heat generated from reaction and was controlled to below 35° C. by adding ice to the water bath. After being vigorously stirred for additional 3 hours in open air at room temperature, 1,800 ml of water was added to the mixture. The resulting mixture was chilled to 0° C. and then filtered. The filtered solid was washed successively with 500 ml of water, 500 ml of 5% aqueous sodium bicarbonate, 500 ml of 1% acetic acid and 250 ml of ice chilled acetone. The washed solid was recrystallized in 200 ml of formic acid to yield 12 grams of product with 22.8% overall yield for Compound 4-6 or 3-2 (R1=H, R3=CH$_3$, R7=H) $^1$H NMR (in CDCl$_3$) δ 2.67 (s, 3H), 7.61 (s, 1H-3), 7.79-7.84 (m, 2H), 8.22-8.28 (m, 2H).

Example 9

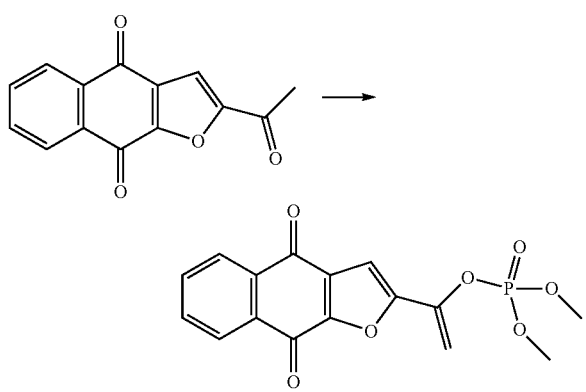

Scheme 2

Preparation of compound phosphoric acid mono-[1-(4,9-dioxo-3a,4,9,9a-tetrahydro-naphtho[2,3-b]furan-2-yl)-vinyl]ester To a solution of BBI6002 (240 mg, 1 mmol) in 50 THF at −78° C. was added lithium bis(trimethylsilyl)amide solution (1.0M in THF, 1.2 mL). After being stirred at this temperature for 1 hour, the reaction mixture was stirred at 0° C. for 30 min. A solution of dimethyl chlorophosphate (217 mg, 1.5 mmol) in 5 mL THF was then added to this mixture at −78° C. The resulted mixture was stirred and allowed to warm to room temperature slowly. After 1 h of stirring at ambient temperature the solvent was evaporated, the residue was dissolved in CH$_2$Cl$_2$, washed with saturated NH$_4$Cl and water and dried over MgSO$_4$. Evaporation of solvent afforded the crude reaction mixture, which was purified from column chromatography to yield phosphoric acid 1-(4,9-dioxo-3a,4,9,9a-tetrahydro-naphtho[2,3-b]furan-2-yl)-vinyl ester dimethyl ester as yellow solid. $^1$H NMR (400 MHz, CDCl$_3$) δ 8.20-8.28 (m, 2H), 7.78-7.82 (m, 2H), 7.07 (s, 1H), 5.78 (t, 1H, J=2.8 Hz), 5.50 (t, 1H, J=2.8 Hz), 3.96 (s, 3H), 3.94 (s, 3H); MS m/z 347.20 (M-H).

Example 10

Scheme 3

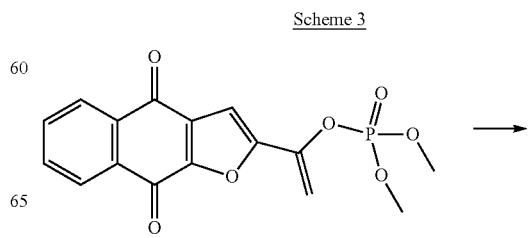

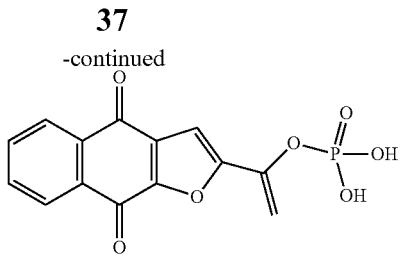

Preparation of compound phosphoric acid 1-(4,9-dioxo-3a,4,9,9a-tetrahydro-naphtho[2,3-b]furan-2-yl)-vinyl ester dimethyl ester To a solution of phosphoric acid 1-(4,9-dioxo-3a,4,9,9a-tetrahydro-naphtho[2,3-b]furan-2-yl)-vinyl ester dimethyl ester (40 mg, 0.114 mmol) in $CH_2Cl_2$ (2 mL) at room temperature was added trimethylsilyl bromide (71 mg, 0.46 mmol). The reaction mixture was stirred at room temperature for 3 hours and then concentrated in vacuum. The residue was purified by semi-prep-HPLC to obtain the product phosphoric acid mono-[1-(4,9-dioxo-3a,4,9,9a-tetrahydro-naphtho[2,3-b]furan-2-yl)-vinyl]ester as yellow solid. $^1H$ NMR (400 MHz, $CDCl_3$) δ $^1H$ NMR (400 MHz, $CDCl_3$) δ 7.98-8.02 (m, 2H), 7.57-7.62 (m, 2H), 6.92 (s, 1H), 5.54 (t, 1H, J=2.8 Hz), 5.36 (t, 1H, J=2.8 Hz); MS m/z 319.20 (M-H).

All references cited herein are incorporated herein by reference in their entirety to the extent allowed by applicable laws and for all purposes to the same extent as if each individual publication or patent or patent application is specifically and individually indicated to be incorporated by reference in its entirety for all purposes. To the extent publications and patents or patent applications incorporated by reference contradict the disclosure contained in the specification, the specification is intended to supersede and/or take precedence over any such contradictory material.

All numbers expressing quantities of ingredients, reaction conditions, analytical results and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only, with a true scope and spirit of the invention being indicated by the following claims.

REFERENCES

1. Bonnet, D., *Normal and leukaemic stem cells*. Br J Haematol, 2005. 130(4): p. 469-79.
2. Bonnet, D. and J. E. Dick, *Human acute myeloid leukemia is organized as a hierarchy that originates from a primitive hematopoietic cell*. Nat Med, 1997. 3(7): p. 730-7.
3. Hambardzumyan, D., M. Squatrito, and E. C. Holland, *Radiation resistance and stem-like cells in brain tumors*. Cancer Cell, 2006. 10(6): p. 454-6.
4. Baumann, M., M. Krause, and R. Hill, *Exploring the role of cancer stem cells in radioresistance*. Nat Rev Cancer, 2008. 8(7): p. 545-54.
5. Ailles, L. E. and I. L. Weissman, *Cancer stem cells in solid tumors*. Curr Opin Biotechnol, 2007. 18(5): p. 460-6.
6. Jones, R. J., W. H. Matsui, and B. D. Smith, *Cancer stem cells: are we missing the target?* J Natl Cancer Inst, 2004. 96(8): p. 583-5.
7. Ho, M. M., et al., *Side population in human lung cancer cell lines and tumors is enriched with stem-like cancer cells*. Cancer Res, 2007. 67(10): p. 4827-33.
8. Wang, J., et al., *Identification of cancer stem cell-like side population cells in human nasopharyngeal carcinoma cell line*. Cancer Res, 2007. 67(8): p. 3716-24.
9. Haraguchi, N., et al., *Characterization of a side population of cancer cells from human gastrointestinal system*. Stem Cells, 2006. 24(3): p. 506-13.
10. Doyle, L. A. and D. D. Ross, *Multidrug resistance mediated by the breast cancer resistance protein BCRP (ABCG2)*. Oncogene, 2003. 22(47): p. 7340-58.
11. Alvi, A. J., et al., *Functional and molecular characterisation of mammary side population cells*. Breast Cancer Res, 2003. 5(1): p. R1-8.
12. Frank, N. Y., et al., *ABCB5-mediated doxorubicin transport and chemoresistance in human malignant melanoma*. Cancer Res, 2005. 65(10): p. 4320-33.
13. Schatton, T., et al., *Identification of cells initiating human melanomas*. Nature, 2008. 451(7176): p. 345-9.
14. Kondo, T., T. Setoguchi, and T. Taga, *Persistence of a small subpopulation of cancer stem-like cells in the C6 glioma cell line*. Proc Natl Acad Sci USA, 2004. 101(3): p. 781-6.
15. Goodell, M. A., et al., *Isolation and functional properties of murine hematopoietic stem cells that are replicating in vivo*. J Exp Med, 1996. 183(4): p. 1797-806.
16. Collins, A. T., et al., *Prospective identification of tumorigenic prostate cancer stem cells*. Cancer Res, 2005. 65(23): p. 10946-51.
17. Li, C., et al., *Identification of pancreatic cancer stem cells*. Cancer Res, 2007. 67(3): p. 1030-7.
18. Ma, S., et al., *Identification and characterization of tumorigenic liver cancer stem/progenitor cells*. Gastroenterology, 2007. 132(7): p. 2542-56.
19. Prince, M. E., et al., *Identification of a subpopulation of cells with cancer stem cell properties in head and neck squamous cell carcinoma*. Proc Natl Acad Sci USA, 2007. 104(3): p. 973-8.
20. Ricci-Vitiani, L., et al., *Identification and expansion of human colon-cancer-initiating cells*. Nature, 2007. 445 (7123): p. 111-5.
21. Singh, S. K., et al., *Identification of a cancer stem cell in human brain tumors*. Cancer Res, 2003. 63(18): p. 5821-8.
22. Dalerba, P., et al., *Phenotypic characterization of human colorectal cancer stem cells*. Proc Natl Acad Sci USA, 2007. 104(24): p. 10158-63.
23. Yu, H. *Stat3: Linking oncogenesis with tumor immune evasion*. in *AACR 2008 Annual Meeting*. 2008. San Diego, Calif.
24. Pedranzini, L., A. Leitch, and J. Bromberg, *Stat3 is required for the development of skin cancer*. J Clin Invest, 2004. 114(5): p. 619-22.

25. Catlett-Falcone, R., et al., *Constitutive activation of Stat3 signaling confers resistance to apoptosis in human U266 myeloma cells*. Immunity, 1999. 10(1): p. 105-15.
26. Bromberg, J. F., et al., *Stat3 as an oncogene*. Cell, 1999. 98(3): p. 295-303.
27. Kanda, N., et al., *STAT3 is constitutively activated and supports cell survival in association with survivin expression in gastric cancer cells*. Oncogene, 2004. 23(28): p. 4921-9.
28. Schlette, E. J., et al., *Survivin expression predicts poorer prognosis in anaplastic large-cell lymphoma*. J Clin Oncol, 2004. 22(9): p. 1682-8.
29. Niu, G., et al., *Constitutive Stat3 activity up-regulates VEGF expression and tumor angiogenesis*. Oncogene, 2002. 21(13): p. 2000-8.
30. Xie, T. X., et al., *Stat3 activation regulates the expression of matrix metalloproteinase-2 and tumor invasion and metastasis*. Oncogene, 2004. 23(20): p. 3550-60.
31. Kortylewski, M., et al., *Inhibiting Stat3 signaling in the hematopoietic system elicits multicomponent antitumor immunity*. Nat Med, 2005. 11(12): p. 1314-21.
32. Burdelya, L., et al., *Stat3 activity in melanoma cells affects migration of immune effector cells and nitric oxide-mediated antitumor effects*. J Immunol, 2005. 174 (7): p. 3925-31.
33. Wang, T., et al., *Regulation of the innate and adaptive immune responses by Stat-3 signaling in tumor cells*. Nat. Med, 2004. 10(1): p. 48-54.
34. Darnell, J. E., *Validating Stat3 in cancer therapy*. Nat Med, 2005. 11(6): p. 595-6.
35. Zhang, L., et al., *Intratumoral delivery and suppression of prostate tumor growth by attenuated Salmonella enterica serovar typhimurium carrying plasmid-based small interfering RNAs*. Cancer Res, 2007. 67(12): p. 5859-64.
36. Campbell, I. L., *Cytokine-mediated inflammation, tumorigenesis, and disease-associated JAK/STAT/SOCS signaling circuits in the CNS*. Brain Res Brain Res Rev, 2005. 48(2): p. 166-77.
37. Harris, T. J., et al., *Cutting edge: An in vivo requirement for STAT3 signaling in TH17 development and TH17-dependent autoimmunity*. J Immunol, 2007. 179(7): p. 4313-7.
38. Libby, P., P. M. Ridker, and A. Maseri, *Inflammation and atherosclerosis*. Circulation, 2002. 105(9): p. 1135-43.
39. Stephens, J. W., et al., *A common functional variant in the interleukin-6 gene is associated with increased body mass index in subjects with type 2 diabetes mellitus*. Mol Genet Metab, 2004. 82(2): p. 180-6.
40. Cesari, M., et al., *Inflammatory markers and onset of cardiovascular events: results from the Health ABC study*. Circulation, 2003. 108(19): p. 2317-22.
41. Orshal, J. M. and R. A. Khalil, *Interleukin-6 impairs endothelium-dependent NO-cGMP-mediated relaxation and enhances contraction in systemic vessels of pregnant rats*. Am J Physiol Regul Integr Comp Physiol, 2004. 286(6): p. R1013-23.
42. Manolagas, S. C., *Role of cytokines in bone resorption*. Bone, 1995. 17(2 Suppl): p. 63S-67S.
43. Yaffe, K., et al., *Inflammatory markers and cognition in well-functioning African-American and white elders*. Neurology, 2003. 61(1): p. 76-80.
44. Watson, C. J. and W. R. Miller, *Elevated levels of members of the STAT family of transcription factors in breast carcinoma nuclear extracts*. Br J Cancer, 1995. 71(4): p. 840-4.
45. Song, J. I. and J. R. Grandis, *STAT signaling in head and neck cancer*. Oncogene, 2000. 19(21): p. 2489-95.
46. Song, L., et al., *Activation of Stat3 by receptor tyrosine kinases and cytokines regulates survival in human non-small cell carcinoma cells*. Oncogene, 2003. 22(27): p. 4150-65.
47. Savarese, T. M., et al., *Coexpression of oncostatin M and its receptors and evidence for STAT3 activation in human ovarian carcinomas*. Cytokine, 2002. 17(6): p. 324-34.
48. Toyonaga, T., et al., *Blockade of constitutively activated Janus kinase/signal transducer and activator of transcription-3 pathway inhibits growth of human pancreatic cancer*. Cancer Lett, 2003. 201(1): p. 107-16.
49. Corvinus, F. M., et al., *Persistent STAT3 activation in colon cancer is associated with enhanced cell proliferation and tumor growth*. Neoplasia, 2005. 7(6): p. 545-55.
50. Gao, B., et al., *Constitutive activation of JAK-STAT3 signaling by BRCA1 in human prostate cancer cells*. FEBS Lett, 2001. 488(3): p. 179-84.
51. Buettner, R., L. B. Mora, and R. Jove, *Activated STAT signaling in human tumors provides novel molecular targets for therapeutic intervention*. Clin Cancer Res, 2002. 8(4): p. 945-54.
52. Carson, W. E., *Interferon-alpha-induced activation of signal transducer and activator of transcription proteins in malignant melanoma*. Clin Cancer Res, 1998. 4(9): p. 2219-28.
53. Chen, C. L., et al., *Stat3 activation in human endometrial and cervical cancers*. Br J Cancer, 2007. 96(4): p. 591-9.
54. Lai, R., et al., *STAT3 is activated in a subset of the Ewing sarcoma family of tumours*. Pathol, 2006. 208(5): p. 624-32.
55. Punjabi, A. S., et al., *Persistent activation of STAT3 by latent Kaposi's sarcoma-associated herpesvirus infection of endothelial cells*. J Virol, 2007. 81(5): p. 2449-58.
56. Schaefer, L. K., et al., *Constitutive activation of Stat3alpha in brain tumors: localization to tumor endothelial cells and activation by the endothelial tyrosine kinase receptor (VEGFR-2)*. Oncogene, 2002. 21(13): p. 2058-65.
57. Puthier, D., R. Bataille, and M. Amiot, *IL-6 up-regulates mcl-1 in human myeloma cells through JAK/STAT rather than ras/MAP kinase pathway*. Eur J Immunol, 1999. 29(12): p. 3945-50.
58. Migone, T. S., et al., *Constitutively activated Jak-STAT pathway in T cells transformed with HTLV-I*. Science, 1995. 269(5220): p. 79-81.
59. Spiekermann, K., et al., *Constitutive activation of STAT transcription factors in acute myelogenous leukemia*. Eur J Haematol, 2001. 67(2): p. 63-71.
60. Epling-Burnette, P. K., et al., *Inhibition of STAT3 signaling leads to apoptosis of leukemic large granular lymphocytes and decreased Mcl-1 expression*. J Clin Invest, 2001. 107(3): p. 351-62.
61. Weber-Nordt, R. M., et al., *Constitutive activation of STAT proteins in primary lymphoid and myeloid leukemia cells and in Epstein-Barr virus (EBV)-related lymphoma cell lines*. Blood, 1996. 88(3): p. 809-16.
62. Sommer, V. H., et al., *In vivo activation of STAT3 in cutaneous T-cell lymphoma. Evidence for an antiapoptotic function of STAT3*. Leukemia, 2004. 18(7): p. 1288-95.
63. Lai, R., et al., *Signal transducer and activator of transcription-3 activation contributes to high tissue inhibitor of metalloproteinase-1 expression in anaplastic lymphoma kinase positive anaplastic large cell lymphoma*. Am J Pathol, 2004. 164(6): p. 2251-8.

64. Fu, X. Y., *STAT3 in immune responses and inflammatory bowel diseases*. Cell Res, 2006. 16(2): p. 214-9.
65. Feldmann, M., F. M. Brennan, and R. N. Maini, *Role of cytokines in rheumatoid arthritis*. Annu Rev Immunol, 1996. 14: p. 397-440.
66. Krause, A., et al., *Rheumatoid arthritis synoviocyte survival is dependent on Stat3*. J Immunol, 2002. 169(11): p. 6610-6.
67. Pfitzner, E., et al., *The role of STATs in inflammation and inflammatory diseases*. Curr Pharm Des, 2004. 10(23): p. 2839-50.
68. Lovato, P., et al., *Constitutive STAT3 activation in intestinal T cells from patients with Crohn's disease*. J Biol Chem, 2003. 278(19): p. 16777-81.
69. Ishihara, K. and T. Hirano, *IL-6 in autoimmune disease and chronic inflammatory proliferative disease*. Cytokine Growth Factor Rev, 2002. 13(4-5): p. 357-68.
70. Ivashkiv, L. B. and I. Tassiulas, *Can SOCS make arthritis better?* J Clin Invest, 2003. 111(6): p. 795-7.
71. Sengupta, T. K., et al., *Activation of monocyte effector genes and STAT family transcription factors by inflammatory synovial fluid is independent of interferon gamma*. J Exp Med, 1995. 181(3): p. 1015-25.
72. Shouda, T., et al., *Induction of the cytokine signal regulator SOCS3/CIS3 as a therapeutic strategy for treating inflammatory arthritis*. J Clin Invest, 2001. 108(12): p. 1781-8.
73. Harada, T., et al., *Increased expression of STAT3 in SLE T cells contributes to enhanced chemokine-mediated cell migration*. Autoimmunity, 2007. 40(1): p. 1-8.
74. Simeone-Penney, M. C., et al., *Airway epithelial STAT3 is required for allergic inflammation in a murine model of asthma*. J Immunol, 2007. 178(10): p. 6191-9.
75. Hagler, M., Smith-Norowitz, T., Chice, S., Wallner, S., Viterbo, D., Mueller, C., Groos, R., Nowakowski, M., Schulze, R., Zenilman, M., *Sophorolipids decrease IgE production in U266 cells by downregulation of BSAP (Pax5), TLR-2, STAT3 and IL-6*. Journal of Allergy and Clinical Immunology, 2007. 119(S1): p. S263-S263.
76. Benkhart, E. M., et al., *Role of Stat3 in lipopolysaccharide-induced IL-10 gene expression*. J Immunol, 2000. 165(3): p. 1612-7.
77. Sano, S., et al., *Stat3 links activated keratinocytes and immunocytes required for development of psoriasis in a novel transgenic mouse model*. Nat Med, 2005. 11(1): p. 43-9.
78. Lim, C. P., et al., *Stat3 contributes to keloid pathogenesis via promoting collagen production, cell proliferation and migration*. Oncogene, 2006. 25(39): p. 5416-25.
79. Arany, I., et al., *Correlation between pretreatment levels of interferon response genes and clinical responses to an immune response modifier (Imiquimod) in genital warts*. Antimicrob Agents Chemother, 2000. 44(7): p. 1869-73.
80. Tefferi, A., *Classification, diagnosis and management of myeloproliferative disorders in the JAK2V617F era*. Hematology Am Soc Hematol Educ Program, 2006: p. 240-5.
81. Roder, S., et al., *STAT3 is constitutively active in some patients with Polycythemia rubra vera*. Exp Hematol, 2001. 29(6): p. 694-702.
82. Kim, O, S., et al., *JAK-STAT signaling mediates gangliosides-induced inflammatory responses in brain microglial cells*. J Biol Chem, 2002. 277(43): p. 40594-601.
83. Wyss-Coray, T., *Inflammation in Alzheimer disease: driving force, bystander or beneficial response?* Nat Med, 2006. 12(9): p. 1005-15.
84. Stelmasiak, Z., et al., *Interleukin-6 concentration in serum and cerebrospinal fluid in multiple sclerosis patients*. Med Sci Monit, 2000. 6(6): p. 1104-8.
85. Ponti, D., et al., *Isolation and in vitro propagation of tumorigenic breast cancer cells with stem/progenitor cell properties*. Cancer Res, 2005. 65(13): p. 5506-11.
86. Szotek, P. P., et al., *Ovarian cancer side population defines cells with stem cell-like characteristics and Mullerian Inhibiting Substance responsiveness*. Proc Natl Acad Sci USA, 2006. 103(30): p. 11154-9.
87. Al-Hajj, M., et al., *Therapeutic implications of cancer stem cells*. Curr Opin Genet Dev, 2004. 14(1): p. 43-7.
88. Bleau, A. M., et al., *New strategy for the analysis of phenotypic marker antigens in brain tumor-derived neurospheres in mice and humans*. Neurosurg Focus, 2008. 24(3-4): p. E28.

The invention claimed is:

1. A method for treating cancer in a human subject in need thereof comprising administering a composition comprising a therapeutically effective amount of 2-acetylnaphtho[2,3-b]furan-4,9-dione and/or a pharmaceutically acceptable solvate thereof,
wherein said 2-acetylnaphtho[2,3-b]furan-4,9-dione is synthetic, and
wherein said cancer is head and neck cancer, brain cancer, breast cancer, lung cancer, liver cancer, pancreatic cancer, ovarian cancer, cervical cancer, uterine cancer, gastrointestinal cancer, kidney cancer, bladder cancer, vulval cancer, cancer of the peritoneum, prostate cancer, thyroid cancer, sarcomas, squamous cell cancer, melanoma, leukemia, lymphoma, or myeloma, wherein said cancer expresses activated STAT3.

2. The method of claim 1, wherein said cancer is metastatic.

3. The method of claim 1, wherein said cancer is refractory to chemotherapy or radiotherapy.

4. The method of claim 1, wherein said cancer is resistant to chemotherapy.

5. The method of claim 1, wherein said cancer has relapsed.

6. The method of claim 1, wherein said cancer is head and neck cancer.

7. The method of claim 6, wherein said head and neck cancer is salivary gland cancer.

8. The method of claim 1, wherein said cancer is brain cancer.

9. The method of claim 8, Wherein said brain cancer is glioblastoma.

10. The method of claim 1, wherein said cancer is breast cancer.

11. The method of claim 1, wherein said cancer is lung cancer.

12. The method of claim 11, wherein said lung cancer is small-cell lung cancer, non-small-cell lung cancer, adenocarcinoma of the lung, and/or squamous carcinoma of the lung.

13. The method of claim 1, wherein said cancer is liver cancer.

14. The method of claim 13, wherein said liver cancer is a hepatocellular carcinoma.

15. The method of claim 1, wherein said cancer is pancreatic cancer.

16. The method of claim 1, wherein said cancer is ovarian cancer.

17. The method of claim 1, wherein said cancer is uterine cancer.

18. The method of claim 17, wherein said uterine cancer is endometrial cancer.

19. The method of claim 1, wherein said cancer is cervical cancer.

20. The method of claim 1, wherein said cancer is gastrointestinal cancer.

21. The method of claim 20, wherein said gastrointestinal cancer is esophageal cancer, gastroesophageal junction cancer, gastric cancer, colon cancer, and/or colorectal cancer.

22. The method of claim 20, wherein said gastrointestinal cancer is esophageal and/or gastroesophageal junction cancer.

23. The method of claim 20, wherein said gastrointestinal cancer is gastric cancer.

24. The method of claim 20, wherein said gastrointestinal cancer is colon cancer.

25. The method of claim 20, wherein said gastrointestinal cancer is colorectal cancer.

26. The method of claim 1, wherein said cancer is cancer of the peritoneum.

27. The method of claim 1, wherein said cancer is kidney cancer.

28. The method of claim 27, wherein said kidney cancer is renal cell carcinoma.

29. The method of claim 1, wherein said cancer is bladder cancer.

30. The method of claim 1, wherein said cancer is vulval cancer.

31. The method of claim 1, wherein said cancer is prostate cancer.

32. The method of claim 1, wherein said cancer is thyroid cancer.

33. The method of claim 1, wherein said cancer is a sarcoma.

34. The method of claim 1, wherein said cancer is squamous cell cancer.

35. The method of claim 1, wherein said cancer is melanoma.

36. The method of claim 1, wherein said cancer is leukemia.

37. The method of claim 1, wherein said cancer is lymphoma.

38. The method of claim 1, wherein said cancer is myeloma.

39. The method of claim 38, wherein said myeloma is multiple myeloma.

40. The method of claim 1, comprising administering said composition to a human subject with cancer, wherein said cancer is head and neck cancer, brain cancer, breast cancer, lung cancer, liver cancer, pancreatic cancer, ovarian cancer, cervical cancer, uterine cancer, gastrointestinal cancer, kidney cancer, bladder cancer, vulval cancer, cancer of the peritoneum, prostate cancer, thyroid cancer, sarcomas, squamous cell cancer, melanoma, leukemia, lymphoma, or myeloma.

41. The method of claim 1, wherein said composition consists of a therapeutically effective amount of 2-acetylnaphtho[2,3-b]furan-4,9-dione and/or a pharmaceutically acceptable solvate thereof.

42. The method of claim 1, wherein said composition further comprises at least one pharmaceutically-acceptable excipient, carrier, or diluent.

43. The method of claim 42, wherein said at least one pharmaceutically-acceptable excipient, carrier, or diluent is chosen from Gelucire®.

44. The method of claim 1, wherein said composition is formulated for oral administration.

45. A method for treating cancer in a human subject comprising administering to a human subject with gastric cancer a composition comprising a therapeutically effective amount of 2-acetylnaphtho[23-b]furan-4,9-dione and/or a pharmaceutically acceptable solvate thereof, wherein said 2-actylnaphtho[2,3-b]furan-4,9-dione is synthetic, and wherein said cancer expresses activated STAT3.

46. A method for treating cancer in a human subject comprising administering to a human subject with gastroesophageal junction cancer a composition comprising a therapeutically effective amount of 2-acetylnaphtho[2,3-b]furan-4,9-dione and/or a pharmaceutically acceptable solvate thereof, wherein said 2-acetylnaphtho[2,3-b]furan-4,9-dione is synthetic, and wherein said cancer expresses activated STAT3.

47. A method for treating cancer in a human subject comprising administering to a human subject with colorectal cancer a composition comprising a therapeutically effective amount of 2-acetylnaphtho[2,3-b]furan-4,9-dione and/or a pharmaceutically acceptable solvate thereof, wherein said 2-actylnaphtho[2,3-b]furan-4,9-dione is synthetic, and wherein said cancer expresses activated STAT3.

48. A method for treating cancer in a human subject comprising administering to a human subject with non-small cell lung cancer a composition comprising a therapeutically effective amount of 2-acetylnaphtho[2,3-b]furan-4,9-dione and/or a pharmaceutically acceptable solvate thereof, wherein said 2-acetylnaphtho[2,3-b]furan-4,9-dione is synthetic, and wherein said cancer expresses activated STAT3.

49. A method for treating cancer in a human subject comprising administering to a human subject with ovarian cancer a composition comprising a therapeutically effective amount of 2-acetylnaphtho[2,3-b]furan-4,9-dione and/or a pharmaceutically acceptable solvate thereof, wherein said 2-actylnaphtho[2,3-b]furan-4,9-dione is synthetic, and wherein said cancer expresses activated STAT3.

50. A method for treating cancer in a human subject comprising administering to a human subject with breast cancer a composition comprising a therapeutically effective amount of 2-acetylnaphtho[2,3-b]furan-4,9-dione and/or a pharmaceutically acceptable solvate thereof, wherein said 2-actylnaphtho[2,3-b]furan-4,9-dione is synthetic, and wherein said cancer expresses activated STAT3.

51. A method for treating cancer in a human subject comprising administering to a human subject with pancreatic cancer a composition comprising a therapeutically effective amount of 2-acetylnaphtho[2,3-b]furan-4,9-dione and/or a pharmaceutically acceptable solvate thereof, wherein said 2-actylnaphtho[2,3-b]furan-4,9-dione is synthetic, and wherein said cancer expresses activated STAT3.

52. A method for treating cancer in a human subject comprising administering to a human subject with hepatocellular carcinoma a composition comprising a therapeutically effective amount of 2-acetylnaphtho[2,3-b]furan-4,9-dione and/or a pharmaceutically acceptable solvate thereof, wherein said 2-actylnaphtho[2,3-b]furan-4,9-dione is synthetic, and wherein said cancer expresses activated STAT3.

53. A method for treating cancer in a human subject comprising administering to a human subject with glioblastoma a composition comprising a therapeutically effective amount of 2-acetylnaphtho[2,3-b]furan-4,9-dione and/or a pharmaceutically acceptable solvate thereof, wherein said 2-actylnaphtho[2,3-b]furan-4,9-dione is synthetic, and wherein said cancer expresses activated STAT3.

* * * * *

UNITED STATES PATENT AND TRADEMARK OFFICE
CERTIFICATE OF CORRECTION

PATENT NO. : 9,745,278 B2
APPLICATION NO. : 12/677513
DATED : August 29, 2017
INVENTOR(S) : Chiang Jia Li et al.

It is certified that error appears in the above-identified patent and that said Letters Patent is hereby corrected as shown below:

In the Specification

Column 20, Line 17, "hydroxypropyl-.beta.-cyclodextrin" should read --hydroxypropyl-β-cyclodextrin--.

Column 24, Line 23, "manufactures" should read --manufacturer's--.

In the Claims

Claim 45, Column 45, Line 53, "2-acetylnaphtho[23-b]furan-4,9-dione" should read as --2-acetylnaphtho[2,3-b]furan-4,9-dione--.

Signed and Sealed this
Nineteenth Day of December, 2017

Joseph Matal
*Performing the Functions and Duties of the
Under Secretary of Commerce for Intellectual Property and
Director of the United States Patent and Trademark Office*

SEQUENCE LISTING

<160> NUMBER OF SEQ ID NOS: 5

<210> SEQ ID NO 1
<211> LENGTH: 24
<212> TYPE: DNA
<213> ORGANISM: Homo sapiens
<220> FEATURE:
<221> NAME/KEY: misc_feature
<222> LOCATION: (1)..(1)
<223> OTHER INFORMATION: 5'-Biotin

<400> SEQUENCE: 1
gatccttctg ggaattccta gatc                                          24

<210> SEQ ID NO 2
<211> LENGTH: 24
<212> TYPE: DNA
<213> ORGANISM: Artificial Sequence
<220> FEATURE:
<223> OTHER INFORMATION: primer

<400> SEQUENCE: 2
ggatctagaa tcagctacag cagc                                          24

```
<210> SEQ ID NO 3
<211> LENGTH: 24
<212> TYPE: DNA
<213> ORGANISM: Artificial Sequence
<220> FEATURE:
<223> OTHER INFORMATION: primer

<400> SEQUENCE: 3
tcctctagag ggcaatctcc attg                                          24

<210> SEQ ID NO 4
<211> LENGTH: 22
<212> TYPE: DNA
<213> ORGANISM: Artificial Sequence
<220> FEATURE:
<223> OTHER INFORMATION: primer

<400> SEQUENCE: 4
ccctctagat ggttcctgga ac                                            22

<210> SEQ ID NO 5
<211> LENGTH: 21
<212> TYPE: DNA
<213> ORGANISM: Artificial Sequence
<220> FEATURE:
<223> OTHER INFORMATION: primer

<400> SEQUENCE: 5
gctctagaaa cccctttttg g                                             21
```